United States Patent
An et al.

(10) Patent No.: US 9,234,018 B2
(45) Date of Patent: Jan. 12, 2016

(54) COMPOSITIONS AND METHODS FOR THE TREATMENT OF VPRBP-RELATED CANCERS

(71) Applicants: Woojin An, Los Angeles, CA (US); Nouri Neamati, Ann Arbor, MI (US); Kyunghwan Kim, Los Angeles, CA (US); Wange Lu, Los Angeles, CA (US)

(72) Inventors: Woojin An, Los Angeles, CA (US); Nouri Neamati, Ann Arbor, MI (US); Kyunghwan Kim, Los Angeles, CA (US); Wange Lu, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 14/514,223

(22) Filed: Oct. 14, 2014

(65) Prior Publication Data
US 2015/0105327 A1    Apr. 16, 2015

Related U.S. Application Data

(60) Provisional application No. 61/891,220, filed on Oct. 15, 2013.

(51) Int. Cl.
| | |
|---|---|
| *A61K 38/00* | (2006.01) |
| *C07D 495/04* | (2006.01) |
| *C07K 14/47* | (2006.01) |
| *C07K 7/06* | (2006.01) |
| *C07K 7/08* | (2006.01) |
| *C12N 15/113* | (2010.01) |
| *G01N 33/50* | (2006.01) |
| *C12Q 1/48* | (2006.01) |
| *G01N 33/574* | (2006.01) |

(52) U.S. Cl.
CPC ................. *C07K 14/47* (2013.01); *A61K 38/00* (2013.01); *C07D 495/04* (2013.01); *C07K 7/06* (2013.01); *C07K 7/08* (2013.01); *C12N 15/1137* (2013.01); *C12Q 1/485* (2013.01); *G01N 33/5011* (2013.01); *G01N 33/57484* (2013.01); *C12N 2310/14* (2013.01); *G01N 2500/04* (2013.01); *G01N 2800/52* (2013.01)

(58) Field of Classification Search
CPC ...... A61K 38/00; C07D 495/04; C07K 14/47; C07K 7/06; C07K 7/08; C12N 15/1137; C12N 2310/14; C12Q 1/485; G01N 2500/04; G01N 2800/52; G01N 33/5011; G01N 33/57484

See application file for complete search history.

(56) References Cited

U.S. PATENT DOCUMENTS

2007/0232661 A1* 10/2007 Beachy ................ C07D 209/40
                                                                        514/331

OTHER PUBLICATIONS

International Search Report and Written Opinion (ISA/US) for International Application No. PCT/US2014/060529, mailed Apr. 29, 2015, 13 pages.
Kyei et al. (2015) "Cyclin L2 is a Critical HIB Dependency Factor in Macrophages that Controls SAMHD1 Abundance", Cell Host & Microbe 17, 98-106, Jan. 14, 2015.

(Continued)

*Primary Examiner* — Valerie Rodriguez-Garcia
(74) *Attorney, Agent, or Firm* — Foley & Lardner LLP; Antoinette F. Konski

(57) ABSTRACT

This disclosure provides methods and compositions to inhibit or suppress tumor growth or to treat cancer by inhibiting VprBP kinase activity. Also provided are methods of determining the effectiveness of the methods and compositions to inhibit or suppress tumor growth or to treat cancer by inhibiting VprBP kinase activity, methods for detecting a cancer, and methods for screening potential agents that inhibit VprBP kinase activity.

7 Claims, 27 Drawing Sheets

(56) References Cited

OTHER PUBLICATIONS

Ong et al. (2011) "Vipirinin, a Coumarin-based HIV-1 Vpr Inhibitor, Interacts with a Hydrophobic Region of VPR", J Biological Chemistry, vol. 286, No. 16, pp. 14049-14056, Apr. 22, 2011.

Rouzic et al. (2007) "HIV1 Vpr Arrests the Cell Cycle by Recruiting DCAF1/VprBP, a Receptor of the Cul4-DDB1 Ubiquitin Ligase", Cell Cycle 6:2, 182-185, Jan. 15, 2007.

Wang et al. (2012) "Autophagy negatively regulates cancer cell proliferation via selectively targeting VPRBP", Clinical Science (2013) 124, 203-214, Sep. 11, 2012.

* cited by examiner

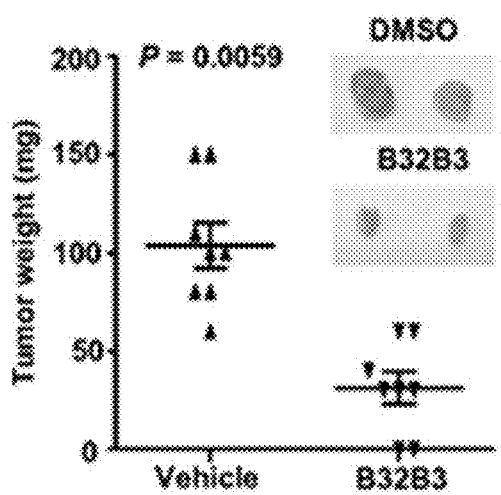
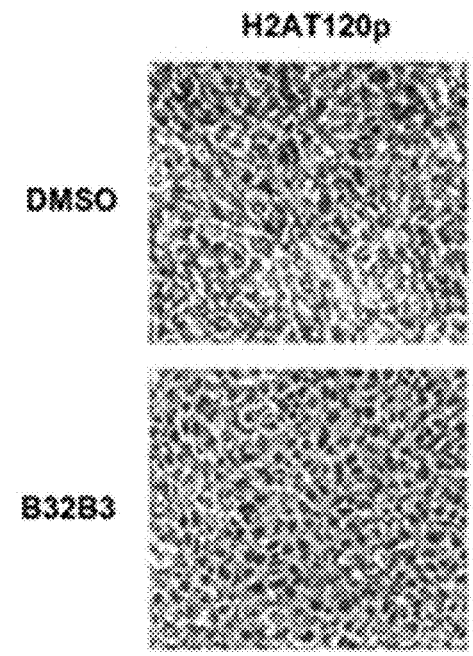
FIG. 4G
FIG. 4H
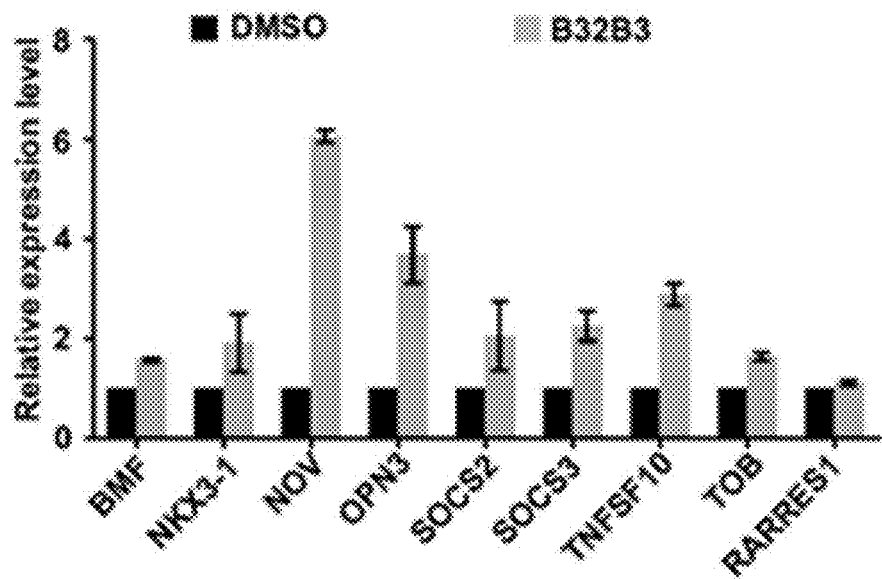
FIG. 4I

SEQUENCE LISTING

<160> NUMBER OF SEQ ID NOS: 81

<210> SEQ ID NO 1
<211> LENGTH: 21
<212> TYPE: DNA
<213> ORGANISM: Homo sapiens

<400> SEQUENCE: 1
cgagaaactg agtcaaatga a     21

<210> SEQ ID NO 2
<211> LENGTH: 19
<212> TYPE: DNA
<213> ORGANISM: Homo sapiens

<400> SEQUENCE: 2
aatcacagag tatcttaga     19

<210> SEQ ID NO 3
<211> LENGTH: 21
<212> TYPE: DNA
<213> ORGANISM: Homo sapiens

<400> SEQUENCE: 3
cgaggttaat ccagcacgta t     21

<210> SEQ ID NO 4
<211> LENGTH: 20
<212> TYPE: PRT
<213> ORGANISM: Homo sapiens

<400> SEQUENCE: 4

Gln Pro Leu Arg Thr Tyr Ser Thr Gly Leu Leu Gly Gly Ala Met Glu
1               5                   10                  15

Asn Gln Asp Ile
            20

<210> SEQ ID NO 5
<211> LENGTH: 17
<212> TYPE: PRT
<213> ORGANISM: Homo sapiens

<400> SEQUENCE: 5

Glu Val Ala Leu Arg Gln Glu Asn Lys Arg Pro Ser Pro Arg Lys Leu
1               5                   10                  15

Ser

<210> SEQ ID NO 6
<211> LENGTH: 39
<212> TYPE: PRT
<213> ORGANISM: Homo sapiens

<400> SEQUENCE: 6

```
Asp Pro Asp Arg Met Phe Val Glu Leu Ser Asn Ser Ser Trp Ser Glu
1               5                   10                  15

Met Ser Pro Trp Val Ile Gly Thr Asn Tyr Thr Leu Tyr Pro Met Thr
            20                  25                  30

Pro Ala Ile Glu Gln Arg Leu
        35

<210> SEQ ID NO 7
<211> LENGTH: 11
<212> TYPE: PRT
<213> ORGANISM: Homo sapiens

<400> SEQUENCE: 7

Tyr Ile Asp Leu Lys Gln Thr Asn Asp Val Leu
1               5                   10

<210> SEQ ID NO 8
<211> LENGTH: 6
<212> TYPE: PRT
<213> ORGANISM: Homo sapiens

<400> SEQUENCE: 8

Phe Ala Thr Glu Phe Val
1               5

<210> SEQ ID NO 9
<211> LENGTH: 9
<212> TYPE: PRT
<213> ORGANISM: Homo sapiens

<400> SEQUENCE: 9

Lys Leu Leu Glu Ile Pro Arg Pro Ser
1               5

<210> SEQ ID NO 10
<211> LENGTH: 9
<212> TYPE: PRT
<213> ORGANISM: Homo sapiens

<400> SEQUENCE: 10

Gln Asp Ala Met Glu Arg Val Cys Met
1               5

<210> SEQ ID NO 11
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Thr Ala Arg Lys Ser Thr Gly Gly Lys Ala Pro Arg Lys Gln Leu
1               5                   10                  15

Ala Thr Lys Ala Ala Arg Lys Ser Lys Arg Arg Gln Arg Arg Arg
            20                  25                  30

<210> SEQ ID NO 12
<211> LENGTH: 23
<212> TYPE: PRT
<213> ORGANISM: Homo sapiens

<400> SEQUENCE: 12
```

```
Gln Thr Ala Arg Lys Ser Thr Gly Gly Lys Ala Pro Arg Lys Gln Leu
1               5                   10                  15

Ala Thr Lys Ala Ala Arg Lys
            20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctcagccgac ttcagctctt                                             20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agccagcatt gccataaaag                                             20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agaaaggcac ttgggtctt                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tccgtgagct tgaggttctt                                             20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acgagctttt gtctccgaaa                                             20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 18
acaccagaca gcatgagcag                                            20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gatccctttt gcagcttctg                                            20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tttggaccca ttggttttgt                                            20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aaaagaggca ccagaaggaa                                            20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtccgcttat ccttgcacat                                            20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gccacctact gaaccctcct                                            20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 24
acggtcttcc gacagagatg                                                    20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ttcacagtgc tcctgcagtc                                                    20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acggagttgc cacttgactt                                                    20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggtgaaaagg gaccagtgaa                                                    20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tggagagctg gacactgatg                                                    20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcaccagtgt tgaagtgtgg                                                    20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
```
ggcatgcttg tcatctctca                                               20

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gccctaagga gagcagcac                                                19

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ttcgctgtag attggcactg                                               20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctgctcatgc tgtctggtgt                                               20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agctgcagga gaagaggtca                                               20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tagcttgcac aaaccctgtg                                               20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tgtggttgca caatccctaa                                              20

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gaaggtgccc agccagtg                                                18

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gcctgctcta gccattgtg                                               19

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
caggactcca ttcctgtggt                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ggtttcgtgc cttgttgagt                                              20

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gaaacggggt tggctgtag                                               19

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gtcgcaatac acaggcttca                                              20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
atcctcgagg cttttgtgtg                                          20

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tcccccgtta acgtttaatt t                                        21

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aggatctggg gagaaagagc                                          20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gggtcatgag agaagggtca                                          20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ccggaaattc tctcctgcta                                          20

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ggagagctcg aggtggaac                                           19

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ctctcgtcgc gctttgtct                                                19

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ggagcaggga gtccaagtc                                                19

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
atggtcaccc acagcaagtt                                               20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gctgcacatt ggactcaaaa                                               20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
aaaattagct gggcatggtg                                               20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
aacctccacc tcccagattc                                               20

```
<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gggacagttg caggttcaat                                                20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ggagcactgt gaagatcacg                                                20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
atccaaaggg actggagctt                                                20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gctgcacatt ggactcaaaa                                                20

<210> SEQ ID NO 59
<211> LENGTH: 2
<212> TYPE: PRT
<213> ORGANISM: Homo sapiens

<400> SEQUENCE: 59

Ser Gly
1

<210> SEQ ID NO 60
<211> LENGTH: 14
<212> TYPE: PRT
<213> ORGANISM: Homo sapiens

<400> SEQUENCE: 60

Lys Leu Val Arg Lys Ile Gly Ser Gly Ser Phe Gly Asp Ile
1               5                   10

<210> SEQ ID NO 61
<211> LENGTH: 17
<212> TYPE: PRT
<213> ORGANISM: Homo sapiens
```

```
<400> SEQUENCE: 61

Glu Val Ala Val His Leu Glu Ser Gln Lys Ala Arg His Pro Gln Leu
1               5                   10                  15

Leu

<210> SEQ ID NO 62
<211> LENGTH: 2
<212> TYPE: PRT
<213> ORGANISM: Homo sapiens

<400> SEQUENCE: 62

Tyr Gly
1

<210> SEQ ID NO 63
<211> LENGTH: 25
<212> TYPE: PRT
<213> ORGANISM: Homo sapiens

<400> SEQUENCE: 63

Asp Tyr Asn Val Leu Val Met Asp Leu Leu Gly Pro Ser Leu Glu Asp
1               5                   10                  15

Leu Phe Asn Phe Cys Ser Arg Arg Phe
            20                  25

<210> SEQ ID NO 64
<211> LENGTH: 11
<212> TYPE: PRT
<213> ORGANISM: Homo sapiens

<400> SEQUENCE: 64

His Arg Asp Ile Lys Pro Asp Asn Phe Leu Met
1               5                   10

<210> SEQ ID NO 65
<211> LENGTH: 6
<212> TYPE: PRT
<213> ORGANISM: Homo sapiens

<400> SEQUENCE: 65

Phe Leu Ile Asp Phe Gly
1               5

<210> SEQ ID NO 66
<211> LENGTH: 8
<212> TYPE: PRT
<213> ORGANISM: Homo sapiens

<400> SEQUENCE: 66

Pro Tyr Arg Glu Asp Lys Asn Leu
1               5

<210> SEQ ID NO 67
<211> LENGTH: 9
<212> TYPE: PRT
<213> ORGANISM: Homo sapiens

<400> SEQUENCE: 67

Arg Asp Asp Met Glu Ser Leu Gly Tyr
1               5

<210> SEQ ID NO 68
<211> LENGTH: 21
```

<212> TYPE: PRT
<213> ORGANISM: Homo sapiens

<400> SEQUENCE: 68

Tyr Ile Pro Asp Lys Leu Gly Lys Gly Gly Phe Gly Gln Val Trp
1               5                   10                  15

Leu Gly Arg Arg Val
            20

<210> SEQ ID NO 69
<211> LENGTH: 19
<212> TYPE: PRT
<213> ORGANISM: Homo sapiens

<400> SEQUENCE: 69

Gln Val Ala Leu His Phe Glu His Lys Ser Ser Lys Gly Cys Ala Ala
1               5                   10                  15

Gly Pro Pro

<210> SEQ ID NO 70
<211> LENGTH: 25
<212> TYPE: PRT
<213> ORGANISM: Homo sapiens

<400> SEQUENCE: 70

Asp Phe Tyr Ile Met Val Met Asp Leu Leu Gly Pro Ser Leu Trp Asp
1               5                   10                  15

Val Trp Asn Gln Gln Gly Gln Arg Leu
            20                  25

<210> SEQ ID NO 71
<211> LENGTH: 11
<212> TYPE: PRT
<213> ORGANISM: Homo sapiens

<400> SEQUENCE: 71

His Gly Asp Ile Lys Pro Glu Asn Phe Leu Leu
1               5                   10

<210> SEQ ID NO 72
<211> LENGTH: 6
<212> TYPE: PRT
<213> ORGANISM: Homo sapiens

<400> SEQUENCE: 72

Tyr Leu Val Asp Leu Gly
1               5

<210> SEQ ID NO 73
<211> LENGTH: 7
<212> TYPE: PRT
<213> ORGANISM: Homo sapiens

<400> SEQUENCE: 73

Lys Tyr Asp Gln Arg Pro Asp
1               5

<210> SEQ ID NO 74
<211> LENGTH: 9
<212> TYPE: PRT
<213> ORGANISM: Homo sapiens

<400> SEQUENCE: 74

Arg Asp Asp Leu Glu Ser Leu Ala Tyr
1               5

<210> SEQ ID NO 75
<211> LENGTH: 5
<212> TYPE: PRT
<213> ORGANISM: Homo sapiens

<400> SEQUENCE: 75

Ser Gly Arg Gly Lys
1               5

<210> SEQ ID NO 76
<211> LENGTH: 9
<212> TYPE: PRT
<213> ORGANISM: Homo sapiens

<400> SEQUENCE: 76

Ala Lys Ala Lys Thr Arg Ser Ser Arg
1               5

<210> SEQ ID NO 77
<211> LENGTH: 5
<212> TYPE: PRT
<213> ORGANISM: Homo sapiens

<400> SEQUENCE: 77

Thr Ile Ala Gln Gly
1               5

<210> SEQ ID NO 78
<211> LENGTH: 13
<212> TYPE: PRT
<213> ORGANISM: Homo sapiens

<400> SEQUENCE: 78

Pro Lys Lys Thr Glu Ser His His Lys Ala Lys Gly Lys
1               5                   10

<210> SEQ ID NO 79
<211> LENGTH: 27
<212> TYPE: PRT
<213> ORGANISM: Homo sapiens

<400> SEQUENCE: 79

Ser Tyr Asn Gln Gln Ala Met Glu Arg Val Cys Met Met Pro His Asn
1               5                   10                  15

Val Leu Ser Asp Val Val Asn Tyr Thr Leu Trp
            20                  25

<210> SEQ ID NO 80
<211> LENGTH: 24
<212> TYPE: PRT
<213> ORGANISM: Homo sapiens

<400> SEQUENCE: 80

Gln Ser Arg Arg Asp Asp Met Glu Ser Lys Gly Tyr Val Leu Met Tyr
1               5                   10                  15

Phe Asn Arg Thr Ser Leu Pro Trp
            20

<210> SEQ ID NO 81
<211> LENGTH: 24
<212> TYPE: PRT

```
<213> ORGANISM: Homo sapiens

<400> SEQUENCE: 81

Ser Ser Arg Arg Asp Asp Leu Glu Ser Leu Ala Tyr Thr Leu Ile Phe
1               5                   10                  15

Leu Leu Lys Gly Arg Leu Pro Trp
            20
```

COMPOSITIONS AND METHODS FOR THE TREATMENT OF VPRBP-RELATED CANCERS

CROSS-REFERENCE TO RELATED APPLICATION

This application claims priority under 35 U.S.C. §119(e) to U.S. Provisional Application No. 61/891,220, filed Oct. 15, 2013, the entire content of which is hereby incorporated by reference into the present disclosure.

STATEMENT OF GOVERNMENT SUPPORT

This invention was made with government support under NIH Grant GM84209 awarded by the National Institutes of Health. Accordingly, the government has certain rights in the invention.

SEQUENCE LISTING

The instant application contains a Sequence Listing which has been submitted electronically in ASCII format and is hereby incorporated by reference in its entirety. Said ASCII copy, created on Dec. 3, 2014, is named 064189-7081_SL.txt and is 17,329 bytes in size.

TECHNICAL FIELD

This invention generally relates to the methods and compositions for treating cancer and inhibiting the growth of a cancer cell or a tumor.

BACKGROUND

Genomic DNA in human cells is hierarchically packaged by histones to form a highly repressive structure of chromatin. The basic unit of chromatin is the nucleosome, which consists of 147-bp of negatively supercoiled DNA wrapped a core histone octamer containing pairs of each of the four core histones, H2A, H2B, H3 and H4. The dynamic posttranslational modifications of histone N-terminal and C-terminal domains (called histone "tails"), which extend away from the nucleosome, govern the structural diversity of chromatin and the accessibility of DNA, thus representing an important molecular mechanism underlying regulation of gene expression. VprBP is a nuclear protein that can interact with HIV viral protein R and the Cullin 4-DDB1 ubiquitin ligase complex. Its cellular function has been studied mainly with respect to its role in regulating Cullin 4 E3 ubiquitin ligase activity and cell cycle progression. However, subsequent studies, predominantly from Inventor's laboratory, have revealed that VprBP stably binds to promoter nucleosomes and that this association represses p53-mediated chromatin transcription (Mol Cell Biol 32, 783-796). The C-terminal region of VprBP has an ability to interact with H3 N-terminal tails protruding from nucleosomes and is critical for the observed functions of VprBP. Overexpression and mutations of VprBP have been detected in bladder/breast/prostate cancer cells supporting the idea that it possesses oncogenic properties.

SUMMARY

In one aspect, this technology provides methods and compositions for treating cancer by inhibiting VprBP kinase activity.

In another aspect, this technology provides methods and compositions for activating tumor suppression by inhibiting VprBP kinase activity.

In still another aspect, this technology provides methods and compositions for inhibiting H2AT120p by inhibiting VprBP kinase activity.

In some embodiments, the VprBP kinase activity is inhibited by an inhibitor of VprBP. In one aspect, the inhibitor comprises, or alternatively consists essentially of, or yet further consists of, QTARKSTGGKAPRKQLATKAARK (SEQ ID NO: 12) or comprises, or alternatively consists essentially of, or yet further consists of, a synthetic peptide comprising a HIV1 TAT sequence and the H3 N-terminal tail domain which corresponds to amino acids 5-27 (QTARK-STGGKAPRKQLATKAARK (human histone H3 N-terminal tail corresponding to amino acids 5-27)-RKKRRQRRR (HIV1 TAT sequence)) (SEQ ID NO: 11), and sequences having at least 80% amino acid sequence identity to each thereof and having the same or similar biological activity. Since the regulation of H2AT120 phosphorylation is important in the control of cell growth and the establishment and maintenance of gene silencing, the present invention should make it possible to detect and regulate VprBP dysfunction related to cancer development. In addition, the invention provides a method of reducing H2AT120 phosphorylation by using histone H3 tail peptides which block VprBP kinase activity and therefore reduce VprBP carcinogenic potential in cancer cells.

In some embodiments, the VprBP kinase activity is inhibited by RNA interference. In some embodiments, the RNAi comprises, or alternatively consists essentially of, or yet further consists of, one or more polynucleotide of the group VprBP shRNA1 (SEQ ID NO: 1: 5'-CGAGAAACTGAGT-CAAATGAA-3'), VprBP shRNA2 (SEQ ID NO: 2: 5'-AAT-CACAGAGTATCTTAGA-3') or Bub1 shRNA (SEQ ID NO: 3:5'-CGAGGTTAATCCAGCACGTAT-3'), or an equivalent of each thereof.

In some embodiments, the VprBP inhibitor is a small molecule inhibitor of VprBP, such as a compound of the formula:

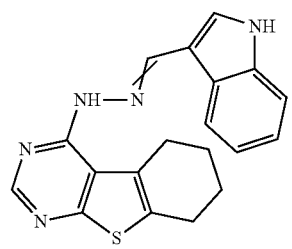 [SMILES: c1ccc2c(CNNc3ncnc4sc5c(c34)CCCC5)c[nH]c2c1]

or a pharmaceutically acceptable salt thereof or a solvate of the compound or the salt thereof.

In still another aspect, this technology provides a method for treating or inhibiting cancer comprising administering to a patient in need thereof an effective amount of a compound of the formula:

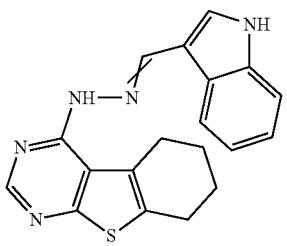 [SMILES: c1ccc2c(CNNc3ncnc4sc5c(c34)CCCC5)c[nH]c2c1]

or a pharmaceutically acceptable salt thereof or a solvate of the compound or the salt thereof, or an RNAi, wherein the RNAi comprises, or alternatively consists essentially of, or yet further consists of, one or more polynucleotide of the group VprBP shRNA1 (SEQ ID NO: 1: 5'-CGAGAAACT-GAGTCAAATGAA-3'), VprBP shRNA2 (SEQ ID NO: 2: 5'-AATCACAGAGTATCTTAGA-3') Bub1 shRNA (SEQ ID NO: 3:5'-CGAGGTTAATCCAGCACGTAT-3'), or an equivalent of each thereof.

In still another aspect, this technology provides a method of detecting a VprBP-related cancer in a patient, comprising, or alternatively consisting essentially thereof, or yet further consisting of, determining the presence of VprBP in a sample of the patient, wherein the presence of VprBP is indicative of a cancer in the patient.

In some embodiments, an overexpression of VprBP is indicative of a cancer in the patient. In some embodiments, overexpression of VprBP means that the VprBP level in the sample is higher than the average or range of VprBP level of healthy individuals or individuals that do not have the cancer.

In some embodiments, the cancer or tumor is a solid tumor. In some embodiments, the cancer is bladder, breast or prostate cancer.

In still another aspect, this technology provides a method for determining the effectiveness of treating or monitoring the treatment a cancer, e.g., a VprBP-related cancer, by VprBP inhibition, comprising determining the gene expression of a gene selected from Tables 2 and 3 in a sample of the patient before VprBP inhibition and in a sample of the patient after VprBP inhibition, wherein activation of a gene selected from Table 2 or repression of a gene selected from Table 3 is indicative of effectiveness of VprBP inhibition in treating the cancer in the patient.

Activation of a gene refers to an increase in the expression of the gene in the presence of VprBP inhibition as compared with the expression of the gene in the absence of VprBP inhibition. In some embodiments, activation of a gene selected from Table 2 means that at least 0.5 or more, or alternatively at least 1, or more fold change in gene expression of a gene selected from Table 2 is found. In some embodiments, activation of a gene selected from Table 2 means that at least 1.5, or alternatively at least a 2 fold change in gene expression of a gene selected from Table 2 is found. In some embodiments, activation of a gene selected from Table 2 means that at least 3 fold change in gene expression of a gene selected from Table 2 is found. In some embodiments, activation of a gene selected from Table 2 means that at least 4 fold change in gene expression of a gene selected from Table 2 is found. In some embodiments, activation of a gene selected from Table 2 means that at least 5 fold change in gene expression of a gene selected from Table 2 is found. In some embodiments, the gene is one or more gene selected from LOC100008589, IL11, LOC100132564, RMRP, SCARNA18, LOC100008588, CD24 SCARNA11, LOC100133565, SLC22A18AS, Hs.543887, KIAA1644, MIR1978, NOV, SCARNA14, SCARNA8, C6orf48 and SCARNA16, or a combination thereof. In some embodiments, the gene is selected from LOC100008589, IL11, LOC100132564, RMRP, SCARNA18, LOC100008588, CD24 and SCARNA11, or a combination thereof.

Repression of a gene refers to a decrease in the expression of the gene in the presence of VprBP inhibition as compared with the expression of the gene in the absence of VprBP inhibition. In some embodiments, repression of a gene selected from Table 3 means that at least −0.5 fold, or at least −1.0, or alternatively at least a −1.5 fold change in gene expression of a gene selected from Table 3 is found. In some embodiments, repression of a gene selected from Table 3 means that at least −2 fold change in gene expression of a gene selected from Table 3 is found. In some embodiments, repression of a gene selected from Table 2 means that at least −3 fold change in gene expression of a gene selected from Table 3 is found. In some embodiments, repression of a gene selected from Table 3 means that at least −4 fold change in gene expression of a gene selected from Table 3 is found. In some embodiments, the gene is one or more gene selected from SNORD13, CYP24A1, RASL10A, CCL20, IGFBP3, LCN2, SRPX, SYTL2, ERLIN2, SPP1, OPLAH, TMEM145, HLA-DMA, PCK2, ANG, RNASE4, KIF1B, GALNTL1, ACCN2, MAP1LC3A, LAMP3, KISS1R, DDIT4L and CLYBL, or a combination thereof. In some embodiments, the gene is selected from SNORD13, CYP24A1, RASL10A, CCL20 and IGFBP3, or a combination thereof.

In some embodiments, the cancer comprise, or alternatively consists essentially of, or yet further consists of, a solid tumor. In some embodiments, the cancer is bladder, breast or prostate cancer.

In some embodiments, the sample is bladder, breast or prostate sample.

In some embodiments, the sample is a tissue sample comprising and/or suspected of comprising cancer or tumor cells.

In some embodiments, the sample is a blood or plasma sample.

In still another aspect, this technology provides a composition for treating cancer or for activation of tumor suppressor function in a cell in need thereof, comprising, or alternatively consisting essentially of, or yet further consisting of, a carrier and one or more of an effective amount of a compound of the formula:

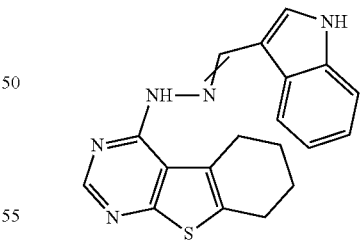

or a pharmaceutically acceptable salt, or a solvate of the compound or the salt thereof or an equivalent of each thereof, or a polynucleotide comprising, or alternatively consisting essentially of, or yet further consisting of, VprBP shRNA1 (SEQ ID NO: 1: 5'-CGAGAAACTGAGTCAAATGAA-3'), VprBP shRNA2 (SEQ ID NO: 2: 5'-AATCACAGAGTATCT-TAGA-3') Bub1 shRNA (SEQ ID NO: 3:5'-CGAGGT-TAATCCAGCACGTAT-3'), or an equivalent of each thereof.

In some embodiments, the effective amount of the compound is from about 1 mg/day to 10 g/day. In some embodiments, the effective amount of the compound is about 1 mg/day, about 10 mg/day, about 50 mg/day, about 100 mg/day, about 1 g/day, or about 10 g/day, or within any range between any two of these values (including endpoints). In some embodiments, the effective amount of the compound is from about 0.01 mg/kg to 100 mg/kg. In some embodiments, the effective amount of the compound is about 0.01 mg/kg, about 0.1 mg/kg, 1 mg/kg, about 10 mg/kg, about 50 mg/kg, or 100 mg/kg, or within any range between any two of these values (including endpoints).

In still another aspect, this technology provides a composition comprising, or alternatively consisting essentially of, or yet further consisting of, a carrier and a RNAi capable of inhibiting VprBP expression. In one aspect, the RNAi is present in the composition in an effective amount.

In some embodiments, the RNAi is selected from the group consisting of a polynucleotide comprising, or alternatively consisting essentially of, or yet further consisting of, a VprBP shRNA1 (SEQ ID NO: 1: 5'-CGAGAAACTGAGTCAAAT-GAA-3'), VprBP shRNA2 (SEQ ID NO: 2: 5'-AATCACA-GAGTATCTTAGA-3') and Bub1 shRNA (SEQ ID NO: 3:5'-CGAGGTTAATCCAGCACGTAT-3'), or an equivalent thereof.

In some embodiments, the effective amount of the compound is about 0.01 mg/kg, about 0.1 mg/kg, 1 mg/kg, about 10 mg/kg, about 50 mg/kg, or 100 mg/kg, or within any range between any two of these values (including endpoints).

In some embodiments, the carrier is a pharmaceutically acceptable carrier or an in situ device.

In some embodiments, the device is a catheter.

In still another aspect, this technology provides a screen to identify a potential therapeutic agent for inhibiting tumor growth or for tumor suppression, and in one aspect a VprBP-related tumor, comprising or alternatively consisting essentially of, or yet further consisting of, contacting a candidate agent with VprBP to initiate a kinase reaction, wherein the agent is a potential therapeutic agent if a reduction of kinase activity as compared to the kinase activity of VprBP in the absence of the agent is observed.

In some embodiments, the agent is a small molecule.

In some aspects of the above-noted embodiments, the patient is a non-human animal or a human patient. Non-human animals include, for example, simians, murines, such as, rats, mice, chinchilla, canine, equine, feline, leporids, such as rabbits, livestock, sport animals and pets.

In one aspect, the disclosure provides an isolated peptide, comprising, or alternatively consisting of, or yet further consisting essentially of, one or more of the sequence QTARK-STGGKAPRKQLATKAARK (SEQ ID NO: 12) or QTARK-STGGKAPRKQLATKAARK (human histone H3 N-terminal tail corresponding to amino acids 5-27)-RKKRRQRRR (HIV1 TAT sequence) (SEQ ID NO: 11), or an equivalent of each thereof, such as sequences having at least 80%, or alternatively at least 90% or alternatively at least 95% amino acid sequence identity and having the same or similar biological activity to competitively inhibit VprBP-medicated H2AT120 phosphorylation. In one aspect, the isolated peptide further comprises, or alternatively consists essentially of, or yet further consists of, a detectable label. Methods to recombinantly or chemically reproduce the isolated peptide are further provided herein.

Also provided herein is an isolated polynucleotide that encodes a peptide comprising or alternatively consisting of, or yet further consisting essentially of, the sequence QTARK-STGGKAPRKQLATKAARK (SEQ ID NO: 12) or QTARK-STGGKAPRKQLATKAARK (human histone H3 N-terminal tail corresponding to amino acids 5-27)-RKKRRQRRR (HIV1 TAT sequence) (SEQ ID NO: 11), or an equivalent of each thereof, such as sequences having at least 80%, or alternatively at least 90% or alternatively at least 95% amino acid sequence identity and having the same or similar biological activity to competitively inhibit VprBP-medicated H2AT120 phosphorylation. In one aspect, the polynucleotide hybridized under stringent conditions to the polynucleotide, or an equivalent thereof, or their compliments.

In still another aspect, this technology provides isolated, non-naturally occurring polynucleotide encoding VprBP or the polypeptides as disclosed herein, or a polynucleic acid which has at least 80%, 85%, 90% or 95% of sequence identity to a polynucleic acid encoding VprBP, or a fragment thereof. In one aspect, the non-naturally occurring polynucleotide comprises a cDNA or an isolated naturally occurring polynucleotide having attached thereto a non-naturally occurring element, such as a linker, a label or a non-naturally occurring polynucleotide.

In some embodiments, the cDNA is a cDNA of a polynucleic acid having a sequence encoding a polypeptide sequence comprising, or alternatively consisting essentially of, or yet further consisting of, a polynucleotide of the sequence: Q-PLRTYSTGLLGGAMENQDI (SEQ ID NO: 4), EVALRQENKRPSPRKLS (SEQ ID NO: 5), or both, or an equivalent of each thereof.

In some embodiments, the cDNA is a cDNA of a polynucleic acid comprising a sequence encoding a polypeptide sequence comprising, or alternatively consisting essentially of, or yet further consisting of, DPDRMFVELSNSSWSEM-SPWVIGTNYTLYPMTPAIEQRL (SEQ ID NO: 6), or an equivalent thereof.

In some embodiments, the cDNA is a cDNA of a polynucleic acid having a sequence encoding a polypeptide sequence comprising, or alternatively consisting essentially of, or yet further consisting of, YIDLKQTNDVL (SEQ ID NO: 7), FATEFV (SEQ ID NO: 8), KLLEIPRPS (SEQ ID NO: 9), or QDAMERVCM (SEQ ID NO: 10), or two or more of SEQ ID NO: 7 to SEQ ID NO: 10, or an equivalent of each thereof.

In some embodiments, the cDNA is a cDNA of a polynucleic acid having a sequence encoding a polypeptide sequence comprising, or alternatively consisting essentially of, or yet further consisting of, two or more of SEQ ID NO: 4 to SEQ ID NO: 10, or an equivalent of each thereof. In some embodiments, the cDNA is a cDNA of a polynucleic acid having a sequence encoding a polypeptide sequence comprising, or alternatively consisting essentially of, or yet further consisting of, all of SEQ ID NO: 4 to SEQ ID NO: 10, or an equivalent of each thereof.

Polynucleotides (such as cDNA or RNAi) as used herein can be combined with a vector or contained within a cell of delivery or expression. Any art recognized method for therapeutic delivery or expression of such are intended within the scope of this disclosure.

Kits are further provided which contain the compositions described herein and instructions for intended use.

BRIEF DESCRIPTION OF THE FIGURES

(FIG. 1A) Chromatin was prepared from human prostate cancer (DU145) and normal (MLC) cell lines and subjected to western blotting with the indicated antibodies. Ponceau S staining and b-actin served as loading controls in all western blot analyses in this study. Quantifications of the band intensities by densitometry are shown below the western blots, and similar results were obtained from two additional experiments. ac, acetylation; p, phosphorylation; me3, trimethylation. (FIG. 1B) DU145 cells were infected with lentiviruses expressing VprBP shRNA1 (lane 2) or nonspecific control shRNA (lane 1), and chromatin fractions were analyzed by western blotting as in (FIG. 1A). (FIG. 1C) Individual core histones were incubated with recombinant VprBP in the presence of [g-32P] ATP. The reactions were resolved by 15% SDS-PAGE and analyzed by autoradiography (upper panel) and Coomassie blue staining (lower panel). (FIG. 1D) VprBP contains the putative kinase domain in the N-terminal region, the L is homology motif in the central region, and the WD repeat and D/E-rich motif in the C-terminal region. Numbers denote amino acid positions. Sequence alignment of the putative kinase domain in VprBP (SEQ ID NOS 4-5, 59 and 6-10, respectively, in order of appearance) with the kinase domains of human CK1 (SEQ ID NOS 60-67, respectively, in order of appearance) and Mut9p (SEQ ID NOS 68-69, 62 and 70-74, respectively, in order of appearance) is shown in the lower panel. The boxed regions correspond to the conserved kinase subdomains I-III and V-IX. (FIG. 1E) Nucleosomes were reconstituted on a 207 bp 601 nt positioning sequence using recombinant histones and incubated with wild-type VprBP or the indicated mutants. H2A phosphorylation was detected by autoradiography. (FIG. 1F) Kinase assays were performed as in (FIG. 1E) but using nucleosomes containing wild-type, tailless, or mutant H2A (SEQ ID NOS 75-78, respectively, in order of appearance). The residues that were mutated are indicated at the top. The H2A mutations did not affect histone octamer and nucleosome formation during reconstitution (data not shown). (FIG. 1G) Nucleosomes containing H2A wild-type or T120A mutant were incubated with VprBP and ATP. H2AT120p was analyzed by western blotting with anti-H2AT120p antibody. See also FIG. 5.

(FIG. 2A) Tissue microarrays containing primary tumor and adjacent normal samples from cancer patients were subjected to immunohistochemistry with VprBP and H2AT120p antibodies. High-power magnifications are shown for six representative samples. Scale bars correspond to 50 mm. See also Table 1. (FIG. 2B) DU145 cells were depleted of VprBP and infected with lentiviruses expressing the VprBP wild-type (WT) or VprBP kinase-dead mutant K194R (KD). The levels of VprBP and H2AT120p were determined by western blotting. (FIG. 2C) VprBP-depleted DU145 cells were complemented with VprBP WT or KD, and cell proliferation was measured by MTT assay. Results represent the means±SD of three experiments performed in triplicate. (FIG. 2D) VprBP-depleted DU145 cells were infected with VprBP WT or KD as in (FIG. 2C), and the colonies grown up in soft agar were stained and counted. The y axis indicates the number of colonies with a diameter of >0.05 mm per view. Three independent experiments in triplicate wells were performed. Data represent the means±SD of three independent experiments. See also FIG. 6.

(FIG. 3A) Chromatin templates containing wild-type or T120-mutated H2A were transcribed in the presence of Gal4-VP16, p300+AcCoA, and/or VprBP as indicated above the panel. VprBP was added to the reaction before p300. The results shown are representative of three independent experiments. (FIG. 3B) Shown are scatterplots of the global gene expression patterns comparing VprBP-depleted DU145 cells with mock-depleted cells. Dots represent expression values for the genes with a change >1.7-fold in either of two independent experiments. (FIG. 3C) Clustering and heatmap representation of the genes upregulated upon VprBP depletion and related to cell death and proliferation. Yellow and blue indicate high and low expression, respectively. See also Tables 2 and 3. (FIG. 3D) RNA was isolated from VprBP-depleted DU145 cells as in (FIG. 3B) and subjected to real-time qRT-PCR using primers specific for the indicated genes and listed in Experimatal Procedures. Expression levels were normalized to b-actin level and shown relative to those of mock-depleted cells, and were arbitrarily assigned a value of 1. Data represent the means±SD of three independent experiments. (FIG. 3E) The levels of H2AT120p, H2A, VprBP, and H3 at the OPN3 gene were assessed in mock- and VprBP-depleted DU145 cells by ChIP analysis. Precipitation efficiencies were determined for promoter (P), transcription start site (TSS), and coding region (CR) by quantitative PCR (qPCR) with primers listed in Experimental Procedures. Quantitative results were averaged from three separate determinations. Results represent the means±SD of three independent experiments. See also FIG. 7.

FIGS. 4A-4J show discovery and characterization of a small-molecule VprBP inhibitor. (FIG. 4A) In vitro kinase assays were performed with recombinant H2A and VprBP in the presence of the indicated compounds (5 mM). The effects of the compounds were evaluated by western blotting with H2AT120p antibody. (FIG. 4B) DU145 cells were grown in the presence of the indicated concentrations of either B32B3 or B20H6 for 24 hr and immunoblotted with H2A and H2AT120p antibodies. (FIG. 4C) Molecular structure of B32B3. (FIG. 4D) DU145 cells were treated with DMSO or 0.5 mM B32B3 for 24 hr. The cellular levels of H2AT120p were assessed by immunostaining (FIG. 4E) DU145 cells were treated with increasing concentrations of B32B3 for 24 hr, and the colonies were counted 3 weeks after seeding the cells on soft agar. The data are the means of three independent experiments±SD. (FIG. 4F) Nude mice were implanted with 1 3 107 DU145 cells on the left flank. Five days after implantation, mice bearing established tumors were randomized into groups and treated with twice-weekly i.p. injections of either DMSO or B32B3 at a dose of 5 mg/kg (n=8 per group). Tumor volumes (mm3) were measured at the indicated time points and shown as mean tumor volumes±SEM. (FIG. 4G) Mice were killed at day 25 of the tumor growth, and the tumors were dissected and weighed. Mean tumor weights±SEM are shown, and the p value was calculated by unpaired Student's t test. (FIG. 4H) DU145 xenografts were excised from DMSO-treated and B32B3-treated mice, and were analyzed by immunohistochemistry. Representative view was photographed. (FIG. 4I) Relative mRNA levels of the VprBP target genes in DMSO-treated (black bars) and B32B3-treated (1 mM, gray bars) DU145 cells were determined by qRT-PCR. Data represent the means±SD of three independent experiments. (FIG. 4J) DU145 cells exposed to DMSO or 1 mM B32B3 were subject to ChIP analysis using the indicated antibodies. The data are the means of three independent experiments±SD. See also FIG. 8.

(FIG. 5A) Chromatin was isolated from human bladder (LD611) and breast (MDA-MB231) cancer cell lines and their normal counterparts (Urotsa and MCF-10-2A). The levels of the indicated histone modifications were assessed by Western blotting as in FIG. 1A. (FIG. 5B) LD611 bladder and MDA-MB231 breast cancer cell lines were infected with a VprBP shRNA and examined for the indicated histone modifications by Western blotting. (FIG. 5C) Recombinant VprBP proteins were expressed in Sf9 cells and purified as described under Experimental Procedures. The purity of the proteins used in this study was confirmed by SDS-PAGE and subsequent silver staining (FIG. 5D) The purity of the recombinant VprBP wild type purified in (FIG. 5C) was determined by mass spectrometry. (FIG. 5E) Individual core histones were incubated with VprBP in the presence of [3H]-AcCoA or [3H]-SAM, and their modifications were determined by autoradiography. As positive controls, p300 (acetylating all four core histones) and Set7 (methylating H3K4) were included in the assays. (FIG. 5F) In vitro kinase assays were performed as in FIG. 1C, but using reconstituted nucleosomes containing untagged H2A (lanes 1 and 2) or Flag-tagged H2A (lanes 3 and 4). (FIG. 5G) Mononucleosomes were immobilized on streptavidin-agarose beads and incubated with VprBP in the presence of 10 mM ATP. After extensive washing, intranucleosomal H2AT120p was accessed by immunoblotting with H2A and H2AT120p antibodies. (FIG. 5H) In vitro kinase assays were performed with recombinant H2A and endogenous VprBP immunoprecipitated from DU145 cells. (FIG. 5I) The recombinant VprBP (5 μg) was separated on an 8% SDS-PAGE gel, denatured with 6M guanidine HCl for 1 h and renatured for 16 h. To detect autophosphorylation of VprBP, the gel was soaked in kinase buffer in the presence of [γ-32P]ATP (20 Ci/ml) for 1 h, washed stringently for 2 h, dried, and visualized by autoradiography. (FIG. 5J) Wild type and mutant VprBP proteins were run on a denaturing gel, refolded, and subjected to in situ kinase assay as in FIG. 5I. (FIG. 5K) CD values were determined using 1 μM VprBP proteins in the range of 200-260 nm. CD spectra are the average of 20 measurements. (FIG. 5L) DU145 cells were infected with Bub1 shRNA, and the levels of H2AT120p were determined by Western blot analysis of cell extracts. (FIG. 5M) Whole cell extract were prepared in MLC and DU145 cells, and total Bub1 expression levels were analyzed by Western blotting.

(FIG. 6A) DU145 cancer cells were depleted of VprBP using another shRNA, as confirmed by Western blotting. (FIG. 6B) DU145 cells depleted of VprBP in (FIG. 6A) were subjected to MTT assays over a period of 5 days. Results are the means±S.D. of three experiments performed in triplicate. (FIG. 6C) DU145 cells depleted of VprBP in (FIG. 6A) were subjected to colony formation assays as described in FIG. 2D. Data represent the means±S.D. of three independent experiments. (FIG. 6D) MLC cells were infected with lentiviruses expressing VprBP, and the levels of VprBP and H2AT120p were assessed by Western blotting. (FIG. 6E) VprBP was overexpressed in MLC cells as in (FIG. 6D), and its effects on cell proliferation were determined by MTT assay over a period of 5 days. Average and standard deviation are shown for three independent experiments. (FIG. 6F) Colony formation assays were carried out as in (FIG. 6C), but using MLC cells overexpressing VprBP. Average and standard deviation of three independent experiments are shown.

(FIG. 7A) In vitro transcription assays were performed using chromatin templates containing wild type or T120-mutated H2A as in FIG. 3A, but in the absence of ATP. (FIG. 7B) The 292 genes identified as being upregulated upon VprBP knockdown from the microarray analysis were subjected to functional enrichment analysis using DAVID. The blue and red bars represent the number of enriched genes and p-values for the enrichment, respectively. (FIG. 7C) ChIP assays of four VprBP target genes (NOV, SOCS2, SOCS3 and TNFSF10) and one control gene (RARRES1) were performed as in FIG. 3E using the indicated antibodies. The precipitated DNA was quantified by qPCR with the primers listed in Experimental Procedures. Results represent the means±S.D. of three independent experiments.

(FIG. 8A) DU145 cells were infected with mock lentiviruse, VprBP-expressing shRNA lentivirus or Flag-VprBP-expressing lentivirus, and treated with the indicated concentrations of B32B3 for 24 h. Changes in H2AT120p as the results of B32B3 treatment were determined by the quantitative estimates of Western band intensity. Results represent the means±S.D. of three independent experiments. (FIG. 8B) DU145 cells were treated with the indicated concentrations of B32B3 and B20H6 for 72 h. Cell viability was measured by the MTT assay and was normalized to cells not exposed to the compounds. Data represent the means±S.D. of three independent experiments. (FIG. 8C) MLC cells were grown in the presence of the indicated concentrations of B32B2 for 24 h, and subjected to immunoblotting with H2AT120p and H2A antibodies. (FIG. 8D) MLC cells were treated with B32B3 at the indicated doses for 24 h, and cell viability was assessed by MTT assay. Average and standard deviation of three independent experiments are shown. (FIG. 8E) VprBP-mediated H2AT120p was analyzed in the presence of increasing concentrations of ATP and B32B3. (FIG. 8F) Body weights of vehicle or B32B3-treated mice were monitored during the treatment period. Mean body weights±S.E.M. are shown. (FIG. 8G) B32B3 was spiked into the indicated blank plasma to a concentration of 10 μM. The stability of B32B3 in plasma was determined by LC-MS/MS at the indicated time points. Results are shown as the mean of three independent experiments±S.D. (FIG. 8H) B32B3 was administered to mice (n=5) at a dose of 5 mg/kg. Blood samples were collected at the indicated time points, and the concentration of B32B3 in plasma was analyzed by HPLC coupled mass spectrophotometry. The data are shown as the mean±S.D. (FIG. 8I) B32B3-treated DU145 cells were subjected to ChIP analysis as in FIG. 4I using indicated antibodies. Average and standard deviation are shown for three independent experiments.

FIG. 9 discloses VprBP as SEQ ID NOS 4-5, 59, 6-9 and 79, respectively, in order of appearance, CK1 as SEQ ID NOS 60-66 and 80, respectively, in order of appearance and Mut9p as SEQ ID NOS 68-69, 62, 70-73 and 81, respectively, in order of appearance.

DETAILED DESCRIPTION

Figure 1A:
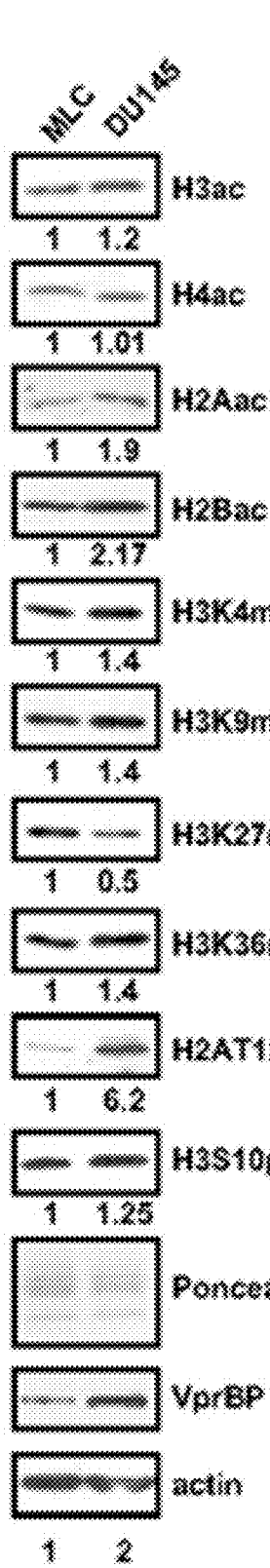
FIGS. 1A-1G show VprBP phosphorylates histone H2A at T120.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are now described. All technical and patent publications cited herein are incorporated herein by reference in their entirety. Nothing herein is to be construed as an admission that the invention is not entitled to antedate such disclosure by virtue of prior invention.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

The term "about" when used with numerical designations, e.g., pH, temperature, time, amount, concentration and molecular weight, including ranges, refers to approximations which are varied (+) or (−) by increments of 1.0 or 0.1, as appropriate, or alternatively by a variation of +/−15%, or alternatively 10%, or alternatively 5% or alternatively 2%.

As used in the specification and claims, the singular form "a", "an" and "the" include plural references unless the context clearly dictates otherwise. For example, the term "a polypeptide" includes a plurality of polypeptides, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention. Embodiments defined by each of these transition terms are within the scope of this invention.

The term "VprBP" refers to a nuclear protein that can interact with HIV viral protein R and Cullin 4-DDB1 ubiquitin ligase complex which is reported in Li, W. et al. ((2010) Cell 140:477-490), including the wild type VprBP and mutated VprBP, such as those described in the Experimental section.

The term "VprBP kinase activity" refers to VprBP's activity of phosphorylating another protein. In some embodiments, the protein that is phosphorylated by VprBP is a histone, a protein found in eukaryotic cell nuclei that packages and orders the DNA into structural units called nucleosomes, described in, for example, Suganuma, T. et al. ((2011) Annu Rev. Biochem. 80:473-499) and Banerjee, T. et al. ((2011) Mol. Cell. Biol. 31:4858-4873). In some embodiments, the protein that is phosphorylated by VprBP is histone H2A at, for example, threonine 120.

The term "VprBR-related cancer" intends a cancer or tumor that is caused by in whole or in part by the misregulation of VprBP phosphorylation of a histone.

The term "H2AT120p" refers to histone H2A phosphorylated at threonine 120.

The term "isolated" as used herein with respect to nucleic acids, such as DNA or RNA, refers to molecules separated from other DNAs or RNAs, respectively that are present in the natural source of the macromolecule. The term "isolated peptide fragment" is meant to include peptide fragments which are not naturally occurring as fragments and would not be found in the natural state. The term "isolated" is also used herein to refer to polypeptides and proteins that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, protein, antibody or fragment(s) thereof, which are normally associated in nature. For example, an isolated cell is a cell that is separated form tissue or cells of dissimilar phenotype or genotype. As is apparent to those of skill in the art, a non-naturally occurring polynucleotide, peptide, polypeptide, protein, antibody or fragment(s) thereof, does not require "isolation" to distinguish it from its naturally occurring counterpart.

The term "purified" refers to a composition being substantially free from contaminants. With respect to polynucleotides and polypeptides, purified intends the composition being substantially free from contamination from polynucleotides or polypeptides with different sequences. In certain embodiments, it also refers to polynucleotides and polypeptides substantially free from cell debris or cell culture media.

The term "recombinant" refers to, in one aspect, a form of artificial DNA that is created by combining two or more sequences that would not normally occur in their natural environment. In another aspect, "recombinant" intends isolated DNA that is replicated in an artificial system. A recombinant protein is a protein that is derived from recombinant DNA.

The term "protein", "peptide" and "polypeptide" are used interchangeably and in their broadest sense refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

"Homology" or "identity" or "similarity" refers to two nucleic acid molecules that hybridize under stringent conditions to the reference polynucleotide or its complement.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

As used herein, the terms "treat", "treating," or "treatment" and the like are used herein to mean obtaining a desired pharmacologic and/or physiologic effect. The effect may be prophylactic in terms of completely or partially preventing a disorder or sign or symptom thereof and/or may be therapeutic in terms of a partial or complete cure for a disorder and/or adverse effect attributable to the disorder.

To "prevent" intends to prevent a disorder or effect in vitro or in vivo in a system or subject that is predisposed to the disorder.

The term "tumor suppression" refers to slowing down the growth of a tumor, stopping the growth of a tumor or reducing the size of existing tumor.

The term "inhibiting H2AT120p" refers to inhibiting the phosphorylation of histone H2A on threonine 120 and/or inhibiting the activity of histone H2A phosphorylated on threonine 120.

The term "VprBP inhibitor" refers to a compound or other agent such as RNAi that reduces the activity of VprBP. In some embodiments, the compound inhibits VprBP with a half maximal inhibitory concentration ($IC_{50}$) value of no more than about 10 µM, or no more than about 5 µM, or no more than about 1 µM.

The term "small molecule VprBP inhibitor" refers to a VprBP inhibitor with a molecular weight of no more than about 1,500 Daltons, or no more than about 1,000 Daltons, or no more than about 900 Daltons.

In some embodiments, the small molecule inhibitor of VprBP is B32B3, a compound of the formula:

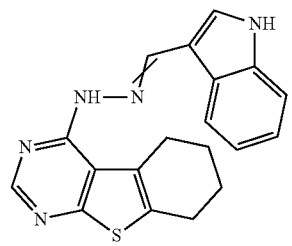 [SMILES: c1ccc2c(CNNc3ncnc4sc5c(c34)CCCC5)c[nH]c2c1]

or a pharmaceutically acceptable salt thereof or a solvate of the compound or the salt thereof.

In some embodiments, the small molecule inhibitor of VprBP can be prepared according methods and using intermediates known in the art such as those described in U.S. Pat. No. 3,878,201 or PCT International Application Publication No. WO 2013/072921 and T. Baburaja, S. Thambidurai, *Synlett*, 2011, 1993-1996.

In some embodiments, the small molecule inhibitor of VprBP can be prepared according to Scheme 1:

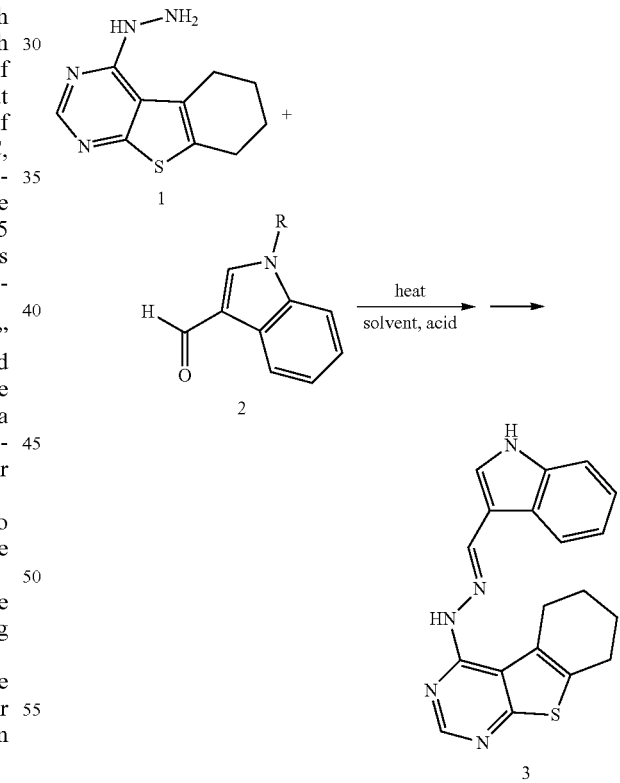

As shown in Scheme 1, Compound 1 (ChemExper, Belgium) can react with Compound 2 to give Compound 3 in a hydrophilic solvent such as ethanol, propanol, butanol, dioxane, etc., at an elevated temperature such as about 75° to 150° C., optionally in the presence of a catalytic amount of an acid, such hydrochloric acid, sulfuric acid, nitric acid, hydrobromic acid, hydrogen iodide, maleic acid, fumaric acid, etc. R in Compound 2 is H or an amino protecting group, such as tert-butoxycarbonyl (Boc), benzyloxycarbonyl (Cbz), or [(9-fluorenylmethyl)oxy]carbonyl (Fmoc). When R is H, Compound 2 is 1H-indole-3-carbaldehyde (ChemExper, Belgium) and the reaction in Scheme 1 produces B32B3 directly. When R is an amino protecting group, Compound 2 can be prepared from 1H-indole-3-carbaldehyde with methods known in the art. After reaction of Compound 1 and Compound 2, the protecting group can be removed under conditions known in the art, such as acidic condition when R is Boc, hydrogenation condition when R is Cbz, and basic condition when R is Fmoc. Additional amino protecting groups, the conditions to add a protect group to 1H-indole-3-carbaldehyde, and conditions to remove the protect group are known in the art, for example, described in T. W. Greene and P. G. M. Wuts, *Protecting Groups in Organic Synthesis*, Third Edition, Wiley, New York, 1999, and references cited therein.

"Pharmaceutically acceptable salt" refers to salts of a compound, which salts are suitable for pharmaceutical use and are derived from a variety of organic and inorganic counter ions well known in the art and include, when the compound contains an acidic functionality, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate (see Stahl and Wermuth, eds., "HANDBOOK OF PHARMACEUTICALLY ACCEPTABLE SALTS," (2002), Verlag Helvetica Chimica Acta, Zurich, Switzerland), for a discussion of pharmaceutical salts, their selection, preparation, and use.

Generally, pharmaceutically acceptable salts are those salts that retain substantially one or more of the desired pharmacological activities of the parent compound and which are suitable for in vivo administration. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydroiodic acid, etc.), sulfuric acid, nitric acid, phosphoric acid, and the like.

Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, alkylsulfonic acids (e.g., methanesulfonic acid, ethanesulfonic acid, 1,2-ethanedisulfonic acid, 2-hydroxyethanesulfonic acid, etc.), arylsulfonic acids (e.g., benzenesulfonic acid, 4 chlorobenzenesulfonic acid, 2-naphthalenesulfonic acid, 4-toluenesulfonic acid, camphorsulfonic acid, etc.), glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion, or an aluminum ion) or by an ammonium ion (e.g., an ammonium ion derived from an organic base, such as, ethanolamine, diethanolamine, triethanolamine, morpholine, piperidine, dimethylamine, diethylamine, triethylamine, and ammonia).

A solvate of a compound is a solid-form of the compound that crystallizes with less than one, one or more than one molecules of solvent inside in the crystal lattice. A few examples of solvents that can be used to create solvates, such as pharmaceutically acceptable solvates, include, but are not limited to, water, $C_1$-$C_6$ alcohols (such as methanol, ethanol, isopropanol, butanol, and can be optionally substituted) in general, tetrahydrofuran, acetone, ethylene glycol, propylene glycol, acetic acid, formic acid, and solvent mixtures thereof. Other such biocompatible solvents which may aid in making a pharmaceutically acceptable solvate are well known in the art. Additionally, various organic and inorganic acids and bases can be added to create a desired solvate. Such acids and bases are known in the art. When the solvent is water, the solvate can be referred to as a hydrate. In some embodiments, one molecule of a compound can form a solvate with from 0.1 to 5 molecules of a solvent, such as 0.5 molecules of a solvent (hemisolvate, such as hemihydrate), one molecule of a solvent (monosolvate, such as monohydrate) and 2 molecules of a solvent (disolvate, such as dihydrate).

"RNA interference" (RNAi) refers to sequence-specific or gene specific suppression of gene expression (protein synthesis) that is mediated by short interfering RNA (siRNA).

"Short interfering RNA" (siRNA) refers to double-stranded RNA molecules (dsRNA), generally, from about 10 to about 30 nucleotides in length that are capable of mediating RNA interference (RNAi), or 11 nucleotides in length, 12 nucleotides in length, 13 nucleotides in length, 14 nucleotides in length, 15 nucleotides in length, 16 nucleotides in length, 17 nucleotides in length, 18 nucleotides in length, 19 nucleotides in length, 20 nucleotides in length, 21 nucleotides in length, 22 nucleotides in length, 23 nucleotides in length, 24 nucleotides in length, 25 nucleotides in length, 26 nucleotides in length, 27 nucleotides in length, 28 nucleotides in length, or 29 nucleotides in length. As used herein, the term siRNA includes short hairpin RNAs (shRNAs). A siRNA directed to a gene or the mRNA of a gene may be a siRNA that recognizes the mRNA of the gene and directs a RNA-induced silencing complex (RISC) to the mRNA, leading to degradation of the mRNA. A siRNA directed to a gene or the mRNA of a gene may also be a siRNA that recognizes the mRNA and inhibits translation of the mRNA. The siRNA can be administered as naked DNA or within an expression or delivery vehicle.

"Double stranded RNA" (dsRNA) refer to double stranded RNA molecules that may be of any length and may be cleaved intracellularly into smaller RNA molecules, such as siRNA. In cells that have a competent interferon response, longer dsRNA, such as those longer than about 30 base pair in length, may trigger the interferon response. In other cells that do not have a competent interferon response, dsRNA may be used to trigger specific RNAi.

microRNA or miRNA are single-stranded RNA molecules of 21-23 nucleotides in length, which regulate gene expression. miRNAs are encoded by genes from whose DNA they are transcribed but miRNAs are not translated into protein (non-coding RNA); instead each primary transcript (a pri-miRNA) is processed into a short stem-loop structure called a pre-miRNA and finally into a functional miRNA. Mature miRNA molecules are partially complementary to one or more messenger RNA (mRNA) molecules, and their main function is to down-regulate gene expression.

A siRNA vector, dsRNA vector or miRNA vector as used herein, refers to a plasmid or viral vector comprising a promoter regulating expression of the RNA. "siRNA promoters" or promoters that regulate expression of siRNA, dsRNA, or miRNA are known in the art, e.g., a U6 promoter as described in Miyagishi and Taira (2002) Nature Biotech. 20:497-500, and a H1 promoter as described in Brummelkamp et al. (2002) Science 296:550-3.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

Various proteins are also disclosed herein with their GenBank Accession Numbers for their human proteins and coding sequences. However, the proteins are not limited to human-derived proteins having the amino acid sequences represented by the disclosed GenBank Accession numbers, but may have an amino acid sequence derived from other animals, particularly, a warm-blooded animal (e.g., rat, guinea pig, mouse, chicken, rabbit, pig, sheep, cow, monkey, etc.).

A "gene delivery vehicle" is defined as any molecule that can carry inserted polynucleotides into a host cell. Examples of gene delivery vehicles are liposomes, micelles, biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide of this invention can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

Gene delivery vehicles also include DNA/liposome complexes, micelles and targeted viral protein-DNA complexes. Liposomes that also comprise a targeting antibody or fragment thereof can be used in the methods of this invention. To enhance delivery to a cell, the nucleic acid or proteins of this invention can be conjugated to antibodies or binding fragments thereof which bind cell surface antigens. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins of this invention are other non-limiting techniques.

"Administration" can be effected in one dose, continuously or intermittently throughout the course of treatment. Methods of determining appropriate means and dosage of administration are known to those of skill in the art and will vary with the composition used for therapy, the purpose of the therapy, the target cell being treated and the subject being treated. Single or multiple administrations can be carried out with the dose level and pattern being selected by the treating physician. Suitable dosage formulations and methods of administering the agents are known in the art. Route of administration can also be determined and method of determining appropriate route of administration are known to those of skill in the art and will vary with the composition used for treatment, the purpose of the treatment, the health condition or disease stage of the subject being treated and target cell or tissue. Non-limiting examples of route of administration include oral administration, nasal administration, injection and topical application.

The term "effective amount" refers to a quantity sufficient to achieve a beneficial or desired result or effect. In the context of therapeutic or prophylactic applications, the effective amount will depend on the type and severity of the condition at issue and the characteristics of the individual subject, such as general health, age, sex, body weight, and tolerance to pharmaceutical compositions. The skilled artisan will be able to determine appropriate amounts depending on these and other factors.

In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

A "subject," "individual" or "patient" is used interchangeably herein, and refers to a vertebrate, preferably a mammal, more preferably a human. Mammals include, but are not limited to, murines, rats, rabbits, simians, bovines, ovines, porcines, canines, felines, farm animals, sport animals, pets, equines, and primates, particularly humans.

The agents and compositions can be used in the manufacture of medicaments and for the treatment of humans and other animals by administration in accordance with conventional procedures, such as an active ingredient in pharmaceutical compositions.

An agent of the present invention can be administered for therapy by any suitable route of administration. It will also be appreciated that the preferred route will vary with the condition and age of the recipient and the disease being treated.

A "composition" typically intends a combination of the active agent, e.g., compound or composition, and a carrier, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri-, tetra-oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives and any of the above noted carriers with the additional proviso that they be acceptable for use in vivo. Examples of pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. For examples of carriers, stabilizers and adjuvants, see Martin REMINGTON'S PHARM. SCI., 15th Ed. (Mack Publ. Co., Easton (1975) and Williams & Williams, (1995), and in the "PHYSICIAN'S DESK REFERENCE", $52^{nd}$ ed., Medical Economics, Montvale, N.J. (1998).

The invention provides an article of manufacture, comprising packaging material and at least one vial comprising a solution of a VprBP inhibitor as described herein or its biological equivalent with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising a VprBP inhibitor or its biological equivalent and a second vial comprising an aqueous diluent of prescribed buffer or preservative, wherein said packaging material comprises a label that instructs a patient to reconstitute the therapeutic in the aqueous diluent to form a solution that can be held over a period of twenty-four hours or greater.

The VprBP inhibitor described herein as effective for their intended purpose can be administered to subjects or individuals identified by the methods herein as suitable for the therapy. Therapeutic amounts can be empirically determined and will vary with the pathology being treated, the subject being treated and the efficacy and toxicity of the agent.

In various embodiments of the methods of the invention, the VprBP inhibitor will be administered locally or systemically on a continuous, daily basis, at least once per day (QD) and in various embodiments two (BID), three (TID) or even four times a day. Typically, the therapeutically effective daily dose will be at least about 1 mg, or at least about 10 mg, or at least about 100 mg or about 200-about 500 mg and sometimes, depending on the compound, up to as much as about 1 g to about 2.5 g.

Dosage, toxicity and therapeutic efficacy of compositions described herein can be determined by standard pharmaceutical procedures in cell cultures or experimental animals, for example, to determine the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

In one aspect, the VprBP inhibitor is formulated in biodegradable biospheres (e.g., micelles or liposomes) or are coated on solid phase carriers such as or other devices.

The data obtained from the cell culture assays and animal studies can be used in formulating a range of dosage for use in humans. The dosage of such VprBP inhibitor lies preferably within a range of circulating concentrations that include the $ED_{50}$ with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, an effective amount of a composition sufficient for achieving a therapeutic or prophylactic effect, ranges from about 0.000001 mg per kilogram body weight per administration to about 10,000 mg per kilogram body weight per administration. Suitably, the dosage ranges are from about 0.0001 mg per kilogram body weight per administration to about 100 mg per kilogram body weight per administration. Administration can be provided as an initial dose, followed by one or more "booster" doses. Booster doses can be provided a day, two days, three days, a week, two weeks, three weeks, one, two, three, six or twelve months after an initial dose. In some embodiments, a booster dose is administered after an evaluation of the subject's response to prior administrations.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

As used herein, the term "detectable label" intends a directly or indirectly detectable compound or composition that is conjugated directly or indirectly to the composition to be detected, e.g., N-terminal histadine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, luminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals (6$^{th}$ ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6$^{th}$ ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

Methods and Compostions

This disclosure provides a method for one or more of:
a. inhibiting the growth of a cancer cell;
b. activating tumor suppressor function in a cell comprising functional tumor suppressor genes; and
c. inhibiting H2AT120P in a cell comprising functional H2AT120P,
comprising, or alternatively of consisting essentially of, or yet further consisting of contacting the cell with an effective amount of an agent that inhibits VprBP kinase activity in the cell. In one aspect, the cell to be contacted is one that expresses VprBP kinase activity and/or one with tumor suppressor activity. In one aspect, the cell is a cancer cell and the cancer is a VprBR-related cancer, e.g., one that is selected from the group of a bladder cancer, a breast cancer or a prostate cancer. In a further aspect, the cancer is VprBR kinase-related in that the cancer is the result of lack of functional VprBR kinase activity in the cell or tissue. The cell can be of any appropriate species, e.g., a mammalian or a human cell. In one aspect, the inhibitor is a synthetic peptide comprising a HIV1 TAT sequence and the H3 N-terminal tail domain which corresponds to amino acids 5-27 (QTARKSTGGKAPRKQLATKAARK (human histone H3 N-terminal tail corresponding to amino acids 5-27)-RKKRRQRRR (HIV1 TAT sequence)) (SEQ ID NO: 11), and sequences having at least 80% amino acid sequence identity and having the same or similar biological activity. Since the regulation of H2AT120 phosphorylation is important in the control of cell growth and the establishment and maintenance of gene silencing, the present invention should make it possible to detect and regulate VprBP dysfunction related to cancer development. In addition, the invention provides a method of reducing H2AT120 phosphorylation by using histone H3 tail peptides which block VprBP kinase activity and therefore reduce VprBP carcinogenic potential in cancer cells.

This disclosure also provides a method for inhibiting the growth of a cancer cell in a patient or treating cancer in a patient, comprising administering to the patient in need thereof an effective amount of VprBR kinase-specific RNAi or a small molecule inhibitor of VprBP. In one aspect, the cell to be contacted is one that expresses VprBP kinase activity and/or one with tumor suppressor activity. In one aspect, the cancer is selected from the group of a bladder cancer, a breast cancer or a prostate cancer. In a further aspect, the cancer is VprBR kinase-related in that the cancer is the result of lack of functional VprBR kinase activity in the cell or tissue. The patient is a mammal or a human patient.

The above methods can be performed in vitro or in vivo, and with an agent comprising, or alternatively consisting essentially of, or yet further consisting of, a VprBR kinase-specific RNAi or a small molecule inhibitor of VprBP. The polynucleotides include for example those which are, or that encode VprBR kinase-specific RNA interference (RNAi) such as siRNA, miRNA dsRNA, mRNA and antisense RNA, as well DNA, such as in gene therapy applications.

In one aspect, the small molecule inhibitor of VprBP is a compound of the formula:

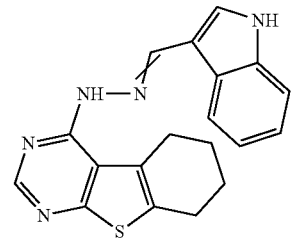 [SMILES: c1ccc2c(CNNc3ncnc4sc5c(c34)CCCC5)c[nH]c2c1]

or a pharmaceutically acceptable salt thereof or a solvate of the compound or the salt thereof or an equivalent thereof.

In another aspect, VprBR kinase-specific RNAi is selected from the group consisting of a reference polynucleotide of VprBP shRNA1, comprising, or alternatively consisting essentially of, or yet further consisting, or a sequence of one or more of (SEQ ID NO: 1: 5'-CGAGAAACTGAGT-CAAATGAA-3'), VprBP shRNA2 (SEQ ID NO: 2: 5'-AAT- CACAGAGTATCTTAGA-3') and Bub1 shRNA (SEQ ID NO: 3: 5'-CGAGGTTAATCCAGCACGTAT-3'), or an equivalent of each thereof, wherein an equivalent thereof comprises a polynucleotide that has at least 80% sequence identity to the reference polynucleotide and inhibits VprBP kinase activity and/or one that hybridizes under conditions of high stringency to the reference polynucleotide or its complement, wherein conditions of high stringency comprise hybridization reaction at about 60° C. in about 1×SSC, and inhibits VprBP kinase activity.

In one aspect, the methods are practiced by administering an effective amount of, or by contacting the cell with, a synthetic peptide comprising, or alternatively consisting essentially of, or yet further consisting of, a HIV1 TAT sequence and the H3 N-terminal tail domain which corresponds to amino acids 5-27 (QTARKSTGGKAPRKQLAT-KAARK (human histone H3N-terminal tail corresponding to amino acids 5-27)-RKKRRQRRR (HIV1 TAT sequence)) (SEQ ID NO: 11), and sequences having at least 80% amino acid sequence identity and having the same or similar biological activity. Since the regulation of H2AT120 phosphorylation is important in the control of cell growth and the establishment and maintenance of gene silencing, the present invention should make it possible to detect and regulate VprBP dysfunction related to cancer development.

This disclosure also provides a method of determining whether a patient is more likely or less likely to be diagnosed with a VprBR-related cancer, comprising or alternatively consisting essentially of, or yet further consisting of screening a sample isolated from the patient for the presence of VprBP in a sample of the patient, wherein the presence of VprBP is an indication that the patient is more likely to be diagnosed with a VprBR-related cancer in the patient and an absence of VprBR is an indication that the patient is less likely to be diagnosed with a VprBR-related cancer, and optionally administering to the patient identified as more likely to be diagnosed with cancer an effective amount of an agent that inhibits VprBP kinase activity. In one aspect, an overexpression of VprBP is indicative of a cancer in the patient and normal or under expression of VprBP is an indicative that the patient is less likely to be diagnosed with a VprBR-related cancer. In one aspect, the cancer is selected from the group of a bladder cancer, a breast cancer or a prostate cancer. In a further aspect, the patient is a mammal such as a human patient. The sample can be a cell sample such as a bladder cell, breast cell or prostate cell. The cell can be a human cell or a mammalian cell.

Also provided are methods for determining the effectiveness of treating a VprBR-related cancer in a patient by VprBP inhibition, comprising comparing the expression level of one or more gene selected from Tables 2 and 3 in a sample isolated of the patient before treatment by administration of a VprBP inhibiting agent with the expression level of the one or more gene in a sample of the patient after treatment, wherein an increased expression of a gene selected from Table 2 or decreased expression of a gene selected from Table 3 is indicative of positive effectiveness of VprBP inhibition in treating the cancer in the patient. In one aspect, the cancer is selected from the group of a bladder cancer, a breast cancer or a prostate cancer. In a further aspect, the patient is a mammal such as a human patient. The sample can be a cell sample such as a bladder cell, breast cell or prostate cell.

Compositions are further provided herein. In one aspect, the composition comprises, or alternatively consists essentially of, or yet further consists of a carrier and a compound of the formula:

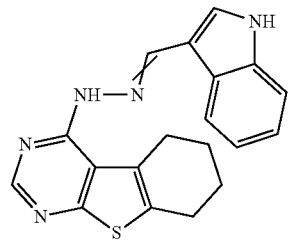 [SMILES: c1ccc2c(CNNc3ncnc4sc5c(c34)CCCC5)c[nH]c2c1]

or a pharmaceutically acceptable salt thereof, a solvate or a salt of the sovate or an equivalent of each thereof.

In one aspect, the compound is present in the composition in an amount from about 0.01 mg to 10 g/day or 1 mg/day to 10 g/day.

Further provided are compositions comprising, or alternatively consisting essentially of, or yet further consisting of a carrier and a VprBR kinase-specific RNAi. In one aspect, the VprBR kinase-specific RNAi is selected from the group of reference polynucleotides that consists essentially of or consist of VprBP shRNA1 (SEQ ID NO: 1: 5'-CGAGAAACT-GAGTCAAATGAA-3'), VprBP shRNA2 (SEQ ID NO: 2: 5'-AATCACAGAGTATCTTAGA-3') and Bub1 shRNA (SEQ ID NO: 3:5'-CGAGGTTAATCCAGCACGTAT-3'), or an equivalent thereof, wherein an equivalent thereof comprises a polynucleotide that has at least 80% sequence identity to the reference polynucleotide and inhibits VprBP kinase activity, and/or one that hybridizes under conditions of high stringency to the reference polynucleotide or its complement, wherein conditions of high stringency comprise hybridization reaction at about 60° C. in about 1×SSC and inhibits VprBP kinase activity.

The polynucleotides of this disclosure can be replicated using conventional recombinant techniques in a mammalian or human host system. Alternatively, the polynucleotides can be replicated using PCR technology. PCR is the subject matter of U.S. Pat. Nos. 4,683,195; 4,800,159; 4,754,065; and 4,683,202 and described in PCR: The Polymerase Chain Reaction (Mullis et al. eds, Birkhauser Press, Boston (1994)) and references cited therein. Yet further, one of skill in the art can use the sequences provided herein and a commercial DNA synthesizer to replicate the DNA. Accordingly, this disclosure also provides a process for obtaining the polynucleotides of this disclosure by providing the linear sequence of the polynucleotide, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can operatively link the polynucleotides to regulatory sequences for their expression in a host cell, described below. The polynucleotides and regulatory sequences are inserted into the host cell (prokaryotic or eukaryotic) for replication and amplification. The DNA so amplified can be isolated from the cell by methods well known to those of skill in the art. A process for obtaining polynucleotides by this method is further provided herein as well as the polynucleotides so obtained.

Also provided are host cells comprising one or more of the polypeptides or polynucleotides of this disclosure. In one aspect, the polypeptides are expressed and can be isolated from the host cells. In another aspect, the polypeptides are expressed and secreted. In yet another aspect, the polypeptides are expressed and present on the cell surface (extracellularly). Suitable cells containing the inventive polypeptides include prokaryotic and eukaryotic cells, which include, but are not limited to bacterial cells, algae cells, yeast cells, insect cells, plant cells, animal cells, mammalian cells, murine cells, rat cells, sheep cells, simian cells and human cells. A non-limiting example of algae cells is red alga *Griffithsia* sp. from which Griffithsin was isolated (Toshiyuki et al. (2005) J. Biol. Chem. 280(10):9345-53). A non-limiting example of plant cells is a *Nicotiana benthamiana* leaf cell from which Griffithsin can be produced in a large scale (O'Keefe (2009) Proc. Nat. Acad. Sci. USA 106(15):6099-6104). Examples of bacterial cells include *Escherichia coli* (Giomarelli et al. (2006), supra), *Salmonella enteric, Streptococcus gordonii* and *lactobacillus* (Liu et al. (2007) Cellular Microbiology 9:120-130; Rao et al. (2005) PNAS 102:11993-11998; Chang et al. (2003) PNAS 100(20):11672-11677; Liu et al. (2006) Antimicrob. Agents & Chemotherapy 50(10):3250-3259). The cells can be purchased from a commercial vendor such as the American Type Culture Collection (ATCC, Rockville Md., USA) or cultured from an isolate using methods known in the art. Examples of suitable eukaryotic cells include, but are not limited to 293T HEK cells, as well as the hamster cell line CHO, BHK-21; the murine cell lines designated NIH3T3, NS0, C127, the simian cell lines COS, Vero; and the human cell lines HeLa, PER.C6 (commercially available from Crucell) U-937 and Hep G2. A non-limiting example of insect cells include *Spodoptera frugiperda*. Examples of yeast useful for expression include, but are not limited to *Saccharomyces, Schizosaccharomyces, Hansenula, Candida, Torulopsis, Yarrowia*, or *Pichia*. See e.g., U.S. Pat. Nos. 4,812,405; 4,818,700; 4,929,555; 5,736,383; 5,955,349; 5,888,768 and 6,258,559.

For the compositions of this disclosure, the carrier is a pharmaceutically acceptable carrier or an in situ device. In one aspect, the device is a catheter.

Also provided are reference of a sequence selected from the group of:

a.

Q-PLRTYSTGLLGGAMENQDI;        (SEQ ID NO: 4)

b.

EVALRQENKRPSPRKLS;            (SEQ ID NO: 5)

c.

(SEQ ID NO: 6)
    DPDRMFVELSNSSWSEMSPWVIGTNYTLYPMTPAIEQRL;

d.

(SEQ ID NO: 7)
              YIDLKQTNDVL;

e.

(SEQ ID NO: 8)
                FATEFV;

f.

(SEQ ID NO: 9)
              KLLEIPRPS;

g.

(SEQ ID NO: 10)
              QDAMERVCM;

h. QTARKSTGGKAPRKQLATKAARK (human histone H3 N-terminal tail corresponding to amino acids 5-27)-RKKRRQRRR (HIV1 TAT sequence) (SEQ ID NO: 11); or i. a polypeptide comprising at least two of a. through h.; or j. or an equivalent thereof, wherein an equivalent thereof comprises a polypeptide that has at least 80% sequence identity to the reference polypeptide, and/or a polypeptide encoded by a polynucleotide that hybridizes under conditions of high stringency to a polynucleotide or its complement that encodes the reference polypeptide, wherein conditions of high stringency comprise hybridization reaction at about 60° C. in about 1×SSC.

Isolated polynucleotides encoding the polypeptides are further provided. The polypeptides and/or polynucleotides can be combined with a carrier, such as a pharmaceutically acceptable carrier or contained within a host cell, e.g., a mammalian cell.

Polypeptides comprising the amino acid sequences for use in the methods of the disclosure can be prepared by expressing polynucleotides encoding the polypeptide sequences of this disclosure in an appropriate host cell. This can be accomplished by methods of recombinant DNA technology known to those skilled in the art. Accordingly, this disclosure also provides methods for recombinantly producing the polypeptides of this disclosure in a eukaryotic or prokaryotic host cells, as well as the isolated host cells used to produce the proteins. The proteins and polypeptides of this disclosure also can be obtained by chemical synthesis using a commercially available automated peptide synthesizer such as those manufactured by Perkin Elmer/Applied Biosystems, Inc., Model 430A or 431A, Foster City, Calif., USA. The synthesized protein or polypeptide can be precipitated and further purified, for example by high performance liquid chromatography (HPLC). Accordingly, this disclosure also provides a process for chemically synthesizing the proteins of this disclosure by providing the sequence of the protein and reagents, such as amino acids and enzymes and linking together the amino acids in the proper orientation and linear sequence.

It is known to those skilled in the art that modifications can be made to any peptide to provide it with altered properties. Polypeptides of the disclosure can be modified to include unnatural amino acids. Thus, the peptides may comprise D-amino acids, a combination of D- and L-amino acids, and various "designer" amino acids (e.g., β-methyl amino acids, C-α-methyl amino acids, and N-α-methyl amino acids, etc.) to convey special properties to peptides. Additionally, by assigning specific amino acids at specific coupling steps, peptides with α-helices, β turns, β sheets, α-turns, and cyclic peptides can be generated. Generally, it is believed that α-helical secondary structure or random secondary structure is preferred.

In a further embodiment, subunits of polypeptides that confer useful chemical and structural properties will be chosen. For example, peptides comprising D-amino acids may be resistant to L-amino acid-specific proteases in vivo. Modified compounds with D-amino acids may be synthesized with the amino acids aligned in reverse order to produce the peptides of the disclosure as retro-inverso peptides. In addition, the present disclosure envisions preparing peptides that have better defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2NH$—$R_2$, where $R_1$, and $R_2$ are amino acid residues or sequences. A reduced peptide bond may be introduced as a dipeptide subunit. Such a molecule would be resistant to peptide bond hydrolysis, e.g., protease activity. Such molecules would provide ligands with unique function and activity, such as extended half-lives in vivo due to resistance to metabolic breakdown, or protease activity. Furthermore, it is well known that in certain systems constrained peptides show enhanced functional activity (Hruby (1982) Life Sciences 31:189-199 and Hruby et al. (1990) Biochem J. 268:249-262); the present disclosure provides a method to produce a constrained peptide that incorporates random sequences at all other positions.

Non-classical amino acids may be incorporated in the peptides of the disclosure in order to introduce particular conformational motifs, examples of which include without limitation: 1,2,3,4-tetrahydroisoquinoline-3-carboxylate (Kazmierski et al. (1991) J. Am. Chem. Soc. 113:2275-2283); (2S,3S)-methyl-phenylalanine, (2S,3R)-methyl-phenylalanine, (2R,3S)-methyl-phenylalanine and (2R,3R)-methyl-phenylalanine (Kazmierski & Hruby (1991) Tetrahedron Lett. 32(41):5769-5772); 2-aminotetrahydronaphthalene-2-carboxylic acid (Landis (1989) Ph.D. Thesis, University of Arizona); hydroxy-1,2,3,4-tetrahydroisoquinoline-3-carboxylate (Miyake et al. (1989) J. Takeda Res. Labs. 43:53-76) histidine isoquinoline carboxylic acid (Zechel et al. (1991) Int. J. Pep. Protein Res. 38(2):131-138); and HIC (histidine cyclic urea), (Dharanipragada et al. (1993) Int. J. Pep. Protein Res. 42(1):68-77) and (Dharanipragada et al. (1992) Acta. Crystallogr. C. 48:1239-1241).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog (Kemp et al. (1985) J. Org. Chem. 50:5834-5838); β-sheet inducing analogs (Kemp et al. (1988) Tetrahedron Lett. 29:5081-5082); β-turn inducing analogs (Kemp et al. (1988) Tetrahedron Lett. 29:5057-5060); α-helix inducing analogs (Kemp et al. (1988) Tetrahedron Lett. 29:4935-4938); α-turn inducing analogs (Kemp et al. (1989) J. Org. Chem. 54:109:115); analogs provided by the following references: Nagai & Sato (1985) Tetrahedron Lett. 26:647-650; and DiMaio et al. (1989) J. Chem. Soc. Perkin Trans. p. 1687; a Gly-Ala turn analog (Kahn et al. (1989) Tetrahedron Lett. 30:2317); amide bond isostere (Clones et al. (1988) Tetrahedron Lett. 29:3853-3856); tetrazole (Zabrocki et al. (1988) J. Am. Chem. Soc. 110:5875-5880); DTC (Samanen et al. (1990) Int. J. Protein Pep. Res. 35:501:509); and analogs taught in Olson et al. (1990) J. Am. Chem. Sci. 112:323-333 and Garvey et al. (1990) J. Org. Chem. 56:436. Conformationally restricted mimetics of beta turns and beta bulges, and peptides containing them, are described in U.S. Pat. No. 5,440,013.

It is known to those skilled in the art that modifications can be made to any peptide by substituting one or more amino acids with one or more functionally equivalent amino acids that does not alter the biological function of the peptide. In one aspect, the amino acid that is substituted by an amino acid that possesses similar intrinsic properties including, but not limited to, hydrophobicity, size, or charge. Methods used to determine the appropriate amino acid to be substituted and for which amino acid are know to one of skill in the art. Non-limiting examples include empirical substitution models as described by Dahoff et al. (1978) In Atlas of Protein Sequence and Structure Vol. 5 suppl. 2 (ed. M. O. Dayhoff), pp. 345-352. National Biomedical Research Foundation, Washington D.C.; PAM matrices including Dayhoff matrices (Dahoff et al. (1978), supra, or JTT matrices as described by Jones et al. (1992) Comput. Appl. Biosci. 8:275-282 and Gonnet et al. (1992) Science 256:1443-1145; the empirical model described by Adach & Hasegawa (1996) J. Mol. Evol. 42:459-468; the block substitution matrices (BLOSUM) as described by Henikoff & Henikoff (1992) Proc. Natl. Acad. Sci. USA 89:1-1; Poisson models as described by Nei (1987) Molecular Evolutionary Genetics. Columbia University Press, New York; and the Maximum Likelihood (ML) Method as described by Müller et al. (2002) Mol. Biol. Evol. 19:8-13.

RNAi or siRNA

A siRNA can be designed following procedures known in the art. See, e.g., Dykxhoorn, D. M. and Lieberman, J. (2006) "Running Interference: Prospects and Obstacles to Using Small Interfering RNAs as Small Molecule Drugs," Annu Rev. Biomed. Eng. 8:377-402; Dykxhoorn, D. M. et al. (2006) "The silent treatment: siRNAs as small molecule drugs," Gene Therapy, 13:541-52; Aagaard, L. and Rossi, J. J. (2007) "RNAi therapeutics: Principles, prospects and challenges," Adv. Drug Delivery Rev. 59:75-86; de Fougerolles, A. et al. (2007) "Interfering with disease: a progress report on siRNA-based therapeutics," Nature Reviews Drug Discovery 6:443-53; Krueger, U. et al. (2007) "Insights into effective RNAi gained from large-scale siRNA validation screening," Oligonucleotides 17:237-250; U.S. Patent Application Publication No. 2008/0188430; and U.S. Patent Application Publication No. 2008/0249055.

siRNAs can be made with methods known in the art. See, e.g., Dykxhoorn, D. M. and Lieberman, J. (2006) "Running Interference: Prospects and Obstacles to Using Small Interfering RNAs as Small Molecule Drugs," Annu. Rev. Biomed. Eng. 8:377-402; Dykxhoorn, D. M. et al. (2006) "The silent treatment: siRNAs as small molecule drugs," Gene Therapy, 13:541-52; Aagaard, L. and Rossi, J. J. (2007) "RNAi therapeutics: Principles, prospects and challenges," Adv. Drug Delivery Rev. 59:75-86; de Fougerolles, A. et al. (2007) "Interfering with disease: a progress report on siRNA-based therapeutics," Nature Reviews Drug Discovery 6:443-53; Krueger, U. et al. (2007) "Insights into effective RNAi gained from large-scale siRNA validation screening," Oligonucleotides 17:237-250; U.S. Patent Application Publication No. 2008/0188430; and U.S. Patent Application Publication No. 2008/0249055.

A siRNA may be chemically modified to increase its stability and safety. See, e.g., Dykxhoorn, D. M. and Lieberman, J. (2006) "Running Interference: Prospects and Obstacles to Using Small Interfering RNAs as Small Molecule Drugs," Annu Rev. Biomed. Eng. 8:377-402 and U.S. Patent Application Publication No. 2008/0249055.

Antibody Compositions

The disclosure, in another aspect, provides an antibody that binds an isolated polypeptide of the disclosure. The antibody can be a polyclonal antibody, a monoclonal antibody, a chimeric antibody, a humanized antibody or a derivative or fragment thereof as defined below. In one aspect, the antibody is detectably labeled or further comprises a detectable label conjugated to it.

Also provided is a composition comprising the antibody and a carrier. Further provided is a biologically active fragment of the antibody, or a composition comprising the antibody fragment. Suitable carriers are defined supra.

Further provided is an antibody-peptide complex comprising, or alternatively consisting essentially of, or yet alternatively consisting of, the antibody and a polypeptide specifically bound to the antibody. In one aspect, the polypeptide is the polypeptide against which the antibody is raised.

This disclosure also provides an antibody capable of specifically forming a complex with a protein or polypeptide of this disclosure, which are useful in the therapeutic methods of this disclosure. The term "antibody" includes polyclonal antibodies and monoclonal antibodies, antibody fragments, as well as derivatives thereof (described above). The antibodies include, but are not limited to mouse, rat, and rabbit or human antibodies. Antibodies can be produced in cell culture, in phage, or in various animals, including but not limited to cows, rabbits, goats, mice, rats, hamsters, guinea pigs, sheep, dogs, cats, monkeys, chimpanzees, apes, etc. The antibodies are also useful to identify and purify therapeutic polypeptides.

Combination Therapy

The compositions and related methods of the present invention may be used in combination with the administration of other antitumor therapies. These include, but are not limited to, the administration of chemotherapy, surgery, and/or radiation.

The additional therapeutic treatment can be added prior to, concurrent with, or subsequent to methods or compositions described herein, and can be contained within the same formulation or as a separate formulation.

Screening Assays

The present invention provides methods or in vitro screening assays for screening candidate agents to identify a potential therapeutic agent of inhibiting tumor growth or for tumor suppression, comprising contacting a candidate agent with VprBP, initiating a kinase reaction, wherein the agent is a potential therapeutic agent if a reduction of kinase activity as compared to the kinase activity of VprBP in the absence of the agent is observed.

Kits

Also provided are kits comprising, or alternatively consisting essentially of, or yet further consisting of, a polynucleotide, a polypeptide or compound of this disclosure and optionally, instructions for use in the therapeutic, diagnostic and/or screening methods disclosed herein.

EXPERIMENTAL

Experiment No. 1

Histone modifications play important roles in the regulation of gene expression and chromatin organization. VprBP has been implicated in transcriptionally silent chromatin formation and cell-cycle regulation, but the molecular basis underlying such effects remains unclear. Here Applicants report that VprBP possesses an intrinsic protein kinase activity and is capable of phosphorylating histone H2A on threonine 120 (H2AT120p) in a nucleosomal context. VprBP is localized to a large set of tumor suppressor genes and blocks their transcription, in a manner that is dependent on its kinase activity toward H2AT120. The functional significance of VprBP-mediated H2AT120p is further underscored by the fact that RNAi knockdown and small-molecule inhibition of VprBP reactivate growth regulatory genes and impede tumor growth. Applicants' findings establish VprBP as a major kinase responsible for H2AT120p in cancer cells and suggest that VprBP inhibition could be a new strategy for the development of anticancer therapeutics.

The formation of silent chromatin plays important roles in the regulation of gene expression and maintenance of chromosome stability in eukaryotes. Inactive chromatin domains are often associated with distinct histone modifications (Suganuma, T. et al. (2011) Annu Rev. Biochem. 80:473-499). Like other histone modifications, histone phosphorylation has been linked to various cellular processes such as transcriptional regulation and DNA repair (Banerjee, T. et al. (2011) Mol. Cell. Biol. 31:4858-4873). Histone phosphorylation can occur on serine, threonine, and tyrosine residues and constitutes a part of the signal to influence chromatin structure and factor recruitment. For example, phosphorylations of H3S10, H3S28, and H2BS32 are linked to the expression of proto-oncogenes such as c-fos, c-jun, and c-myc (Choi, H. S. et al. (2005) Cancer Res. 65:5818-5827; Lau, A. T. et al. (2011) J. Biol. Chem. 286:26628-26637; Lau, P. N. et al. (2011) Proc. Natl. Acad. Sci. USA 108:2801-2806). Phosphorylations of H3S10, H3T11, and H3S28 play a role in combination with H3 acetylation in transcription activation and cell proliferation (Gehani, S. S. et al. (2010) Mol. Cell 39:886-900; Lau, P. N. et al. (2011) Proc. Natl. Acad. Sci. USA 108:2801-2806; Lo, W. S. et al. (1998) J. Mol. Biol. 276:19-42; Shimada, M. et al. (2008) Cell 132:221-232; Yang, W. et al. (2012) Cell 150:685-696). Conversely, H2AS1 phosphorylation inhibits chromatin transcription, and H3 preacetylation interferes with this repressive modification (Zhang, Y. et al. (2004) J. Biol. Chem. 279:21866-21872). In some cases, histone phosphorylation facilitates nucleosome binding by proteins containing phospho-binding modules and restricts their activity as downstream effectors around a specific region. While a large number of phosphorylation sites have been identified in core histones, the identification of kinases responsible for these modifications remains an area of intensive investigation. VprBP is a large nuclear protein that can interact with HIV viral protein R and Cullin 4-DDB1 ubiquitin ligase complex (Li, W. et al. (2010) Cell 140:477-490). The cellular function of VprBP has been studied mainly with respect to its role in regulating Cullin 4 E3 ubiquitin ligase activity and cell-cycle progression (Hrecka, K. et al. (2007) Proc. Natl. Acad. Sci. USA 104:11778-11783; McCall, C. M. et al. (2008) Mol. Cell. Biol. 28, 5621-5633). However, more recent studies have implicated VprBP in a much wider range of cellular processes, as exemplified by its engagement in JNK-mediated apoptosis during cellcompetition process (Tamori, Y. et al. (2010) PLoS Biol. 8:e1000422). Another striking example is the demonstration made by us that VprBP acts as an effector that binds histone H3 tails protruding from nucleosomes and establishes chromatin silencing in cancer cells (Kim, K. et al. (2012) Mol. Cell. Biol. 32:783-796). These results clearly indicate that VprBP plays a negative regulatory role in transcription, but precisely how VprBP mediates its effects on the formation of repressive chromatin domain is poorly understood.

Here Applicants report that VprBP has an intrinsic kinase activity and phosphorylates histone H2A at threonine 120. Functional studies reveal that H2AT120p by VprBP is sufficient to repress chromatin transcription. RNA interference (RNAi)-mediated knockdown of VprBP impairs H2AT120p, transactivates a large set of tumor suppressor genes, and inhibits cell proliferation. Furthermore, using a highly potent and selective inhibitor for VprBP, Applicants show that down-regulation of VprBP-mediated H2AT120p impedes cancer cell proliferation and xenograft tumor progression.

Results

VprBP Possesses Kinase Activity and Phosphorylates Threonine 120 of Histone H2A

Figure 1B:
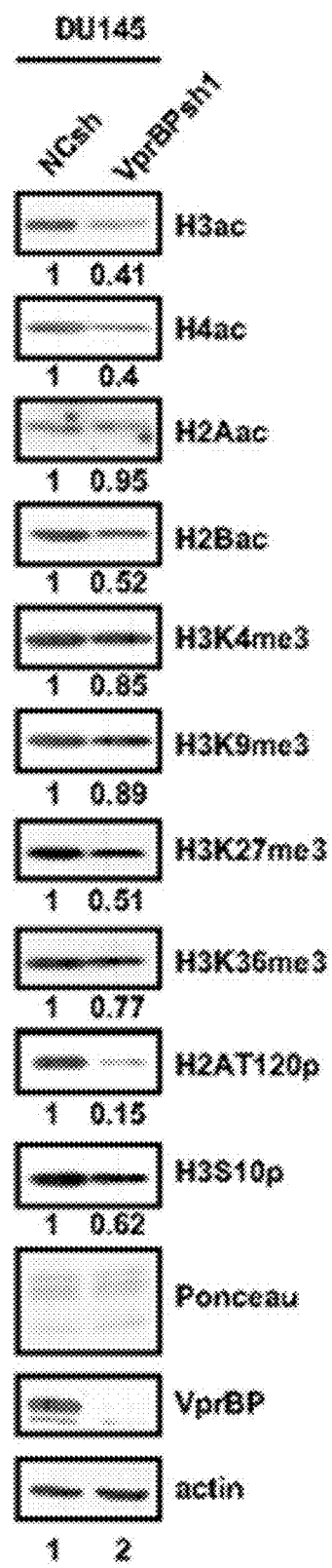
Figures 5A, 5B:
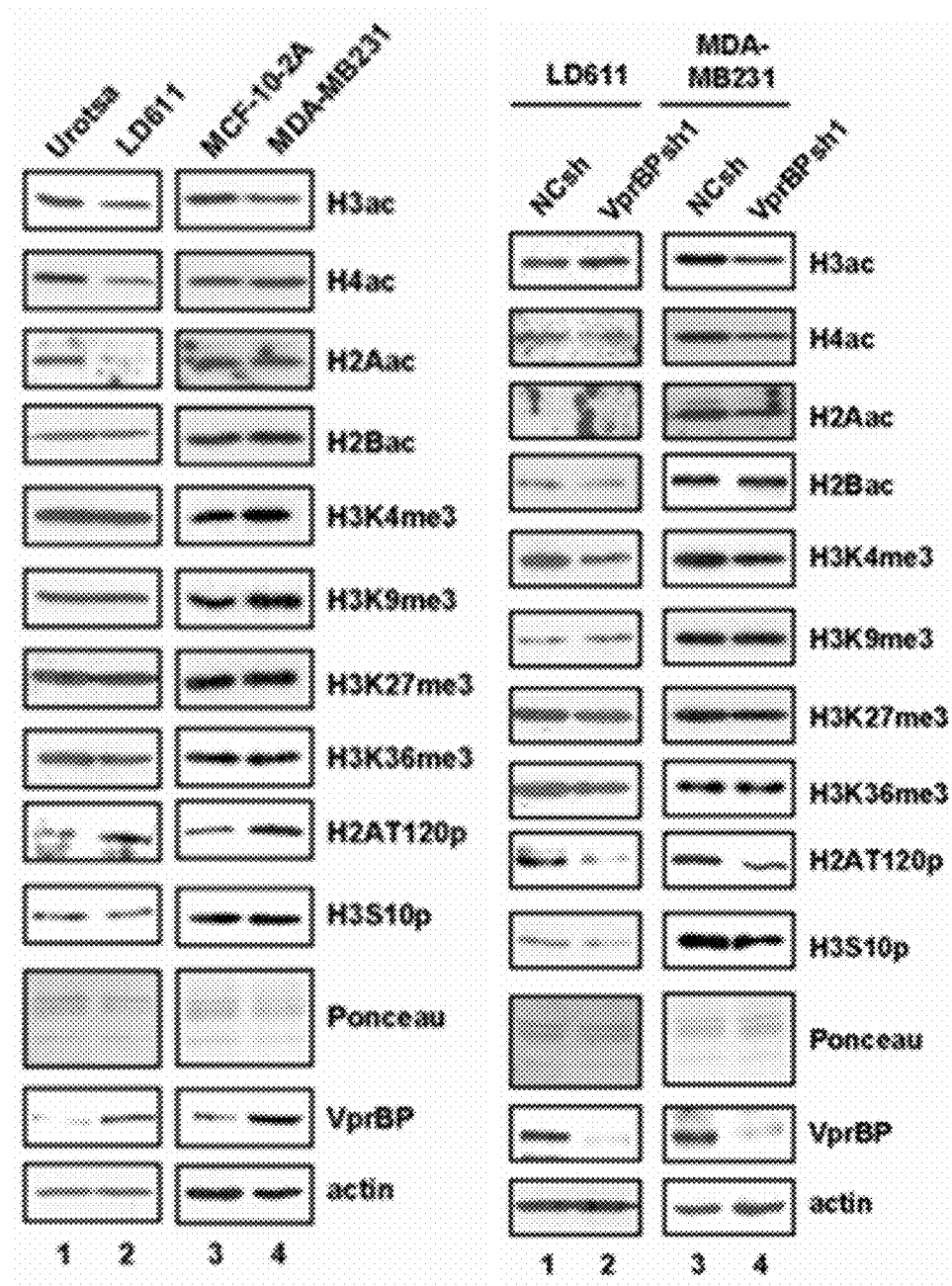
FIGS. 5A-5M show phosphorylation of H2A T120 by VprBP, related to FIG. 1.

Given that dysregulation of histone-modifying activities is linked to human cancers (Chi, P. et al. (2010) Nat. Rev. Cancer 10:457-469; Dawson, M. A. et al. (2012) Cell 150: 12-27), Applicants reasoned that VprBP expression in cancer cells might influence specific histone modifications. As expected, western blotting of cell lysates confirmed that VprBP is expressed highly in DU145 prostate, LD611 bladder, and MDA-MB231 breast cancer cell lines but minimally in their corresponding normal counterparts (FIGS. 1A and 5A). In exploring whether any histone modifications are altered in the cancer cell lines, Applicants detected much higher levels of H2AT120p in chromatin fractions. To assess the relationship between VprBP expression and H2AT120p more directly, Applicants examined a possible effect of VprBP depletion. Upon the stable knockdown of VprBP, the abundant H2AT120p found in the cancer cell lines was drastically reduced, but changes in other modifications were much less pronounced or absent (FIGS. 1B and 5B).

Figure 1C:
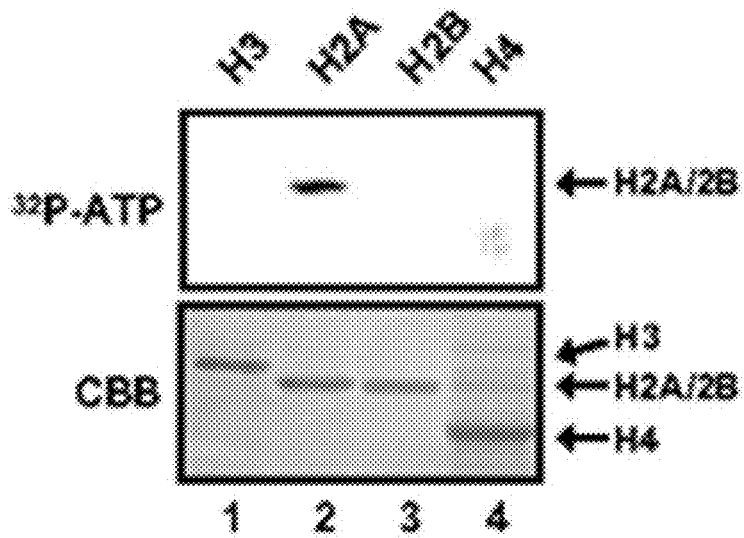
Figure 5C:
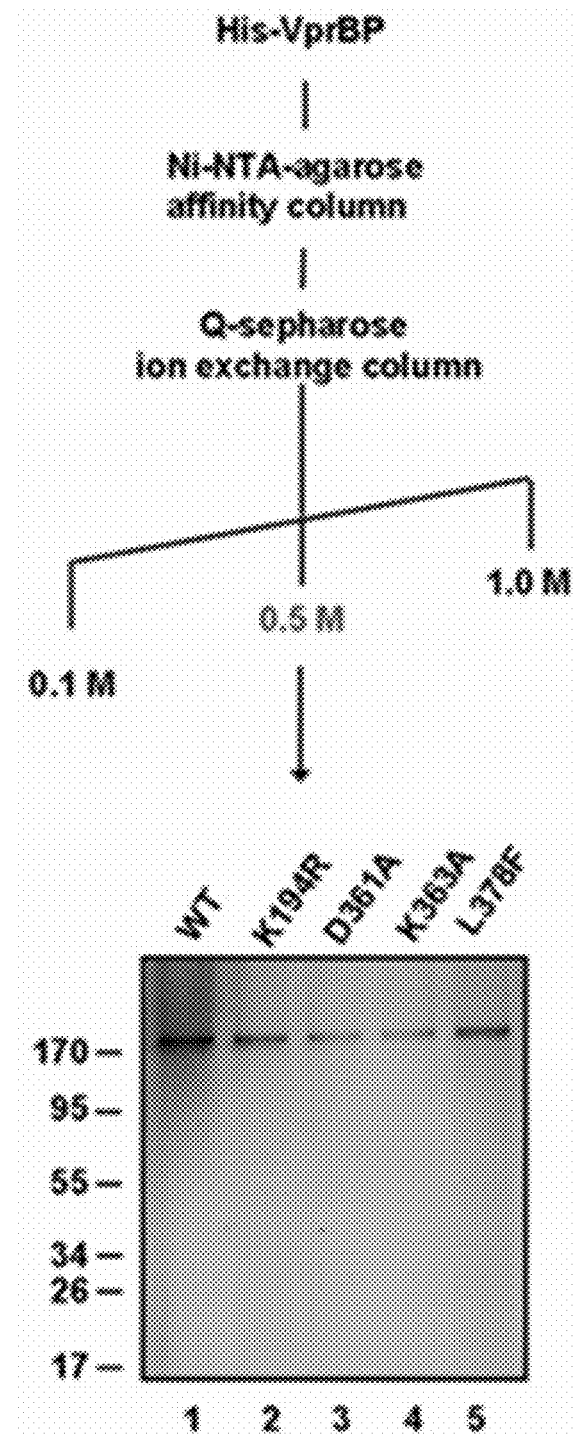
Figures 5D, 5E:
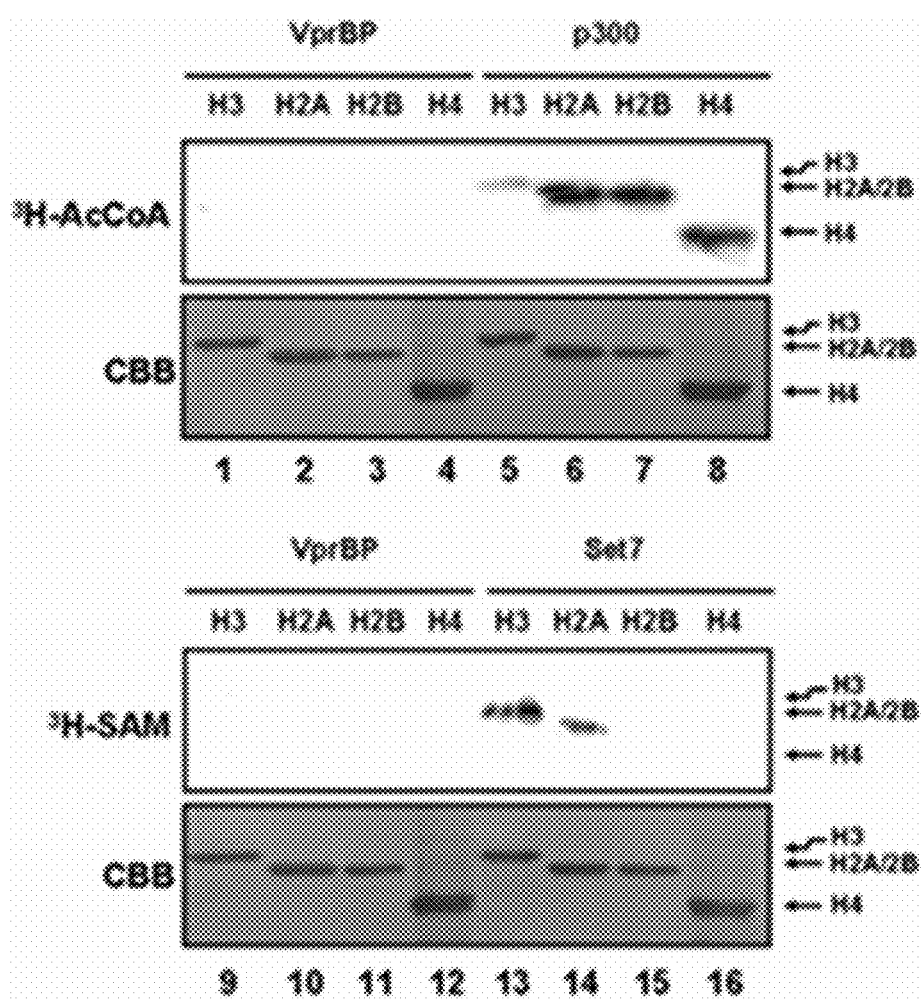
Figure 5F:
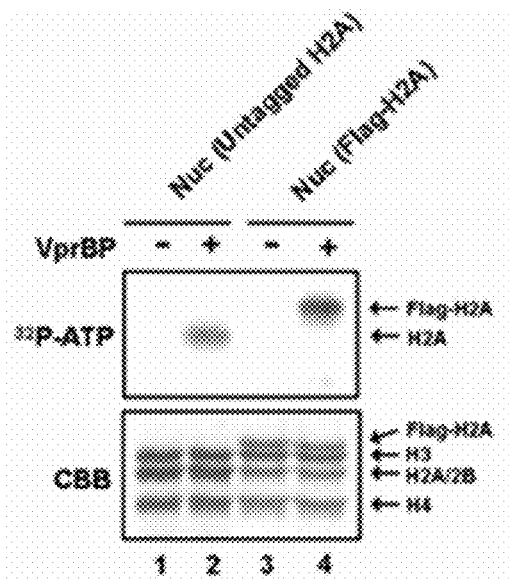
Figure 5G:
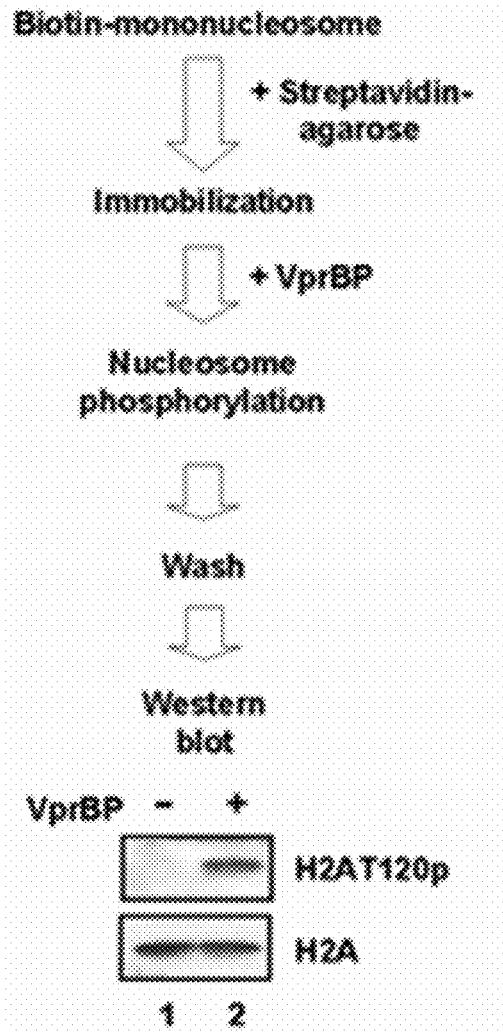
Figures 5H, 5I:
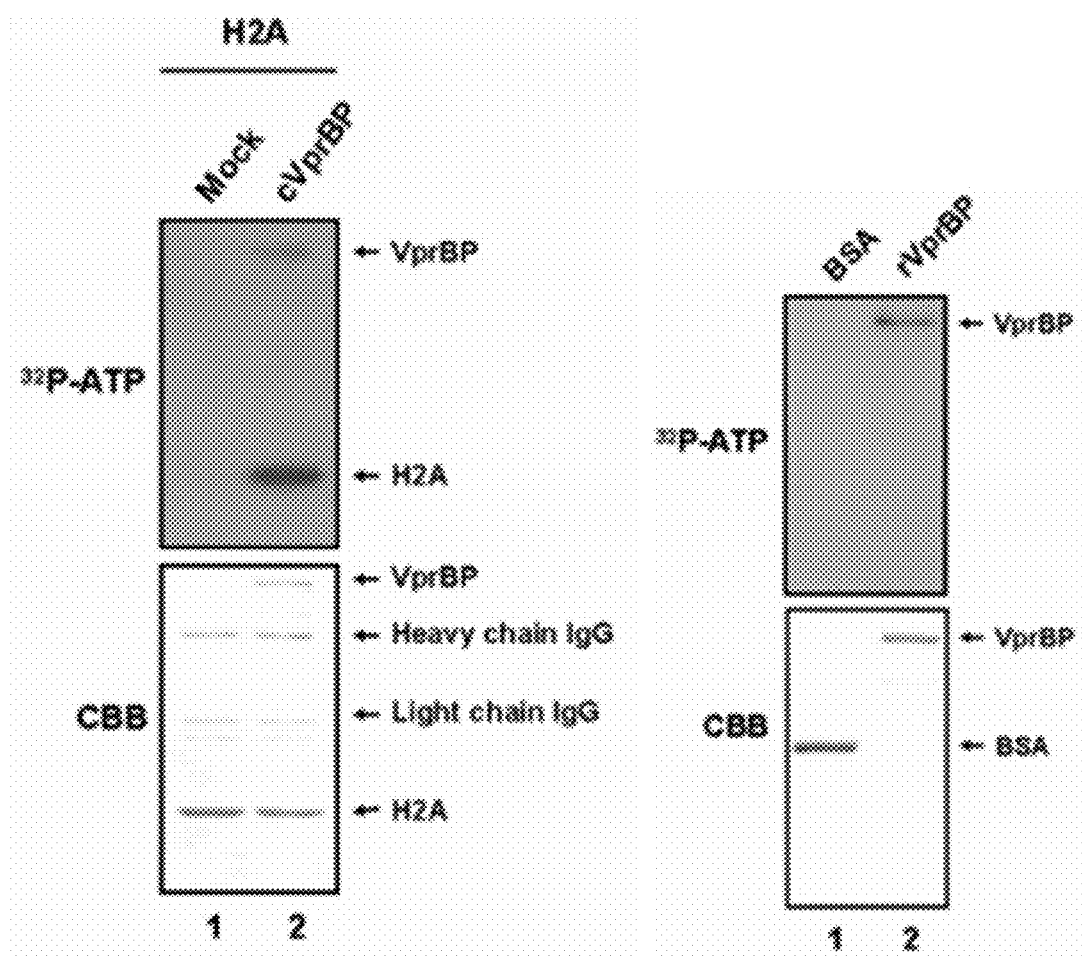

The data above suggest that VprBP may be of particular importance for H2AT120p reactions in cancer cells. To test this possibility, Applicants incubated free individual histones with [g-32P]-ATP and recombinant VprBP produced in baculovirus-infected insect cells. The integrity and purity of the VprBP protein were confirmed by silver-stained SDS-PAGE (FIG. 5C) and mass spectrometry (FIG. 5D). Autoradiograph of the kinase reaction products showed a robust phosphorylation of H2A, but not other core histones (FIG. 1C). Expectedly, VprBP showed no enzymatic activity in our in vitro HAT and HMT assays (FIG. 5E). As the core histones exist within nucleosomes in the cell nucleus, kinase assays were repeated with nucleosomes reconstituted from recombinant histones and the 601 nucleosome positioning sequence (Lowary, P. T. et al. (1998) J. Mol. Biol. 276:19-42). VprBP generated clear labeling of H2A in the nucleosome after autoradiography (FIG. 5F). These results were further corroborated by in vitro kinase assays with nucleosomes immobilized on agarose beads (FIG. 5G) and with VprBP immunoaffinity purified from DU145 cell lysates (FIG. 5H). In additional support, the in-gel autophosphorylation assays showed a phosphorylated band at the expected molecular weight of VprBP (FIG. 5I).

Figure 1D:
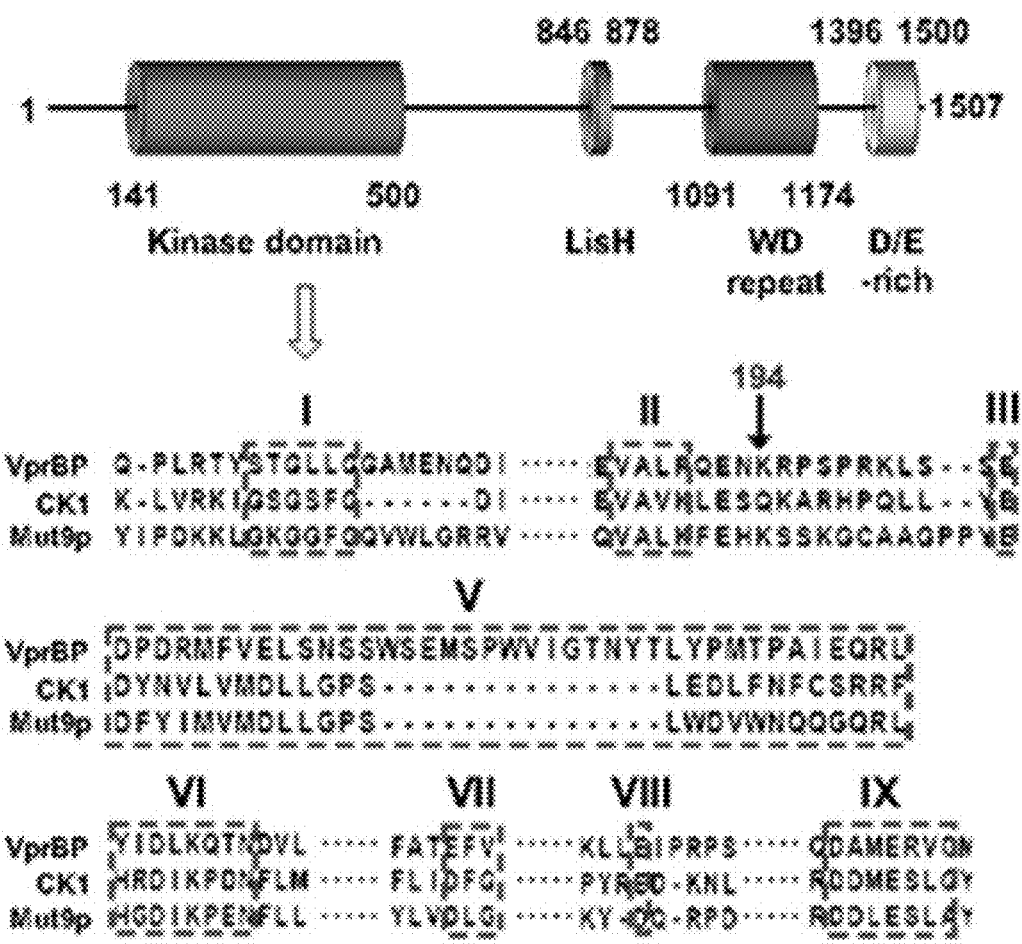
Figure 1E:
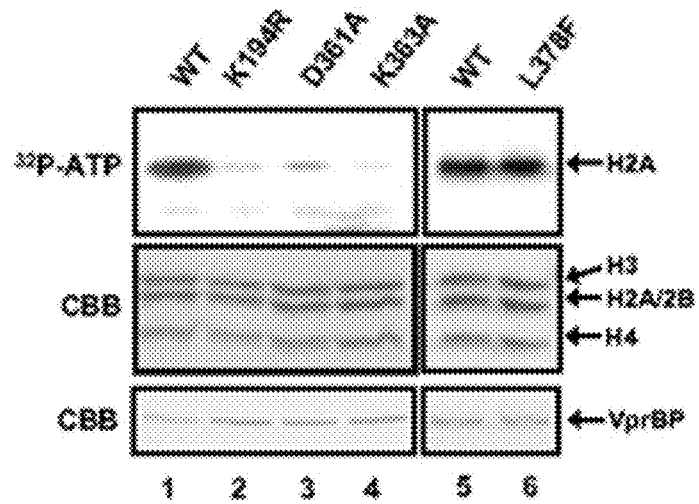
Figure 5J:
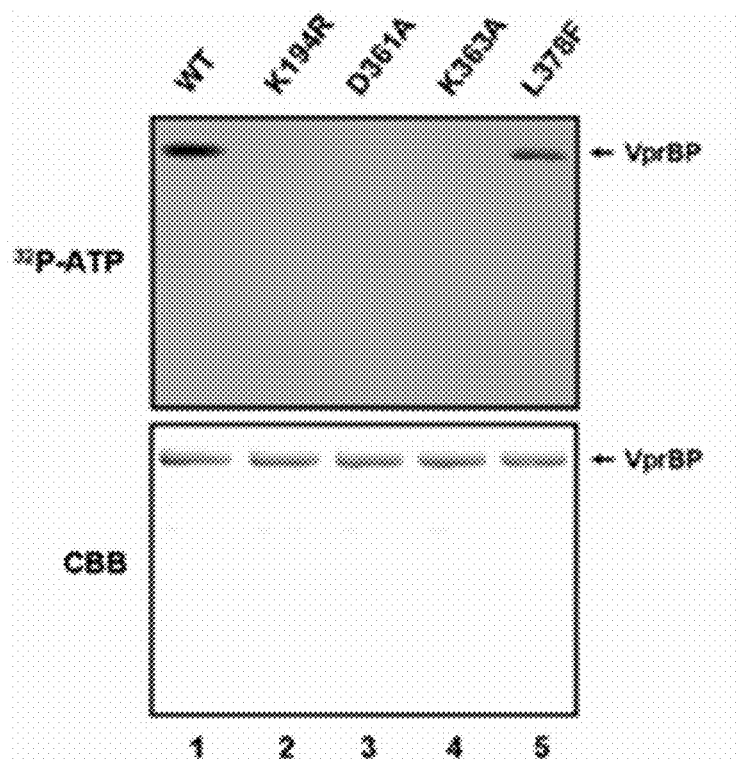
Figure 5K:
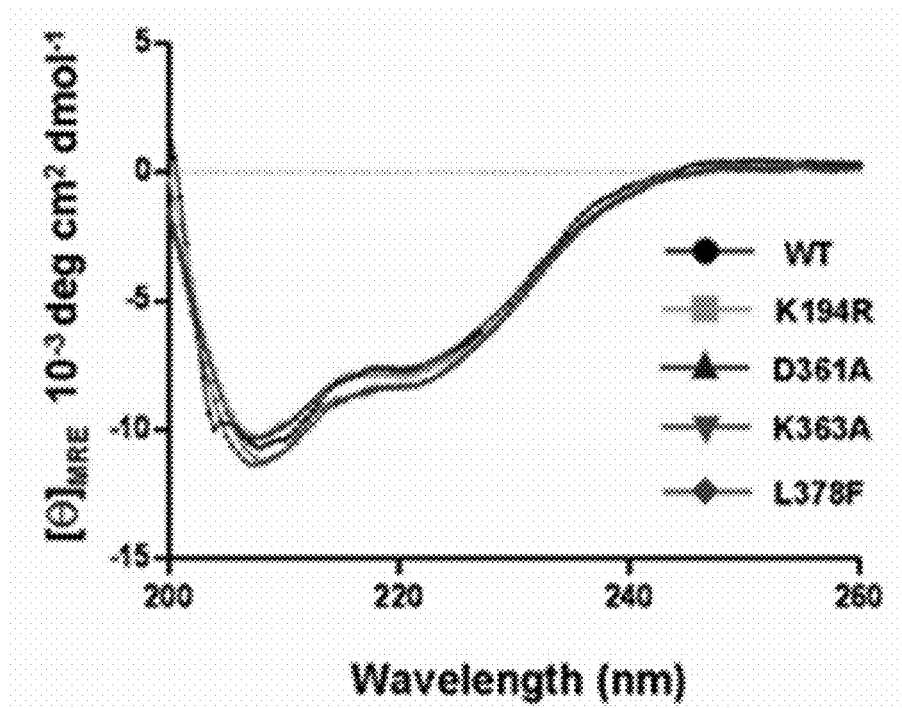

Consistent with these findings, sequence alignments with CK1 and Mut9p kinases identified 8 out of the 12 protein kinase subdomains (Hanks, S. K. et al. (1988) Science 241: 42-52; Taylor, S. S. et al. (1992) Annu Rev. Cell Biol. 8:429-462) in the N-terminal region of VprBP (FIG. 1D, residues 141-500). The lysine residue in the subdomain II is critical for kinase enzymatic activity (Casas-Mollano, J. A. et al. (2008) Proc. Natl. Acad. Sci. USA 105:6486-6491; Zhai et al., 1992). VprBP does not have this conserved residue in its subdomain II but has lysine 194 immediately adjacent to the subdomain II. Notably, mutation of this lysine residue completely abrogated kinase activity (FIG. 1E, lanes 1 and 2; FIG. 5J, lanes 1 and 2). Mutation at either D361 or K363 that is conserved in the subdomain VI also impaired the catalytic activity (FIG. 1E, lanes 3 and 4; FIG. 5J, lanes 3 and 4). On the contrary, mutation of L378 lying outside the conserved subdomains did not affect VprBP kinase activity (FIG. 1E, lane 6; FIG. 5J, lane 5). These results exclude the possibility that the observed H2AT120p is due to a contaminating kinase in the preparation of recombinant VprBP. All VprBP mutants exhibited circular dichroism spectra almost identical to those of the wild-type VprBP (FIG. 5K), thus ruling out the possibility that the altered structure of the VprBP mutants is responsible for their reduced kinase activity.

Figure 1F:
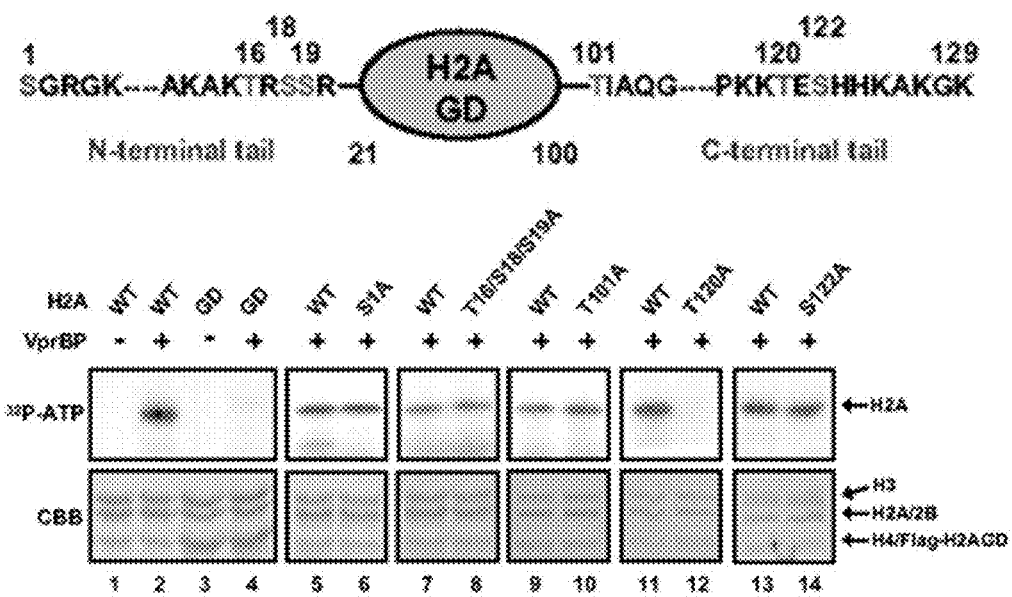
Figure 1G:
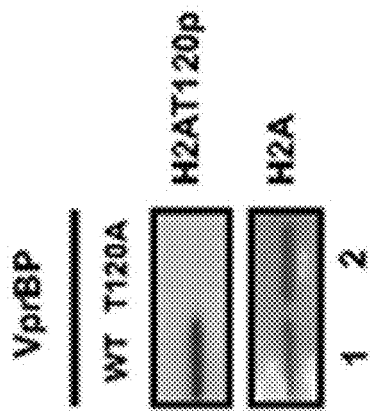

In determining VprBP phosphorylation sites in H2A, Applicants found that simultaneous deletion of the N- and C-terminal tails of H2A blocks H2A phosphorylation by VprBP (FIG. 1F, lanes 1-4). Moreover, VprBP-mediated phosphorylation is completely abolished by mutation of T120, whereas mutations of six other potential modification sites on the tail domains had little effect (lanes 5-14). Western blot analysis of the kinase reactions using anti-H2AT120p antibody further confirmed that VprBP stimulates the phosphorylation of H2AT120 in the nucleosome (FIG. 1G).

Figure 2A:
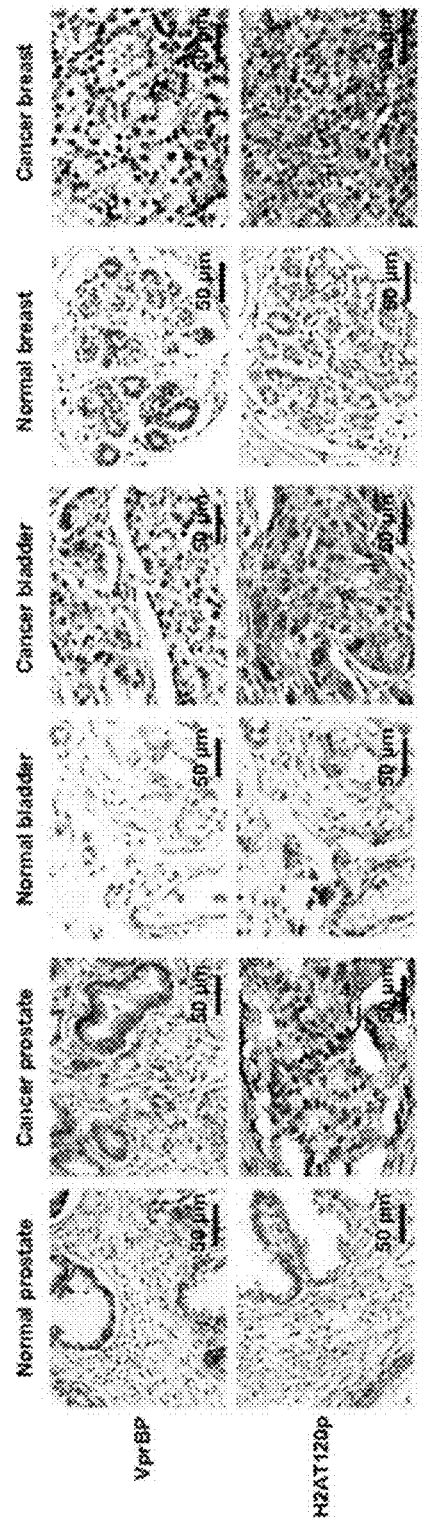
FIGS. 2A-2D show that VprBP is overexpressed in tumors and required for cell proliferation.
Figure 2B:
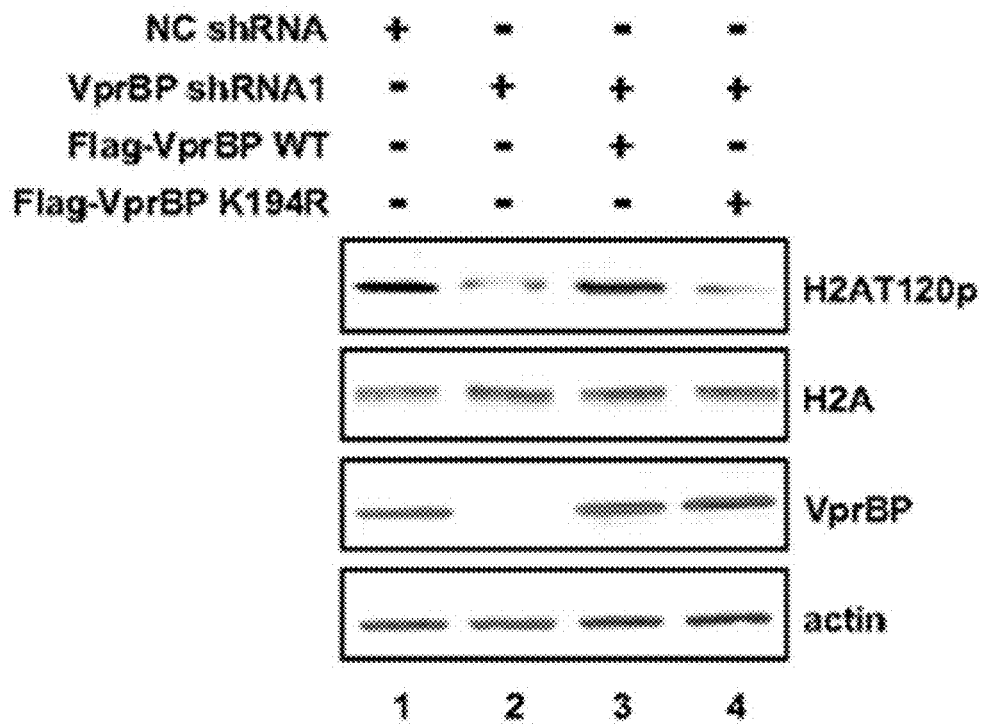
Figure 2C:
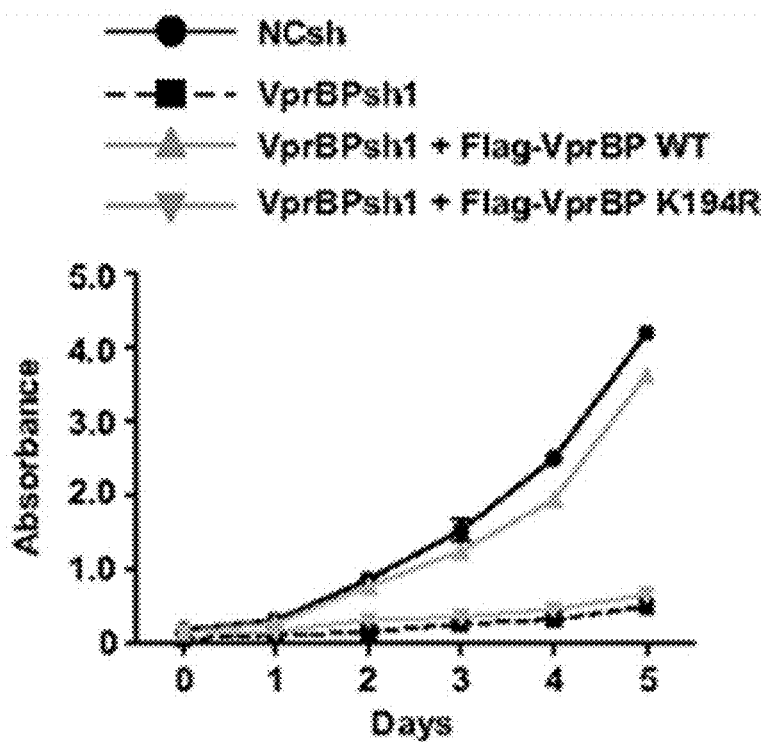
Figures 2D, 3A:
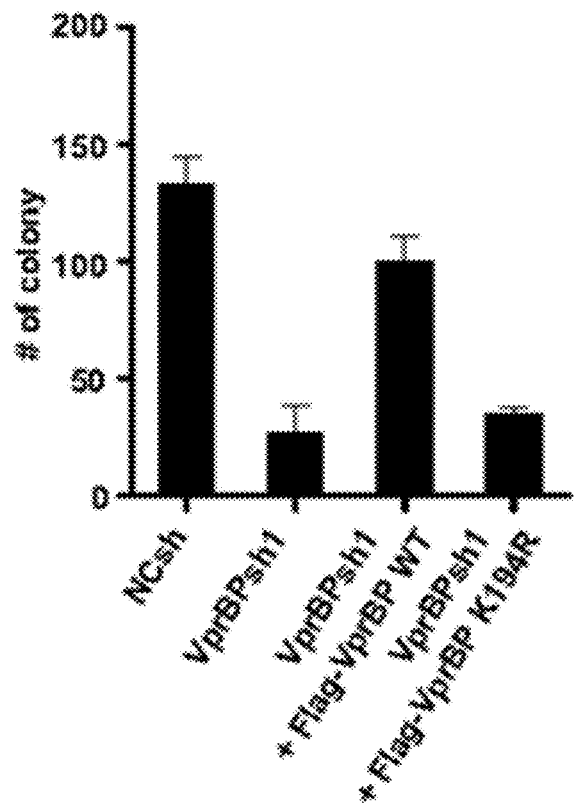
FIGS. 3A-3E show functional analysis of VprBP-mediated H2AT120p.
Figures 6A, 6B:
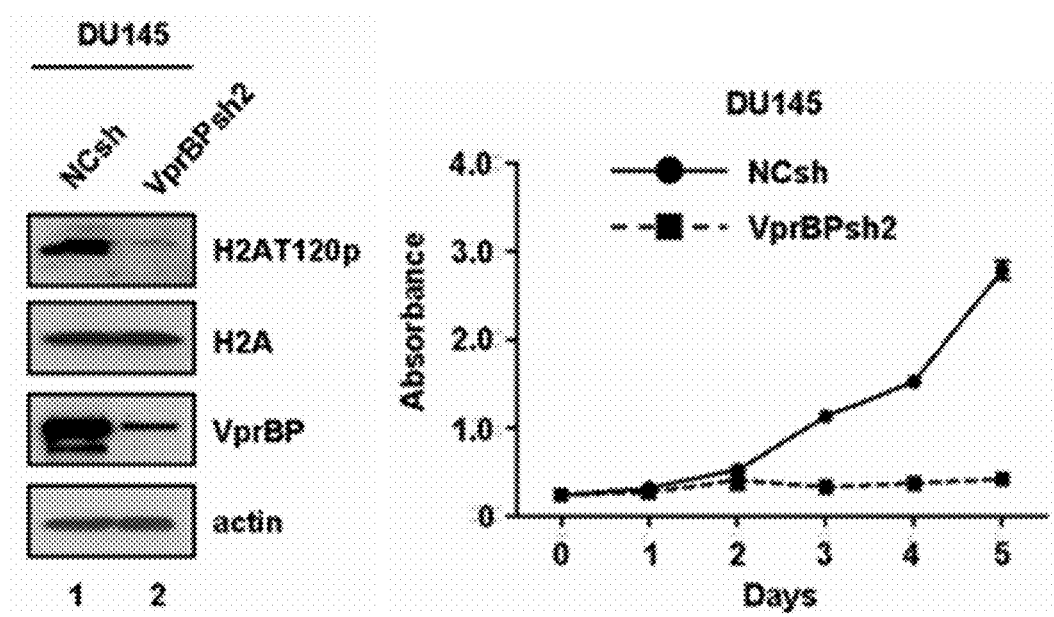
FIGS. 6A-6F show effects of knockdown and overexpression VprBP on cell proliferation, related to FIG. 2.
Figure 6C:
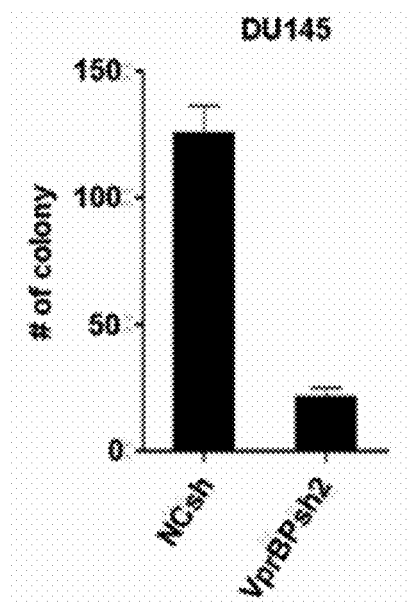
Figure 6D:
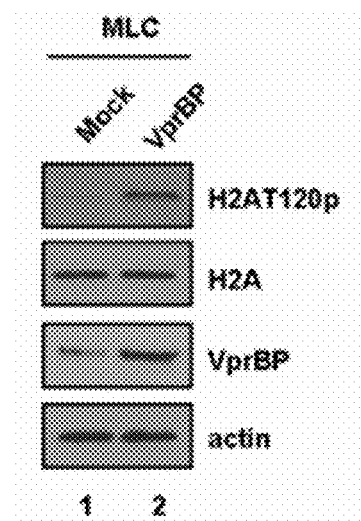
Figure 6E:
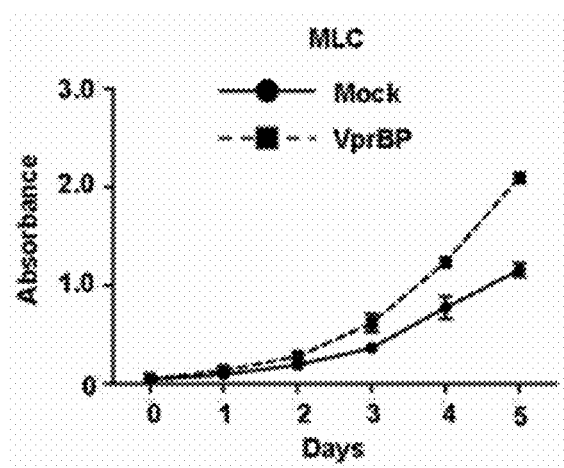
Figure 6F:
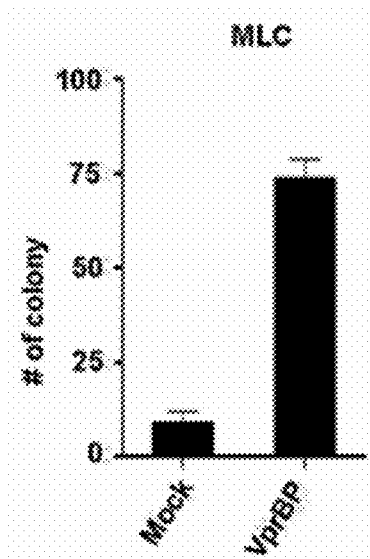

VprBP-Mediated H2AT120p is Highly Abundant in Tumors and Necessary for Cancer Cell Proliferation To decipher the clinical significance of VprBP-mediated H2AT120p, Applicants next analyzed the levels of VprBP and H2AT120p in multiple patient-matched normal and tumor tissue microarray (FIG. 2A; Table 1). Immunohistochemical analysis on 16 types of organ cancer with matched adjacent normal tissue demonstrated a clear link between elevated expression of VprBP and increased levels of H2AT120p in more than 70% of the tumor samples. This trend was more evident in bladder, breast, and prostate tumor samples. In cases where there was no change in VprBP expression, the same trend was observed for H2AT120p. These findings validate the results from cell lines and support the conjecture that VprBP possesses oncogenic properties and its kinase activity contributes to the observed changes. To address this issue, Applicants tested the effects of VprBP depletion on the proliferation of DU145 cancer cells. Expectedly, much lower levels of VprBP were detected in VprBP-depleted cells compared to mock-depleted cells, and the observed reduction of VprBP correlated well with decreased H2AT120p (FIGS. 2B and 6A). MTT assays over a 5-day time course also revealed that VprBP depletion gradually decreased the viability of cancer cells and that the expression of VprBP wildtype, but not VprBP K194R kinase-dead mutant, restored H2AT120p and cell proliferation rates (FIGS. 2C and 6B). Analogously, VprBP depletion interfered with cell proliferation and thus reduced the number of colony-forming cells; colony numbers increased to about 75% of undepleted cells after the expression of wild-type but not K194R-mutated VprBP in the depleted cells (FIGS. 2D and 6C). Consistent with these observations, VprBP overexpression in MLC cells containing low levels of VprBP increased H2AT120p, thereby facilitating cell proliferation and colony formation (FIGS. 6D-6F).

VprBP-Mediated H2AT120p Inactivates Cell Growth Regulatory Genes

Figure 7A:
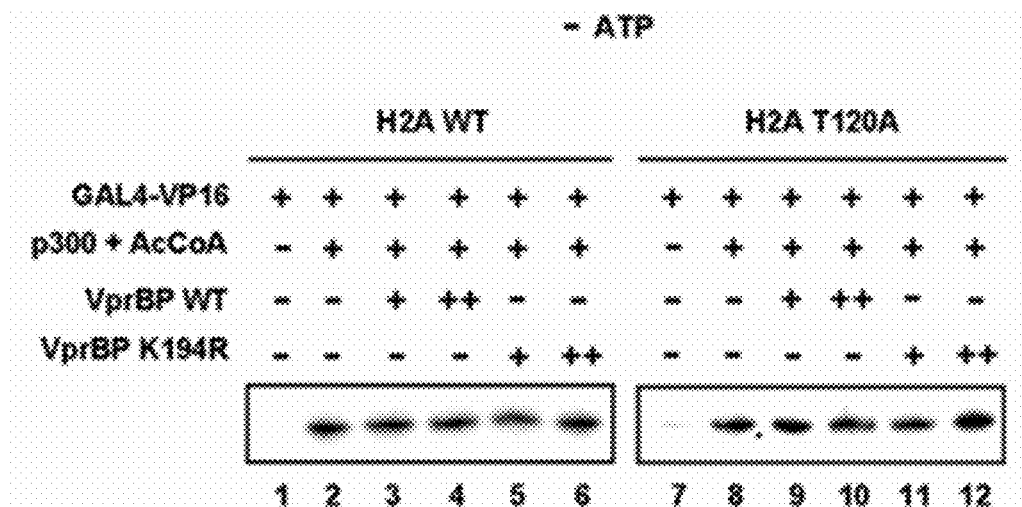
FIGS. 7A-7C show that H2AT120p is required for the transrepression activity of VprBP, related to FIG. 3.

As VprBP has been reported to act as a negative regulator of chromatin transcription (Kim, K. et al. (2012) Mol. Cell. Biol. 32:783-796), Applicants sought to determine whether H2AT120p is required for VprBP function. In the absence of VprBP, high levels of transcription from chromatin reconstituted from G5ML-601 array DNA and recombinant histones were achieved by Gal4-VP16 and p300 (FIG. 3A, lanes 1 and 2). When chromatin was phosphorylated by VprBP, significant repression of transcription was evident (lanes 3 and 4). Intriguingly, however, the ability of VprBP to block transcription was compromised upon mutation of H2AT120 in chromatin (lanes 9 and 10) or omission of ATP from the reaction (FIG. 7A). Furthermore, addition of VprBP kinase-dead mutant to transcription reactions had no detectable effect on transcription (FIG. 3A, lanes 5, 6, 11, and 12), strongly arguing that H2AT120p is the cause of the observed repression.

Figure 3B:
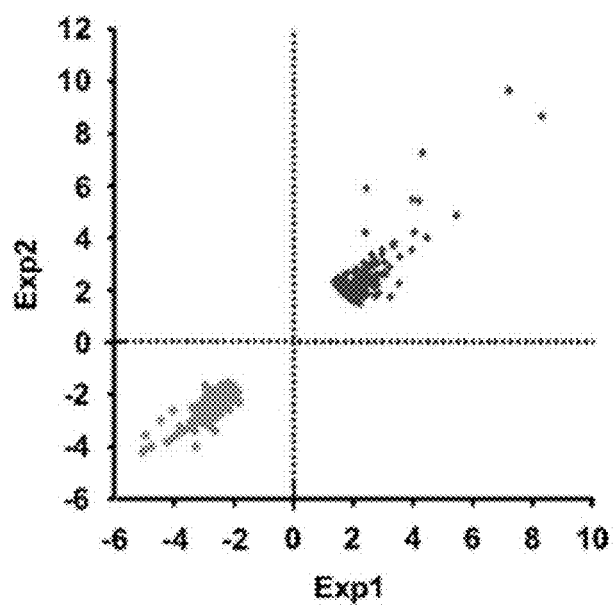
Figure 3C:
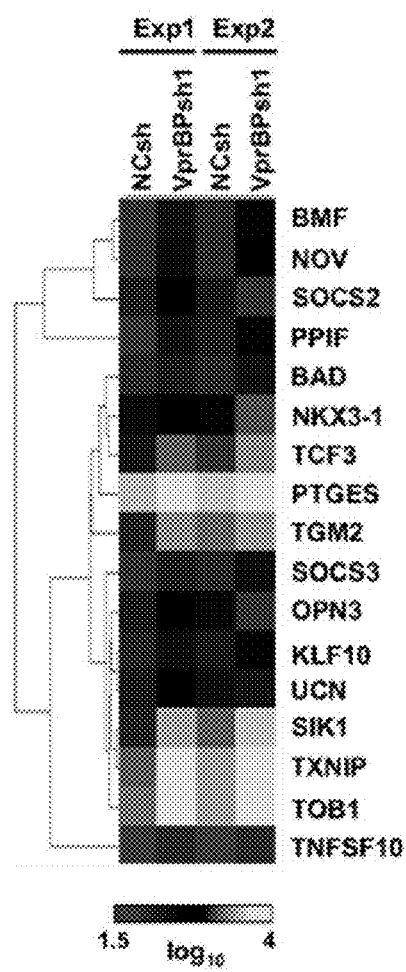
Figure 3D:
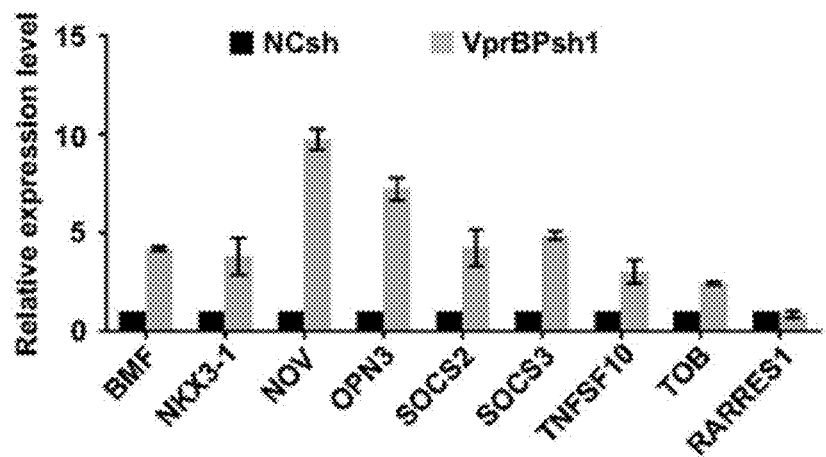
Figure 3E:
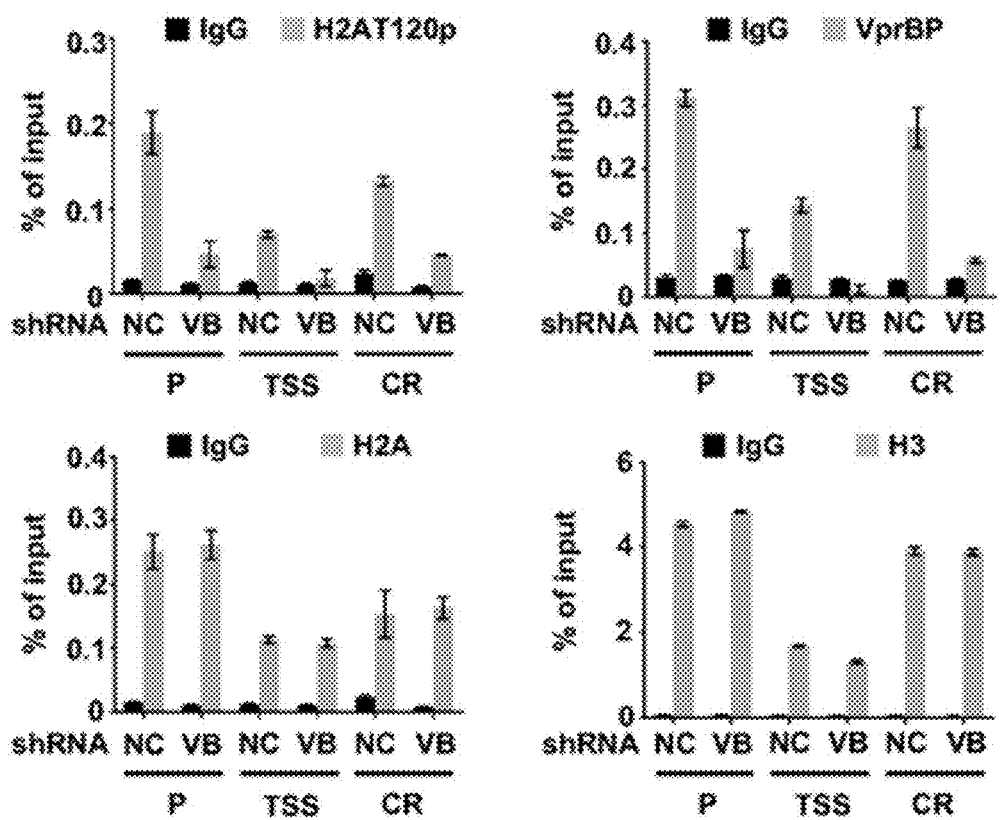
Figure 7B:
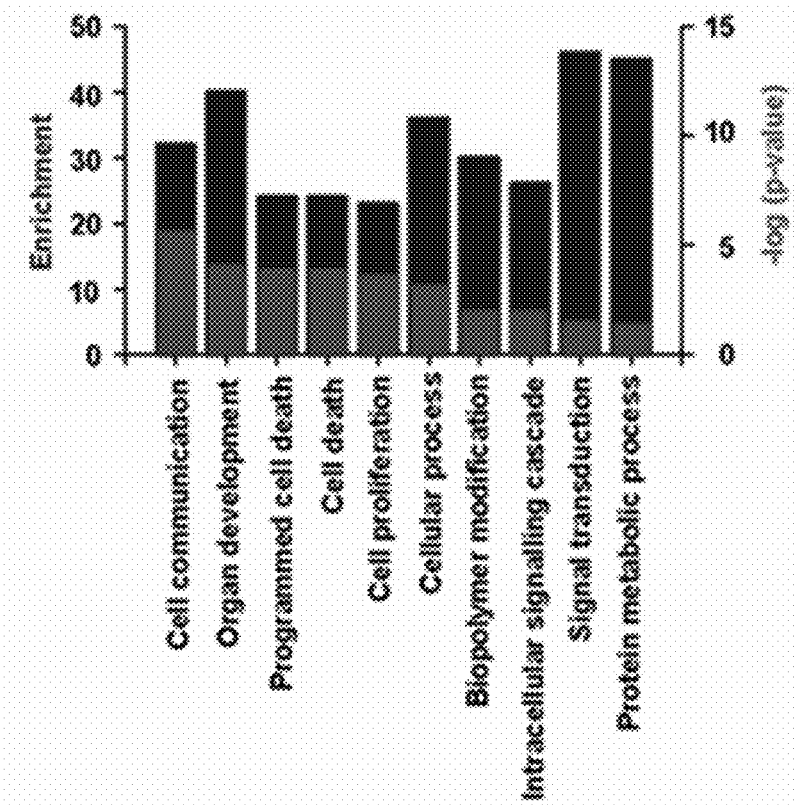
Figure 7C:
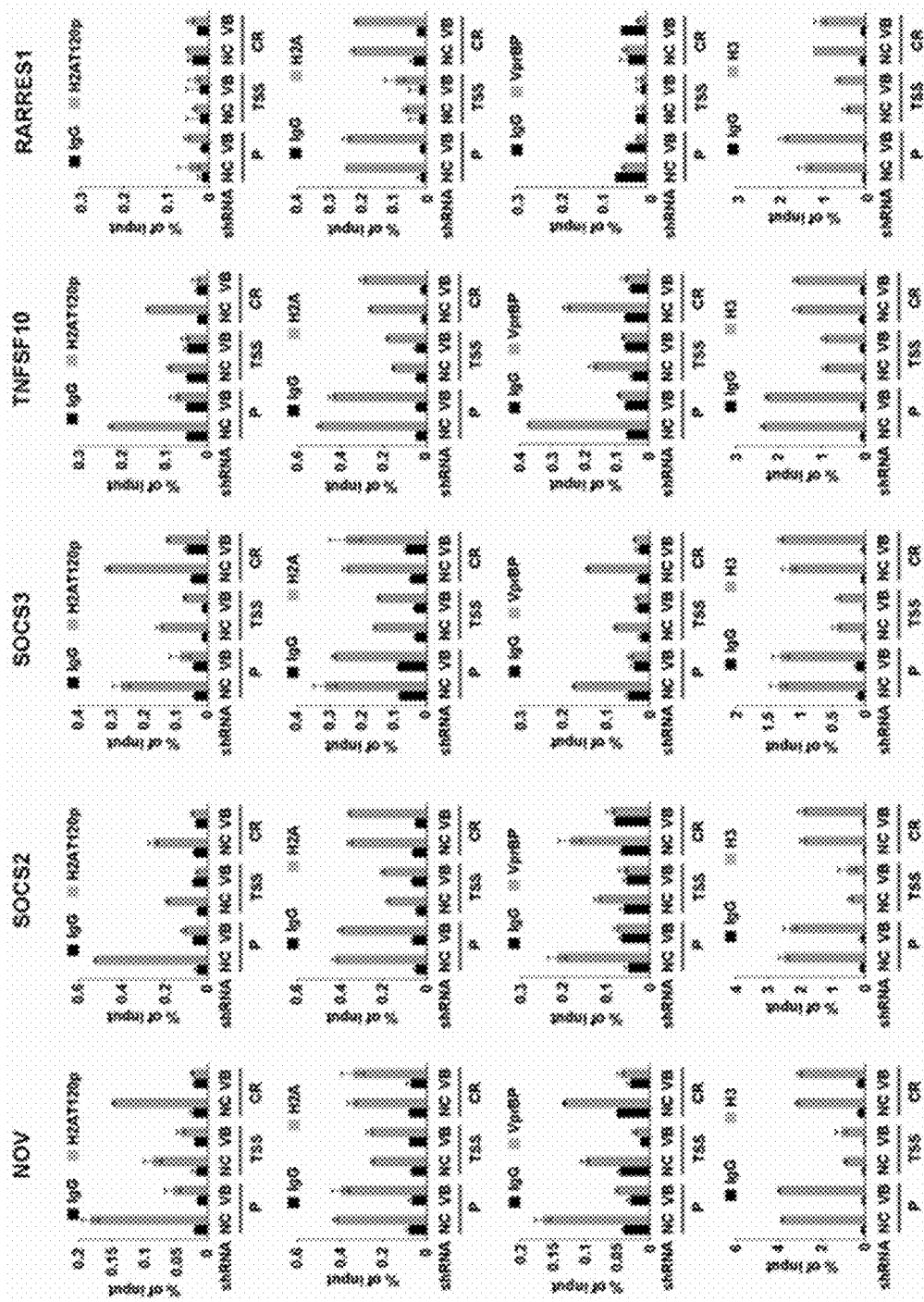

Next, Applicants performed comprehensive microarray analysis with total RNA isolated from mock- or VprBP-depleted DU145 cancer cells. With a fold-change cutoff of >1.7 and stringent p<0.005, the gene expression profiling showed that 292 genes were activated and 208 genes were repressed (FIG. 3B; Tables 2 and 3) in response to VprBP knockdown. Many of the genes upregulated upon VprBP depletion encode cell proliferation and growth regulators (FIG. 7B), including those known to be key regulatory components for cancer initiation and progression (FIG. 3C). The transcriptional changes detected by microarray were validated by qRT-PCR of eight genes whose expression was increased upon VprBP depletion, and one unaffected control gene (FIG. 3D). To check whether the candidate target genes harbor VprBP and H2AT120p, Applicants conducted ChIP assays. In mock-depleted cells, VprBP occupied the promoter and coding regions of the target genes, and H2AT120p showed similar distribution across the loci (FIGS. 3E and 7C). Consistent with previous studies (Schones, D. E. et al. (2008) Cell 132: 887-898), nucleosomes are depleted in the vicinity of a transcription start site (TSS), as indicated by the low levels of H2A and H3. For this reason, ChIP analysis exhibited low levels of VprBP and H2AT120p over the TSS of the target genes. Importantly, VprBP depletion resulted in greatly reduced levels of VprBP and concomitant loss of H2AT120p at the candidate target genes, reinforcing the conclusion that H2AT120p observed in these genes is dependent of VprBP. In the case of the RARRES1 gene, which is not affected by VprBP knockdown (FIG. 3D), the H2AT120p levels were low and remained unchanged under control and VprBP knockdown conditions (FIG. 7C).

B32B3 is a Potent and Selective Inhibitor of VprBP and Suppresses Tumor Growth

Figure 4A:
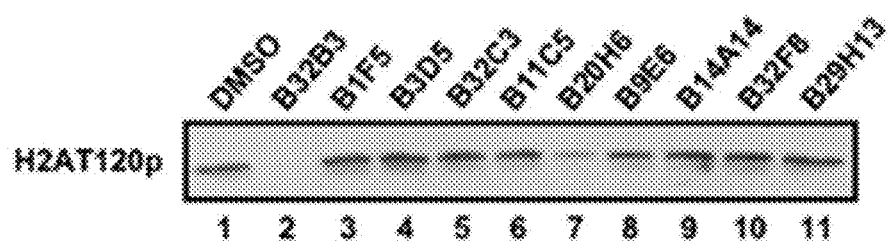
Figure 4B:
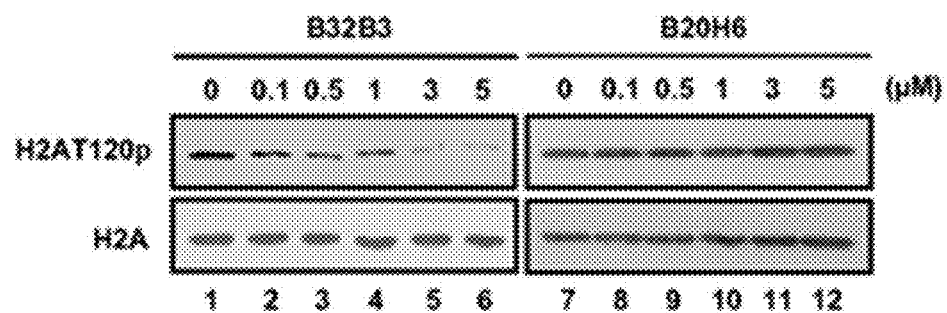
Figure 4C:
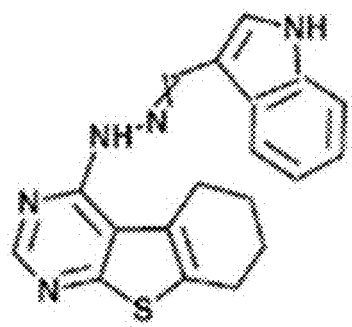
Figure 4D:
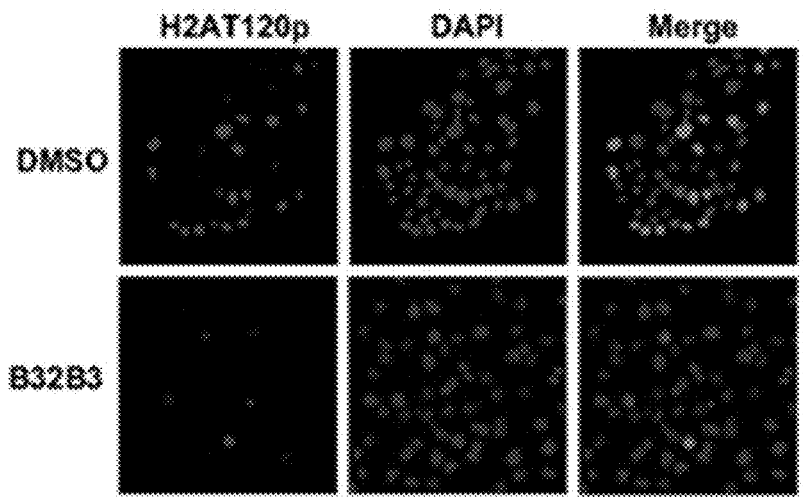
Figure 4E:
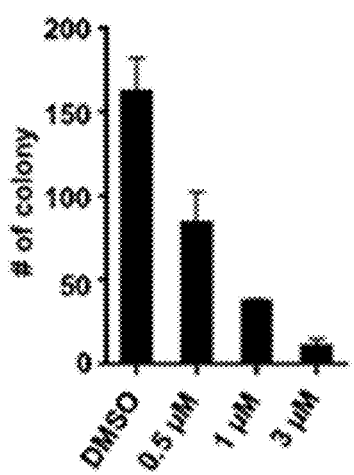
Figure 8A:
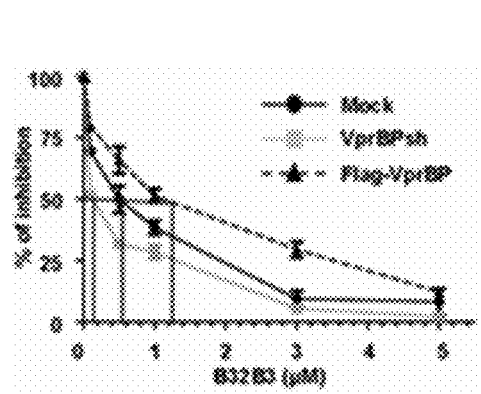
FIGS. 8A-8I show characterization of B32B3 as a small-molecule VprBP kinase inhibitor, related to FIG. 4.
Figure 8B:
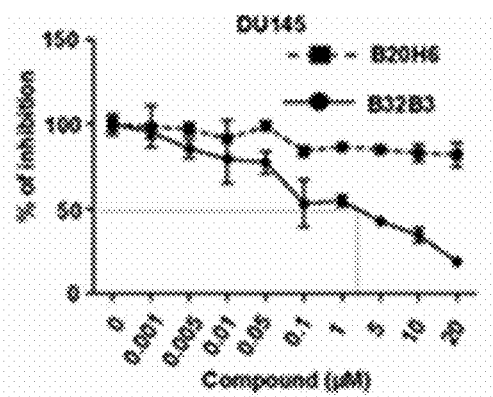
Figure 8C:
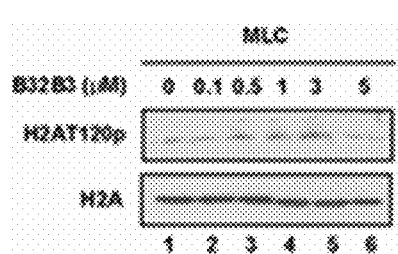
Figure 8D:
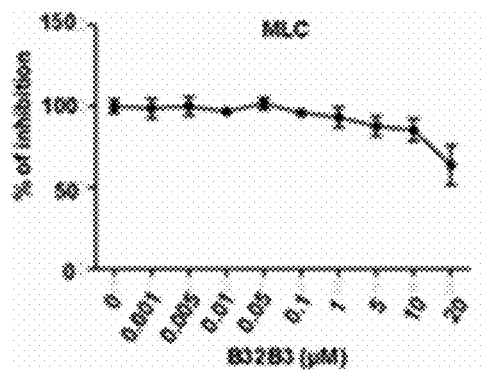
Figure 8E:
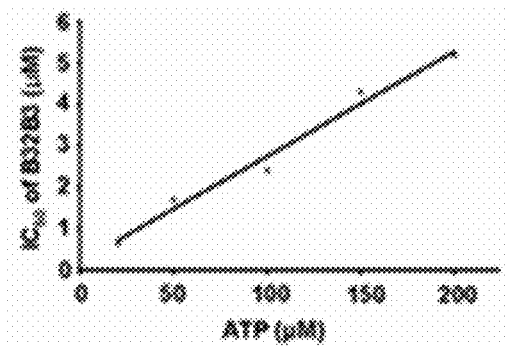

The fact that VprBP knockdown abrogates H2AT120p and slows cancer cell growth prompted us to look for highly potent and selective inhibitors for VprBP. To this end, Applicants' inhouse small-molecule library of 5,000 compounds was screened. When the inhibitory potential of the compounds was assessed by in vitro kinase assays, two of them (0.002% hit rate), designated as B32B3 and B20H6, inhibited VprBP and decreased H2AT120p at a concentration of 5 mM (FIG. 4A). To evaluate their cellular effects, DU145 cells were treated with the compounds in the concentration range of 0-5 mM for 24 hr. B32B3 potently inhibited H2AT120p with a half-maximal inhibitory concentration (IC50) value of 0.5 mM, as evaluated by western blotting and immunostaining (FIGS. 4B, 4D, and 8A). The observed reduction in H2AT120p was paralleled by inhibition of cell proliferation (FIGS. 4E and 8B). By comparison, B20H6 failed to produce any detectable changes in H2AT120p and cell growth after treatment (FIG. 4B, lanes 7-12; and FIG. 8B), suggesting that this compound might be relatively unstable with poor cellular uptake. Importantly, the knockdown of VprBP sensitized DU145 cells to B32B3 with a circa 2-fold decrease in the IC50, whereas B32B3 was considerably less potent in DU145 cells overexpressing VprBP (FIG. 8A). Furthermore, B32B3 treatment at concentrations up to 5 mM minimally antagonized the proliferation of MLC cells lacking VprBP-mediated H2AT120p (FIGS. 8C and 8D). These results indicate that B32B3 preferentially targets cancer cells exhibiting high levels of VprBP and H2AT120p. That the IC50 value of B32B3 was increased in the presence of incremental concentrations of ATP argues strongly that B32B3 competes with ATP and may bind to the kinase active site (FIG. 8E). Additionally, when tested against a panel of 33 human kinases, B32B3 showed greater than 100-fold selectivity for VprBP over 33 other kinases with an IC50 of 0.6 mM (Table 4). Thus, although Applicants cannot exclude the possibility that other kinases that were not included in the selectivity screen might be affected, B32B3 can be defined as a highly specific VprBP inhibitor at present.

Figure 4F:
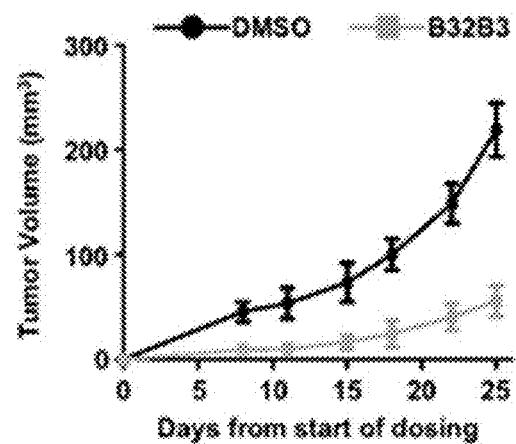
Figure 4J:
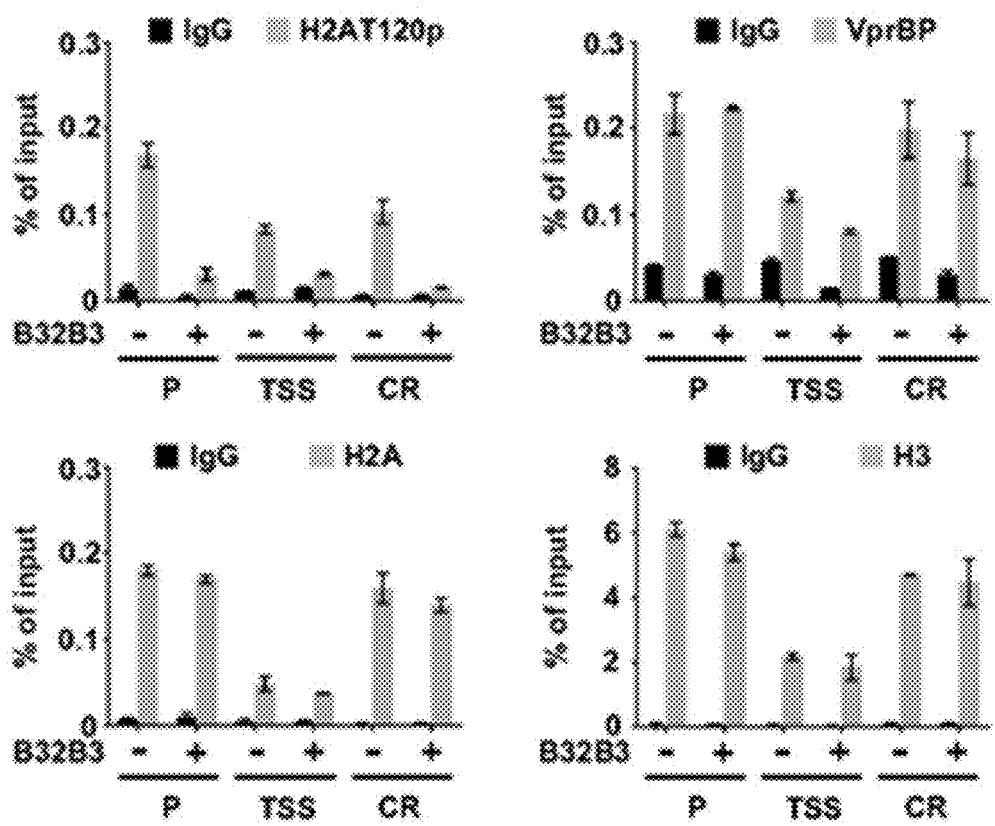
Figure 8F:
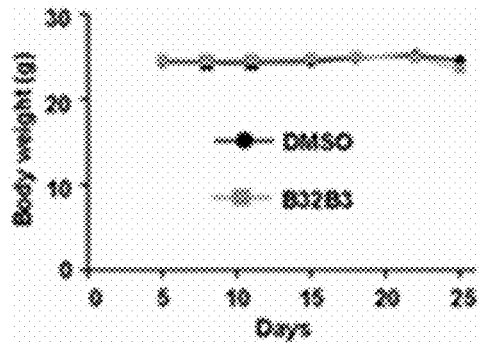
Figure 8G:
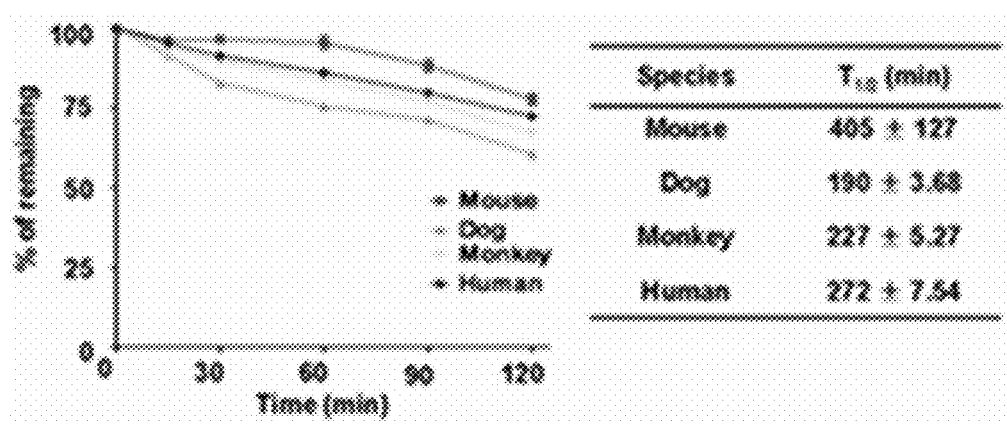
Figure 8H:
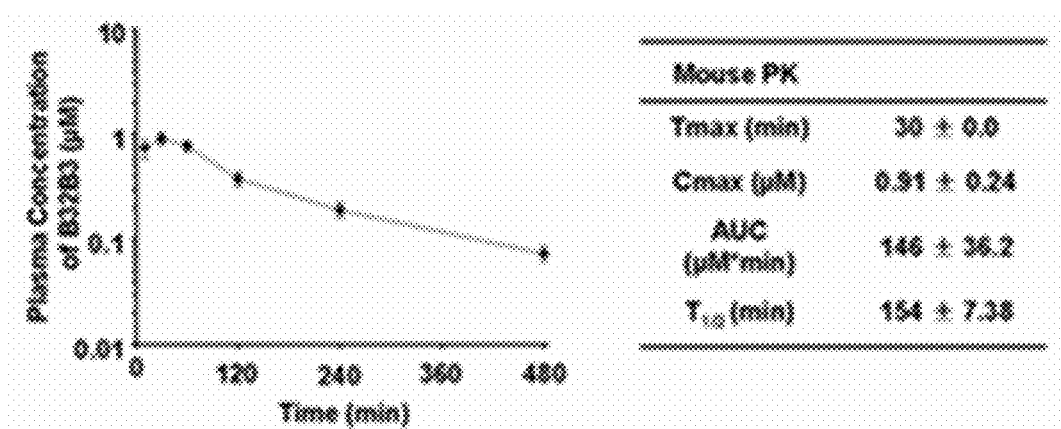
Figure 8I:
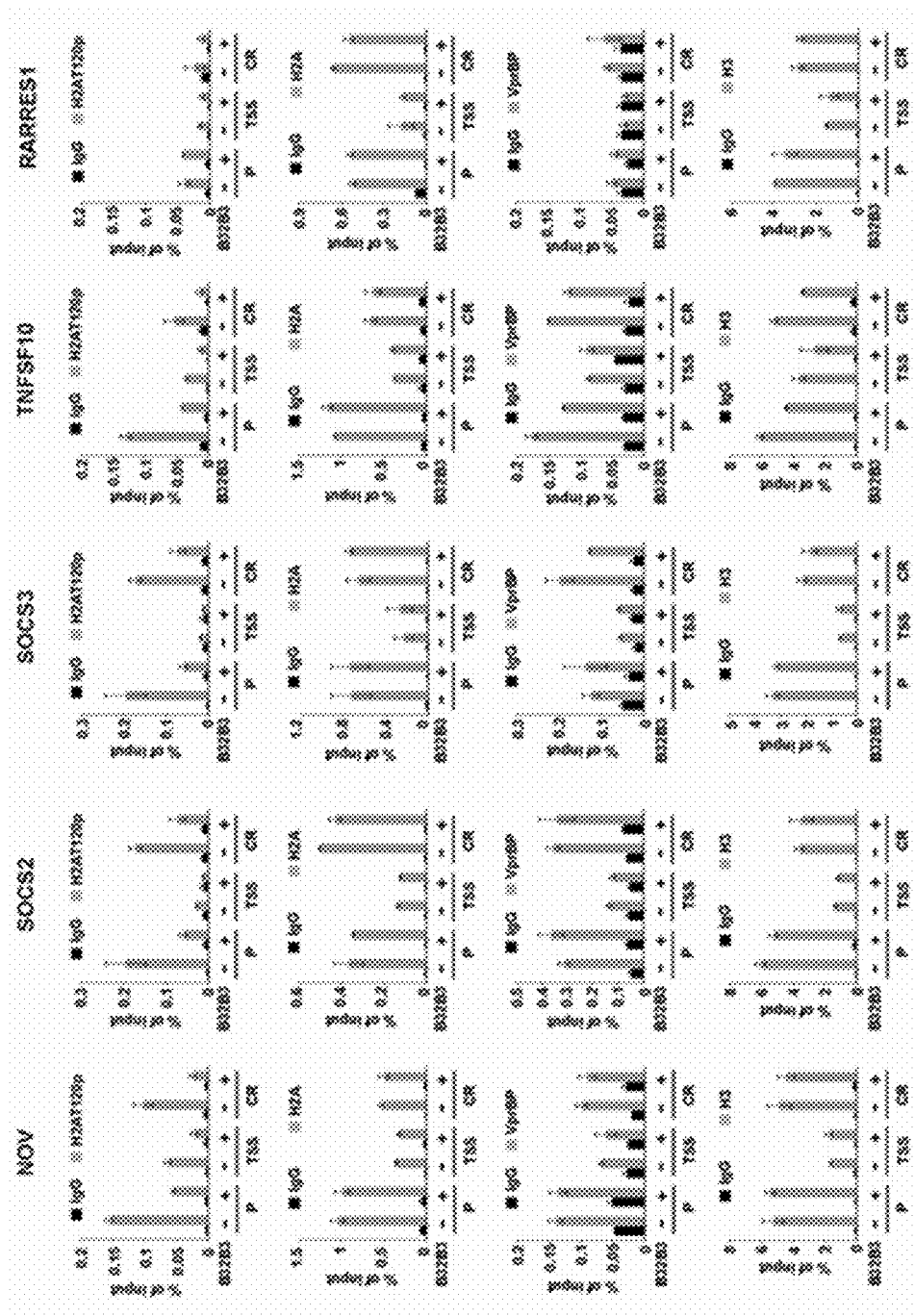
Figure 9:
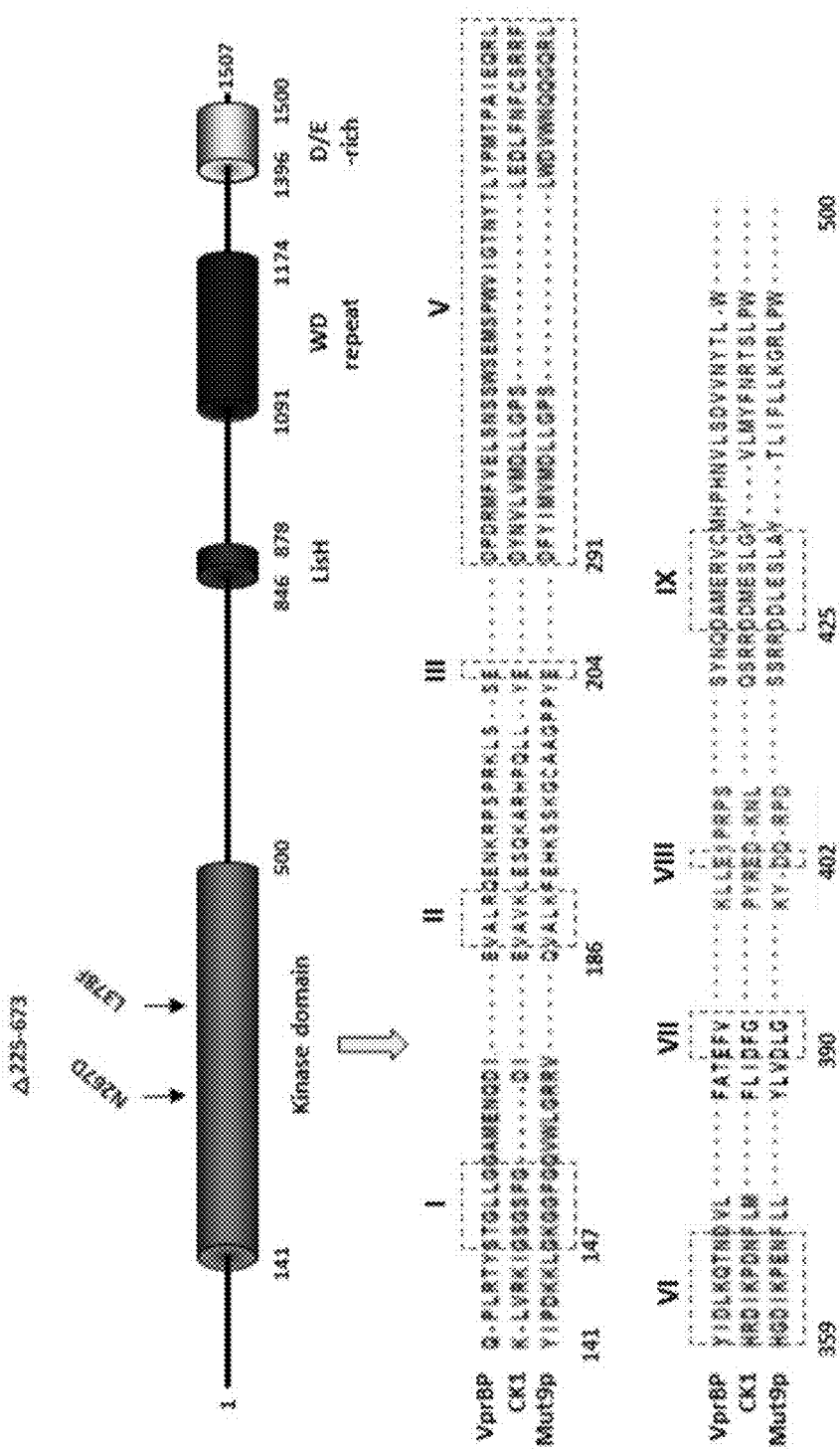
FIG. 9 shows domain architecture and known mutation sites of VprBP. VprBP contains the putative kinase domain in the N-terminus and the L is homology motif, WD repeats and D/E rich domains in the C-terminus. Numbers denote amino acid positions. The positions of known mutation in the kinase domain are indicated by letters along with their positions.
Figure 10:
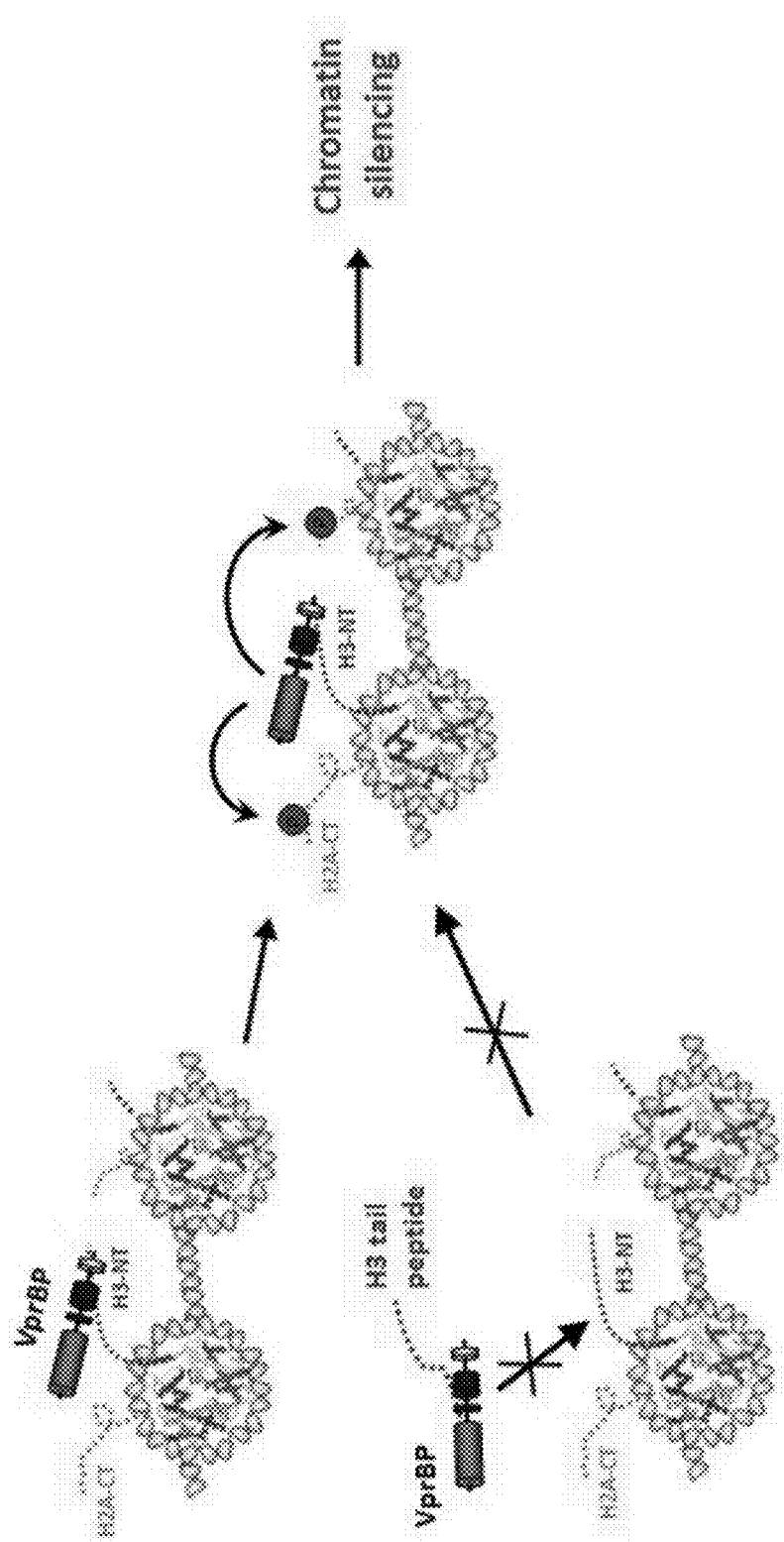
FIG. 10 shows VprBP functions in chromatin silencing. VprBP is localized onto specific chromatin regions via its interaction with the H3 N-terminal tail (NT) and phosphorylates H2A C-terminal tail (CT) at T120 to establish a repressive chromatin state. Thus free H3 tail peptides can prevent VprBP from binding to the nucleosome and thereby inhibit H2AT120 phosphorylation reactions.

A key question that arises from our findings is whether B32B3 exhibits antitumor efficacy through its VprBP inhibitory activity. To address this question, Applicants inoculated 1 3 107 DU145 cancer cells into nude mice and treated tumor xenografts with intraperitoneal injections of B32B3 at a dose of 5 mg/kg twice a week over 3 weeks. Tumor growth was inhibited, as calculated the day after the last treatment of B32B3, by 70%-75% (FIGS. 4F and 4G). At these doses, B32B3 appeared to be well tolerated in mice, and it did not cause any significant weight loss during treatment (FIG. 8F). In evaluating the pharmacokinetic properties of B32B3, Applicants found that B32B3 has a half-life of approximately 7 hr in mouse plasma and a Cmax of 1 mM at a dose of 5 mg/kg in mice (FIGS. 8G and 8H). To correlate B32B3 antitumor activity with VprBP inhibition, DU145 xenograft tumors explanted from DMSO- or B32B3-treated mice were analyzed by immunohistochemistry. The levels of H2AT120p were greatly decreased in the tumors of B32B3-treated mice, compared to DMSO-treated controls (FIG. 4H). To elucidate the mechanistic basis of the B32B3 effects, Applicants tested if the compound could rescue the transcriptional inhibition caused by VprBP. As summarized in FIG. 4I, treatment of DU145 cells with B32B3 (1 mM) resulted in, albeit to a varying extent, higher expression of VprBP target genes. Because H2AT120p is essential for VprBP transrepression, Applicants also examined the effects of B32B3 on H2AT120p at the target genes. VprBP was present at high levels at both promoter and coding regions, which did not alter upon B32B3 treatment. However, H2AT120p at the regions was reduced by 70%, following B32B3 treatment at the same dose (FIGS. 4J and 8I). B32B3 thus displays anticancer properties at least in part, by interfering with VprBP-mediated H2AT120p at the target genes.

Discussion

Figures 5L, 5M:
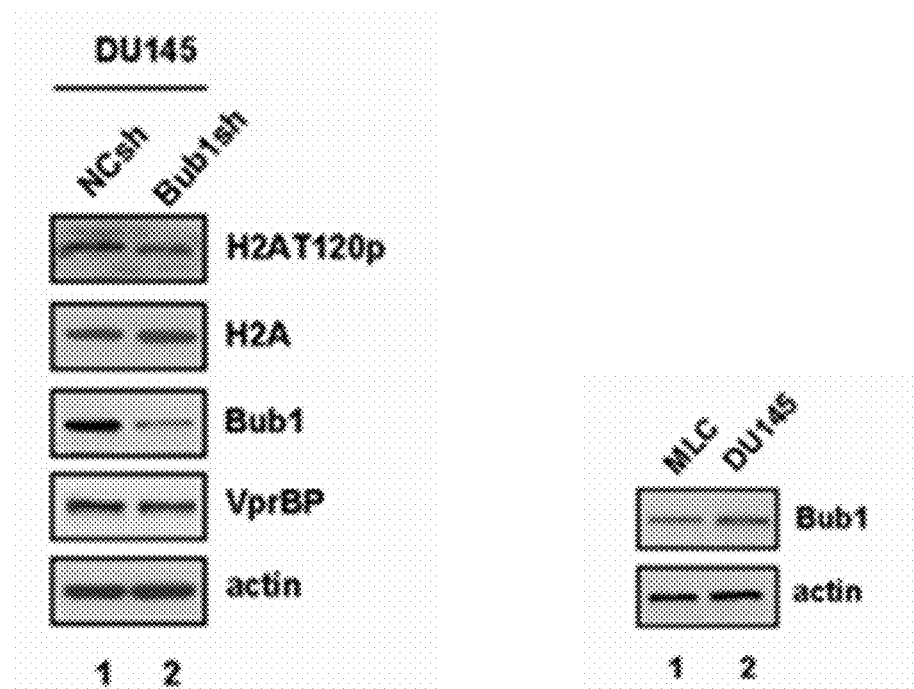

This work describes the systematic biochemical and cellular analysis of VprBP and unveils a surprising mechanism underlying the formation of repressive chromatin by VprBP. A key finding is that the N-terminal region of VprBP possesses a previously unrecognized kinase activity for H2AT120. VprBP contains 8 out of the 12 conserved protein kinase subdomains, and mutations of these subdomains abolish the catalytic activity, further confirming that VprBP is a bona fide protein kinase. Interestingly, while most histone kinases identified so far are incapable of phosphorylating nucleosomal histones, VprBP displays an unusual additional activity as an effective kinase of nucleosomes. In this respect, VprBP resembles *Drosophila* NHK-1, which catalyzes phosphorylation of H2AT119 (equivalent to human H2AT120) in the nucleosomal context (Aihara, H. et al. (2004) Genes Dev. 18:877-888). It has been reported that Bub1 acts as a centromere-specific kinase for H2AS121 (H2AT120 in human) during prometaphase and metaphase in fission yeast (Kawashima, S. A. et al. (2010) Science 327:172-177). Applicants' attempts to detect any significant changes in H2AT120p in Bub1-depleted DU145 cells have been unsuccessful (FIG. 5L), probably because Applicants have used unsynchronized interphase cells. Applicants also observed that Bub1 is expressed at similar levels in MLC normal and DU145 cancer cells (FIG. 5M). It thus appears that the role of VprBP-mediated H2A phosphorylation is distinct from that of Bub1-mediated H2A phosphorylation. Further structural and biological analyses of VprBP and Bub1 would be helpful for understanding the functional differences of these two kinases.

There has been no demonstration that H2AT120p is involved in the regulation of gene expression, although recently this possibility has been discussed. Our well-defined in vitro assay system allows us to provide the first direct connection between H2AT120p and transcriptional repression. Importantly, blocking VprBP-mediated H2AT120p by point mutation, Applicants have been able to verify that H2AT120p is a critical determinant of repressive action of VprBP. In accord with these in vitro data, gene expression profiling demonstrated that VprBP down-regulates 292 genes, many of which are involved in cell proliferation and programmed cell death. An intriguing question raised by these results is how H2AT120p by VprBP modulates chromatin transcription. One possible mechanism is that H2AT120p can affect the occurrence of other histone modifications on the same or different histone tails. Recent work from our lab has shown that VprBP interacts with HDAC1, thereby inhibiting H3 acetylation at p53 target genes (Kim, K. et al. (2012) Mol. Cell. Biol. 32:783-796). This suggests that H2AT120p at target genes may influence HDAC1 activity required for gene repression. Another possibility is that H2AT120p could serve as an integrating platform for repressor proteins. Considering the fact that the centromere cohesion protector shugoshin recognizes H2AT120p and recruits heterochromatin protein Swi6/HP1 at centromeres in fission yeast (Kawashima, S. A. et al. (2010) Science 327:172-177; Yamagishi, Y. et al. (2008) Nature 455:251-255), the recruitments of factors to specific chromatin domains are likely to be part of the mechanisms for VprBP-induced gene silencing. Another question unsolved in our study is how VprBP is initially localized at target genes. A likely model is that VprBP physically associates with gene specific factors to influence the transcription of target genes, as supported by our recent finding that VprBP-p53 interaction is a key event in VprBP action on p53 target genes (Kim, K. et al. (2012) Mol. Cell. Biol. 32:783-796). Thus, more extensive studies of VprBP interaction with DNA-binding factors and other coregulators would provide a molecular explanation to gene-specific function of VprBP.

VprBP expression is significantly higher in breast, bladder, and prostate cancer tissues compared to their benign counterparts. The observation that VprBP knockdown significantly decreased H2AT120p and cancer cell growth indicates that VprBP could be an ideal target for cancer therapy. As the first step toward checking this possibility, Applicants screened large numbers of compounds in a high-throughput manner and identified B32B3 as a selective inhibitor of VprBP. B32B3 is thought to inhibit VprBP kinase activity by competing with ATP. Importantly, B32B3 recapitulates the most molecular phenotypes that arise from VprBP knockdown: (1) the reduction of H2AT120p at target genes, (2) higher expression of VprBP target genes, and (3) the impairment of cancer cell growth. Thus, B32B3 represents a unique tool to investigate the regulatory pathways governing H2AT120p in physiological and tumorigenic conditions. Moreover, the selectivity for cancer cells in culture and our ability to demonstrate efficacy in a mouse model of VprBP at doses that were well tolerated suggest that inhibition of VprBP by B32B3 may provide a pharmacological basis for therapeutic intervention against cancers.

Experimental Procedures

In Vitro Kinase and Transcription Assays

Recombinant mononucleosomes and nucleosome arrays were reconstituted using recombinant histone octamers as recently described (Jaskelioff, M. et al. (2000) Mol. Cell. Biol. 20:3058-3068; Robinson, P. J. et al. (2008) J. Mol. Biol. 381:816-825). For kinase assays, recombinant VprBP was incubated with free histones (1 mg) or reconstituted nucleosomes (2 mg) in kinase buffer (50 mM Tris-HCl [pH 7.5], 20 mM EGTA, 10 mM $MgCl_2$, 1 mM DTT, and 1 mM b-glycerophosphate) containing 10 mCi of [g-32P] ATP and 4 mM ATP for 30 min at 30_C. Proteins from each reaction were separated by SDS-PAGE, Coomassie blue stained, dried, and visualized by autoradiography. To create VprBP inhibitors, a collection of 5,000 compounds was screened in the same kinase assays at a final concentration of 5 mM. The selectivity of B32B3 toward VprBP kinase was assessed in a panel of 33 kinases listed in Table 4. In vitro transcription assays were as described (Kim, K. et al. (2012) Mol. Cell. Biol. 32:783-796), except that G5ML-601 nucleosome arrays (100 ng) and Gal4-VP16 (15 ng) were used for the reactions. Recombinant VprBP (25 or 50 ng) and ATP (10 mM) were added before p300 (20 ng) and AcCoA (10 mM).

Mice Xenografts

All animal experiments were performed according to protocols approved by the Institutional Animal Care and Use Committee. Tumor xenografts were established by subcutaneous injection of 1 3 107 DU145 cells into 8-weekold female nude mice (n=8). At day 5 after injection, the mice bearing DU145 tumor xenografts were treated with twice-weekly i.p. injections of either DMSO or B32B3 at a dose of 5 mg/kg throughout the duration of the experiment. Tumor dimension was measured by calipers twice a week, and tumor mass was calculated as described (Heo, K. et al. (2012) Oncogene 32:2510-2520). The mice were killed by asphyxiation with $CO2$, and tumors were excised and weighed 25 day after the cell injection. To analyze the H2AT120p, formalin-fixed and paraffin-embedded sections (5 mm) from DU145 tumor xenografts were subject to immunohistochemistry. Animal studies were conducted under approved institutional protocols.

Accession Numbers

The NCBI GEO accession number for microarray data reported in this application is GSE50414.

Cell Culture, Constructs and Antibodies

MDA-MB231, LD611 and DU145 cells were cultured in Dulbecco's modified Eagle's medium (DMEM) supplemented with 10% FBS. MCF-10-2A cells were grown in a 1:1 mixture of DMEM and Ham's F12 supplemented with 20 ng/ml epidermal growth factor, 100 ng/ml cholera toxin, 0.01 mg/ml insulin, 500 ng/ml hydrocortisone, and 5% horse serum. Urotsa cells were grown in DMEM low glucose containing 10% FBS. MLC cells were grown in T medium containing 10% FBS. To express VprBP using the baculovirus system, VprBP cDNA was subcloned into the EcoRI and XhoI sites of pFASTBAC vector with an N-terminal His epitope. To generate VprBP mutants, VprBP cDNA was mutated by the QuikChange® II site-directed mutagenesis kit (Agilent Technologies) before the construction. For mammalian expression of VprBP wild type and mutants, the corresponding cDNAs were amplified by PCR and ligated into the EcoRI and SalI sites of lentiviral expression vector pLenti-Hygro (addgene) containing 5' FLAG coding sequence. For bacterial expression of human H2A proteins, H2A cDNA was inserted into the NdeI and BamHI sites of pET-11a or pET-11d vector in frame with FLAG sequences. Single- or multiple-residue substitutions in H2A were made by QuickChange kit and verified by DNA sequencing. Antibodies specific for H3ac, H4ac, H2Aac, H2Bac, H3K27me3, H3S10p and H2A were from Millipore; antibodies for H3K4me3, H3K9me3 and H2AT120p (for Western blotting) were from Active Motif; antibodies for H3K36me3 and H2AT120p (for immunostaining and ChIP) were from Abcam; antibody for VprBP was from Proteintech Group; antibody for Bub1 was from GeneTex; and antibody for actin was from Sigma.

Chromatin Extraction

Cells were lyzed by suspending in buffer A (10 mM HEPES, pH 7.4, 10 mM KCl, 1.5 mM $MgCl_2$, 0.34 M sucrose, 10% glycerol, 1 mM DTT, 5 mM β-glycerophosphate, 10 mM NaF, protease inhibitor, and 0.2% TritonX-100) and incubating on ice for 8 min. Nuclei were isolated by centrifugation (1,300×g for 10 min at 4° C.), and the supernatant was discarded. The resulting nuclei pellet was resuspended in buffer B (3 mM EDTA, 0.2 mM EGTA, 1 mM DTT, 5 mM β-glycerophosphate, 10 mM NaF, and protease inhibitor) and incubated for 30 min on ice. The suspension was centrifuged (1,700×g for 5 min at 4° C.) and then the pellet was washed with buffer B three times. The chromatin pellet was sonicated in Laemli sample buffer.

Recombinant Proteins

His-VprBP wild type and mutants were expressed using a baculovirus vector in insect (Sf9) cells. The expressed proteins were initially purified with Ni-NTA agarose (Novagen), and further purified with Q Sepharose (GE healthcare) column according to standard procedures. The purity and intactness of the recombinant VrpBP proteins were confirmed by quantitative LC-MS/MS and Western blotting. Recombinant histones were expressed in *Escherichia coli* Rosetta 2 (DE3) pLysS cells (Novagen) and purified as described previously (Dyer, P. N. et al. (2004) Methods Enzymol. 375:23-44).

in-Gel Kinase Assay

In-gel kinase assay was performed as described (Wooten, M. W. (2002) Sci. STKE 2002:115) with minor modifications. Briefly, wild type and mutant VprBP proteins (5 μg) were resolved on an 8% SDS-PAGE gel, and the VprBP proteins in the gel were denatured in denaturation buffer (50 mM Tris-HCl, pH 8.0, 20 mM DTT and 6 M Guanidine HCl) for 1 h at room temperature and were renatured for 16 h at 4° C. in renaturation buffer (50 mM Tris-HCl, pH 8.0, 5 mM DTT, 0.04% Tween-20, 100 mM NaCl and 5 mM MgCl2). The kinase reaction was initiated in 15 ml of kinase buffer (25 mM Hepes, pH 7.4, 20 mM $MgCl_2$, 5 mM NaF, 1 mM DTT) containing 50 μM ATP and 20 Ci of [γ-32P] ATP for 1 h at 30° C. The reaction was terminated by washing the gel with a fixing solution containing 10 mM sodium pyrophosphate and 5% trichloroacetic acid for 2 h. The gel was dried and subjected to autoradiography.

Circular Dichroism (CD) Spectroscopy

CD measurements were recorded using a Jasco J-810 spectropolarimeter with a 0.1 cm pathlength cuvette and a protein concentration of 1 μM. Circular dichroism spectra were obtained at 25° C. in phosphate buffer (10 mM sodium phosphate and 50 mM NaCl, pH 7.4). For each sample, 20 scans from 200 to 260 nm were averaged.

Immunostaining

The levels of VprBP and H2AT120p in tumors tissues were determined in FDA human tumor organ tissue microarray, which includes 16 types of organ cancer with matched or unmatched adjacent normal tissue (US Biomax, Inc). The formalin-fixed, paraffin-embedded sections were blocked by treating with blocking reagent (50 mM Tris-HCl, pH 7.5, 150 mM NaCl, 0.3% Triton X-100, and 5% normal goat serum) for 30 min at room temperature and incubated with VprBP and H2AT120p antibodies at 4° C. overnight. Immunodetection was performed using ABC reagent (Vectorstain). DAB (Vector Lab) was used for color development and hematoxylin (Sigma) was used for counterstaining. The intensity and distribution patterns of staining were evaluated by semiquantitative immunohistochemical assessment. The intensity of staining was graded from – to +++ (–, no staining; +, weak staining; ++, moderate staining; and +++, strong staining) The distribution of staining was classified from 0 to 3 (0, 0-20%; 1, 21-50%; 2, 51-80%; 3, 81-100%). For immunofluorescence of DU145 cells, cells were treated with DMSO or B32B3 (0.5 μM) for 24 h and fixed with 4% paraformaldehyde for 15 min. The corresponding samples were permeabilized with 0.3% Triton X-100 for 15 min and immunostained with H2AT120p antibody.

RNA Interference

DNA oligonucleotides encoding VprBP shRNA1 (5'-CGAGAAACTGAGTCAAATGAA-3') (SEQ ID NO: 1), VprBP shRNA2 (5'-AATCACAGAGTATCTTAGA-3') (SEQ ID NO: 2) and Bub1 shRNA (5'-CGAGGTTAATC-CAGCACGTAT-3') (SEQ ID NO: 3) were subcloned into pLKO.1-puro (Addgene) lentiviral vector according to standard procedures. To produce virus particles, 293T cells were cotransfected with the plasmids encoding VSV-G, NL-BH and the shRNAs. Two days after transfection, the soups containing the viruses were collected and used to infect cancer cells in the presence of polybrene (8 μg/ml).

Cell Proliferation and Colony Formation Assays

Cell proliferation was assessed by the 3-(4,5-dimethylthiazol-2-yl)-2,5-diphenyltetrazolium bromide (MTT) assay as previously described (Kim, K. et al. (2012) Mol. Cell Biol. 32:783-796). To evaluate IC50 of compound B32B3 and B20H6, DU145 cells were treated with various concentrations (0.001, 0.005, 0.01, 0.05, 0.1, 1, 5, 10, and 20 μM) of compounds for 72 h and viability was measured by MTT assays. For soft agar colony formation assays, DU145 cells were treated with B32B3 (0.5, 1, and 3 μM). Cells were suspended in semisolid medium (DMEM 10% FBS plus 0.3% ultra pure noble agar) at concentrations of $2 \times 10^5$ cells/ml, added over a layer of 0.6% agar in RPMI on 35 mm plate and incubated for an additional 21 days. The colonies in each well were stained with 0.005% crystal violet in 20% ethanol, counted and photographed. All assays were run in triplicate, and results presented are the average of three individual experiments.

Microarray and qRT-PCR

Total RNA was isolated from mock- or VprBP-depleted cells using the TRIzol reagent according to the manufacturer's instructions (Invitrogen). Gene expression microarray experiments were conducted using a whole-genome expression array (Human HT-12 v4 Expression BeadChip, Illumina). This high density oligonucleotide array chip targets more than 47000 probe sequences derived from National Center for Biotechnology Information Reference Sequence (NCBI) RefSeq Release 38 (Nov. 7, 2009) and other sources. Data were processed and analyzed by the ArrayPipe software (www.pathogenomics.ca/arraypipe). Genes whose expression level was increased or decreased by a factor of >1.7 after VprBP knockdown are listed in Tables 2 and 3. For qRT-PCR, total RNA was extracted as described for microarray and subjected to RT reactions with the use of PerfeCta® SYBR Green FastMix (Quanta BIOSCIENCES) and an iCycler IQ5 real time cycler (Bio-Rad). The specificity of the amplification reactions were monitored by melting curve analysis. Assays were normalized to β-actin mRNA levels. The following primers were used for qRT-PCR:

BMF
(5'-CTCAGCCGACTTCAGCTCTT-3' (SEQ ID NO: 13) and
5'-AGCCAGCATTGCCATAAAAG-3' (SEQ ID NO: 14)), NKX3-1
(5'-AGAAAGGCACTTGGGGTCTT-3' (SEQ ID NO: 15) and
5'-TCCGTGAGCTTGAGGTTCTT-3' (SEQ ID NO: 16)), NOV
(5'-ACGAGCTTTTGTCTCCGAAA-3' (SEQ ID NO: 17) and
5'-ACACCAGACAGCATGAGCAG-3' (SEQ ID NO: 18)), OPN3
(5'-GATCCCTTTTGCAGCTTCTG-3' (SEQ ID NO: 19) and
5'-TTTGGACCCATTGGTTTTGT-3' (SEQ ID NO: 20)),

```
SOCS2
(5'-AAAAGAGGCACCAGAAGGAA-3' (SEQ ID NO: 21) and
5'-GTCCGCTTATCCTTGCACAT-3' (SEQ ID NO: 22)), SOCS3
(5'-GCCACCTACTGAACCCTCCT-3' (SEQ ID NO: 23) and
5'-ACGGTCTTCCGACAGAGATG-3' (SEQ ID NO: 24)), TNFSF10
(5'-TTCACAGTGCTCCTGCAGTC-3' (SEQ ID NO: 25) and
5'-ACGGAGTTGCCACTTGACTT (SEQ ID NO: 26)),
and TOB1
(5'-GGTGAAAAGGGACCAGTGAA-3' (SEQ ID NO: 27) and
5'-TGGAGAGCTGGACACTGATG (SEQ ID NO: 28)).
```

Chromatin Immunoprecipitation (ChIP)

Mock-depleted or VprBP-depleted DU145 cells were grown to 70-80% confluence, cross-linked with 1% formaldehyde for 10 min, and processed for ChIP as recently described (Kim, K. et al. (2012) Mol. Cell Biol. 32:783-796). ChIP assays on B32B2-treated cells were performed in a similar manner, except that DU145 cells were treated with DMSO or 1 µM B32B3 for 24 h. All samples were run in triplicate and results were averaged. Sequences of the primers used for quantitative real time PCR (qPCR) are as follows:

```
NOV
(promoter,
5'-GCACCAGTGTTGAAGTGTGG-3' (SEQ ID NO: 29) and
5'-GGCATGCTTGTCATCTCTCA-3' (SEQ ID NO: 30); TSS,
5'-GCCCTAAGGAGAGCAGCAC-3' (SEQ ID NO: 31) and
5'-TTCGCTGTAGATTGGCACTG-3' (SEQ ID NO: 32); coding,
5'-CTGCTCATGCTGTCTGGTGT-3' (SEQ ID NO: 33) and
5-AGCTGCAGGAGAAGAGGTCA (SEQ ID NO: 34)), OPN3
(promoter,
5'-TAGCTTGCACAAACCCTGTG-3' (SEQ ID NO: 35) and
5'-TGTGGTTGCACAATCCCTAA-3' (SEQ ID NO: 36); TSS,
5'-GAAGGTGCCCAGCCAGTG-3' (SEQ ID NO: 37) and
5'-GCCTGCTCTAGCCATTGTG-3' (SEQ ID NO: 38); coding,
5'-CAGGACTCCATTCCTGTGGT-3' (SEQ ID NO: 39) and
5'-GGTTTCGTGCCTTGTTGAGT-3' (SEQ ID NO: 40)), SOCS2
(promoter,
5'-GAAACGGGGTTGGCTGTAG-3' (SEQ ID NO: 41) and
5'-GTCGCAATACACAGGCTTCA-3' (SEQ ID NO: 42); TSS,
5'-ATCCTCGAGGCTTTTGTGTG-3' (SEQ ID NO: 43) and
5'-TCCCCCGTTAACGTTTAATTT-3' (SEQ ID NO: 44); coding,
5'-AGGATCTGGGGAGAAAGAGC-3' (SEQ ID NO: 45) and
5'-GGGTCATGAGAGAAGGGTCA-3' (SEQ ID NO: 46)), SOCS3
(promoter,
5'-CCGGAAATTCTCTCCTGCTA-3' (SEQ ID NO: 47) and
5'-GGAGAGCTCGAGGTGGAAC-3' (SEQ ID NO: 48); TSS,
5'-CTCTCGTCGCGCTTTGTCT-3' (SEQ ID NO: 49) and
5'-GGAGCAGGGAGTCCAAGTC-3' (SEQ ID NO: 50); coding,
5'-ATGGTCACCCACAGCAAGTT-3' (SEQ ID NO: 51) and
5'-GCTGCACATTGGACTCAAAA-3' (SEQ ID NO: 52)), and TNFSF10
(promoter,
5'-AAAATTAGCTGGGCATGGTG-3' (SEQ ID NO: 53) and
5'-AACCTCCACCTCCCAGATTC-3' (SEQ ID NO: 54); TSS,
5'-GGGACAGTTGCAGGTTCAAT-3' (SEQ ID NO: 55) and
5'-GGAGCACTGTGAAGATCACG-3' (SEQ ID NO: 56); coding,
5'-ATCCAAAGGGACTGGAGCTT-3' (SEQ ID NO: 57) and
5'-GCTGCACATTGGACTCAAAA-3' (SEQ ID NO: 58)).
```

B32B3 Stability Assessment

To assess the metabolic stability of B32B3 in mouse, dog, monkey, and human plasma, the compound was spiked into blank plasma to a concentration of 10 µM. At 0, 15, 30, 60, 90, and 120 min time points, a 30 µl aliquot was collected and mixed with 270 µl acetonitrile solution for protein precipitation. After centrifugation, the supernatant was analyzed by LC-MS/MS. In vitro half-life of B32B3 in plasma was calculated using the slope (k) of the log-linear regression from the concentration remaining parent compound versus time.

$$T_{1/2} = -\ln 2/k$$

Mouse Pharmacokinetics of B32B3

Mouse pharmacokinetic study was carried out using mice (n=5) that were fasted for 12 h prior to and 2 h after dosing with B32B3 (5 mg/kg). Blood samples were collected from orbital sinus at 10, 30, 60, 120, 240, and 480 min post dose. The plasma was separated from blood samples by centrifugation and analyzed in the Agilent 1200 HPLC system coupled to Agilent 6460A QQQ mass spectrophotometer. The plasma concentration-time data were analyzed by noncompartmental analysis using WinNonlin version 4.1 (Pharsight).

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

TABLE 1

Immunohistochemical staining of VprBP and H2A T120p in tissue microarray of human specimens, related to FIG. 2.

| No. | Organ | Pathology diagnosis | Grade | Stage | VprBP staining | H2A T120p staining |
|---|---|---|---|---|---|---|
| 1 | Esophagus | Squamous cell carcinoma | 3 | IIa | 3/++ | 3/+ |
| 2 | Esophagus | Squamous cell carcinoma | 3 | IIa | 2/++ | 2/+ |
| 3 | Esophagus | Adenocarcinoma | 1 | IIa | 3/++ | 3/++ |
| 4 | Esophagus | Cancer adjacent normal esophagus tissue of No.1 | | | 0/− | 0/− |
| 5 | Esophagus | Cancer adjacent normal esophagus tissue | | | 0/+ | 0/+ |
| 6 | Esophagus | Cancer adjacent normal esophagus tissue (fibrous tissue and blood vessel) | | | 0/+ | 0/− |
| 7 | Stomach | Adenocarcinoma | 3 | Ib | 1/++ | 1/++ |
| 8 | Stomach | Adenocarcinoma | | IIIa | 1/+ | 0/+ |
| 9 | Stomach | Adenocarcinoma (stomach tissue) | 2 | IV | 0/++ | 1/++ |
| 10 | Stomach | Cancer adjacent normal stomach tissue | | | 0/+ | 0/+ |
| 11 | Stomach | Cancer adjacent normal stomach tissue | | | 0/+ | 0/+ |
| 12 | Stomach | Cancer adjacent normal stomach tissue of No.9 | | | 0/+ | 0/+ |
| 13 | Colon | Adenocarcinoma | 2 | IIb | 0/+ | 0/+ |
| 14 | Colon | Adenocarcinoma | 2-3 | IIa | 2/++ | 3/+++ |
| 15 | Colon | Mucinous Adenocarcinoma | 3 | III | 2/+++ | 3/+++ |
| 16 | Colon | Cancer adjacent normal colon tissue | | | 0/+ | 0/+ |
| 17 | Colon | Cancer adjacent normal colon tissue of No. 15 | | | 0/− | 0/+ |
| 18 | Colon | Cancer adjacent normal colon tissue | | | 0/− | 1/+ |
| 19 | Rectum | Adenocarcinoma | 1 | IIb | 0/+ | 0/+ |
| 20 | Rectum | Adenocarcinoma | 3 | IIb | 1/+ | 1/+ |
| 21 | Rectum | Adenocarcinoma | 3 | III | 0/− | 0/− |
| 22 | Rectum | Cancer adjacent normal rectum tissue of No. 19 | | | 0/− | 0/− |
| 23 | Rectum | Cancer adjacent normal rectum tissue of No. 20 | | | 0/+ | 0/+ |
| 24 | Rectum | Cancer adjacent normal rectum tissue of No. 21 | | | 0/− | 0/− |
| 25 | Liver | Hepatocellular carcinoma | 2 | II | 2/++ | 2/++ |
| 26 | Liver | Hepatocellular carcinoma | 2 | II | 2/++ | 2/++ |
| 27 | Liver | Hepatocellular carcinoma | 2 | II | 3/+++ | 3/+++ |
| 28 | Liver | Cancer adjacent normal liver tissue | | | 0/+ | 1/+ |
| 29 | Liver | Cancer adjacent normal liver tissue | | | 1/+ | 1/+ |
| 30 | Liver | Cancer adjacent normal liver tissue of No. 27 | | | 1/+ | 1/+ |
| 31 | Lung | Adenocarcinoma | 2 | II | 3/+++ | 3/+++ |
| 32 | Lung | Adenocarcinoma | 3 | I | 3/++ | 3/++ |
| 33 | Lung | Squamous cell carcinoma | 3 | I | 3/++ | 3/+++ |
| 34 | Lung | Cancer adjacent normal lung tissue of No. 31 | | | 0/− | 0/− |
| 35 | Lung | Cancer adjacent normal lung tissue | | | 0/− | 0/+ |
| 36 | Lung | Cancer adjacent normal lung tissue of No. 33 | | | 0/− | 0/− |
| 37 | Kidney | Clear cell carcinoma | 1 | II | 3/++ | 3/++ |
| 38 | Kidney | Clear cell carcinoma (sparse) | | I | 0/− | 0/− |
| 39 | Kidney | Clear cell carcinoma | 1 | I | 1/+ | 2/++ |
| 40 | Kidney | Cancer adjacent normal kidney tissue | | | 0/− | 0/− |
| 41 | Kidney | Cancer adjacent normal kidney tissue of No. 39 | | | 0/− | 0/− |
| 42 | Kidney | Cancer adjacent normal kidney tissue | | | 0/− | 0/− |
| 43 | Breast | Invasive ductal carcinoma | 2 | IIIb | 2/+++ | 2/+++ |
| 44 | Breast | Invasive ductal carcinoma | 2 | IIb | 2/++ | 2/++ |
| 45 | Breast | Invasive ductal carcinoma | 2 | IIIb | 2/++ | 2/++ |
| 46 | Breast | Cancer adjacent normal breast tissue (fibrofatty tissue and blood vessel) of No. 43 | | | 0/− | 0/− |
| 47 | Breast | Cancer adjacent normal breast tissue of No. 44 | | | 0/− | 0/− |

TABLE 1-continued

Immunohistochemical staining of VprBP and H2A T120p in tissue microarray of human specimens, related to FIG. 2.

| No. | Organ | Pathology diagnosis | Grade | Stage | VprBP staining | H2A T120p staining |
|---|---|---|---|---|---|---|
| 48 | Breast | Cancer adjacent normal breast tissue | | | 0/− | 0/+ |
| 49 | Uterine | Squamous cell carcinoma cervix | 1 | IIIa | 3/+++ | 2/++ |
| 50 | Uterine | Squamous cell carcinoma cervix | 2 | Ib | 2/++ | 2/++ |
| 51 | Uterine | Squamous cell carcinoma cervix | 1 | Ib | 2/++ | 3/++ |
| 52 | Uterus | Cancer adjacent normal uterine cervix tissue | | | 0/+ | 0/− |
| 53 | Uterus | Cancer adjacent normal cervical canal tissue | | | 0/− | 0/− |
| 54 | Uterus | Cancer adjacent normal uterine cervix tissue | | | 0/− | 0/+ |
| 55 | Ovary | Serous adenocarcinoma | 3 | I | 2/+++ | 2/++ |
| 56 | Ovary | Serous papillary adenocarcinoma | 2 | Ia | 2/++ | 3/+++ |
| 57 | Ovary | Serous papillary adenocarcinoma | 2 | I | 2/++ | 2/++ |
| 58 | Ovary | Cancer adjacent normal ovary tissue | | | 0/− | 0/+ |
| 59 | Ovary | Cancer adjacent normal ovary tissue | | | 0/− | 0/+ |
| 60 | Ovary | Cancer adjacent normal ovary tissue | | | 0/+ | 0/+ |
| 61 | Bladder | Transitional cell carcinoma (fibrous tissue and blood vessel) | | II | 1/++ | 1/++ |
| 62 | Bladder | Transitional cell carcinoma | 2 | II | 3/++ | 2/++ |
| 63 | Bladder | Transitional cell carcinoma | 3 | III | 2/+++ | 3/+++ |
| 64 | Bladder | Cancer adjacent normal bladder tissue | | | 0/− | 0/+ |
| 65 | Bladder | Cancer adjacent normal bladder tissue (fibrous tissue and blood vessel) of No. 62 | | | 0/− | 0/+ |
| 66 | Bladder | Cancer adjacent normal bladder tissue | | | 0/+ | 0/+ |
| 67 | Lymph node | Diffuse B-cell lymphoma of left groin | | | 1/+ | 2/++ |
| 68 | Lymph node | Diffuse B-cell lymphoma of right submaxillary | | | 1/+ | 1/+ |
| 69 | Lymph node | Diffuse B-cell lymphoma of left groin | | | 2/++ | 1/+ |
| 70 | Lung | Cancer adjacent normal lymph node tissue | | | 0/− | 1/+ |
| 71 | Cardina | Cancer adjacent normal lymph node tissue | | | 0/+ | 1/+ |
| 72 | Cardina | Cancer adjacent normal lymph node tissue | | | 1/+ | 1/+ |
| 73 | Skin | Squamous cell carcinoma | 1 | II | 0/− | 0/− |
| 74 | Skin | Squamous cell carcinoma | 2 | II | 2/+++ | 2/+++ |
| 75 | Skin | Squamous cell carcinoma | 3 | II | 3/++ | 2/++ |
| 76 | Skin | Cancer adjacent normal skin tissue (sparse) | | | 0/− | 0/− |
| 77 | Skin | Cancer adjacent normal skin tissue of No. 74 | | | 0/− | 0/− |
| 78 | Skin | Cancer adjacent normal skin tissue | | | 0/− | 0/− |
| 79 | Cerebrum | Astrocytoma (brain tissue) | | | 0/− | 0/− |
| 80 | Cerebrum | Astrocytoma | 2 | | 0/+ | 1/+ |
| 81 | Cerebrum | Astro cytoma | 2 | | 2/++ | 2/++ |
| 82 | Cerebrum | Cancer adjacent normal brain tissue | | | 0/− | 0/− |
| 83 | Cerebrum | Cancer adjacent normal brain tissue | | | 0/+ | 0/+ |
| 84 | Cerebrum | Cancer adjacent normal brain tissue | | | 0/− | 0/− |
| 85 | Prostate | Adenocarcinoma | 1 | II | 3/+++ | 3/+++ |
| 86 | Prostate | Adenocarcinoma | 2 | II | 2/++ | 2/++ |
| 87 | Prostate | Adenocarcinoma | 2-3 | IV | 2/++ | 2/++ |
| 88 | Prostate | Cancer adjacent normal prostate tissue | | | 0/− | 0/+ |
| 89 | Prostate | Cancer adjacent normal prostate tissue | | | 0/− | 0/− |

TABLE 1-continued

Immunohistochemical staining of VprBP and H2A T120p in tissue microarray of human specimens, related to FIG. 2.

| No. | Organ | Pathology diagnosis | Grade | Stage | VprBP staining | H2A T120p staining |
|---|---|---|---|---|---|---|
| 90 | Prostate | Cancer adjacent normal prostate tissue | | | 0/− | 0/− |
| 91 | Pancreas | Adenocarcinoma | 2 | I | 0/+ | 1/+ |
| 92 | Pancreas | Adenocarcinoma (fibrous tissue) | | I | 0/+ | 0/+ |
| 93 | Pancreas | Adenocarcinoma | 3 | II | 0/+ | 0/+ |
| 94 | Pancreas | Cancer adjacent normal pancreas tissue | | | 0/+ | 0/+ |
| 95 | Pancreas | Cancer adjacent normal pancreas tissue of No. 92 | | | 0/+ | 0/+ |
| 96 | Pancreas | Cancer adjacent normal pancreas tissue | | | 0/+ | 0/+ |

TABLE 2

List of the genes upregulated in VprBP-depleted DU145 cells, related to FIG. 3.

| Probe ID | Fold change | Probe ID | Fold change | Probe ID | Fold change |
|---|---|---|---|---|---|
| LOC100008589 | 10.95621 | SPNS2 | 2.36224 | C14orf138 | 2.04492 |
| IL11 | 8.49622 | PPP1R15A | 2.35618 | MEPCE | 2.04475 |
| LOC100132564 | 5.57178 | PPIF | 2.34898 | C1orf182 | 2.03745 |
| RMRP | 5.13069 | TMEM156 | 2.34461 | RNU1G2 | 2.02637 |
| SCARNA18 | 4.73627 | TOB1 | 2.34228 | LOC100134364 | 2.02278 |
| LOC100008588 | 4.61836 | SNORD3D | 2.34112 | CIDECP | 2.01347 |
| CD24 | 4.18359 | SFXN1 | 2.33802 | NEXN | 2.00898 |
| SCARNA11 | 4.09227 | NTN4 | 2.33693 | SLC7A6 | 2.00493 |
| LOC100133565 | 3.75485 | LOC100132761 | 2.31059 | PCGF6 | 2.00423 |
| SLC22A18AS | 3.6869 | SOD2 | 2.30992 | ACYP2 | 2.00084 |
| Hs.543887 | 3.53457 | DUSP5 | 2.27879 | OPN3 | 1.9963 |
| KIAA1644 | 3.46544 | INA | 2.27157 | TJP2 | 1.99396 |
| MIR1978 | 3.36967 | RNU4ATAC | 2.26518 | SLC30A1 | 1.99278 |
| NOV | 3.20252 | PIGW | 2.24255 | TRNP1 | 1.99278 |
| SCARNA14 | 3.13199 | SNORA79 | 2.24197 | PSTK | 1.99014 |
| SCARNA8 | 3.08548 | PTGES | 2.23998 | RNU1-3 | 1.98478 |
| C6orf48 | 3.01226 | LOC389286 | 2.22735 | DPM2 | 1.98164 |
| SCARNA16 | 3.01107 | ATF5 | 2.21293 | LOC653610 | 1.98004 |
| CYP1B1 | 2.91347 | AP1G2 | 2.20253 | VGLL4 | 1.97867 |
| CYP1A1 | 2.85512 | APITD1 | 2.19888 | PPP3CA | 1.97129 |
| BMF | 2.84271 | LOC645381 | 2.19595 | S100A8 | 1.96175 |
| TXNIP | 2.81931 | ITGB2 | 2.19175 | DSTN | 1.96022 |
| KCNF1 | 2.78863 | TMEM79 | 2.17597 | ZNF185 | 1.95996 |
| LOC100132240 | 2.78373 | F3 | 2.17507 | RIOK1 | 1.95656 |
| UBC | 2.75736 | PMEPA1 | 2.15113 | MIR1974 | 1.95551 |
| IGFBP4 | 2.75471 | RNU6ATAC | 2.14132 | BEND6 | 1.95473 |
| LPAR1 | 2.71654 | HPCAL1 | 2.13553 | HERC4 | 1.95369 |
| HIF1A | 2.70422 | DGCR14 | 2.12664 | C12orf49 | 1.94948 |
| PPAP2B | 2.6787 | LOC100132771 | 2.12214 | TNFAIP2 | 1.94675 |
| AMHR2 | 2.64693 | KLRC3 | 2.12096 | SOCS3 | 1.94608 |
| RN7SK | 2.63914 | NCRNA00094 | 2.10456 | DICER1 | 1.94387 |
| SOCS2 | 2.62458 | ZC3H14 | 2.10195 | RNU1-5 | 1.94225 |
| SIK1 | 2.61433 | SLPI | 2.10091 | GEM | 1.94147 |
| SYDE1 | 2.60886 | Hs.545589 | 2.10006 | STX1A | 1.93722 |
| SCARNA23 | 2.55733 | CCNJL | 2.0949 | C22orf13 | 1.93676 |
| MICB | 2.49549 | C10orf140 | 2.0934 | C1orf86 | 1.93647 |
| SNORD3A | 2.48247 | LOC653354 | 2.08902 | SMOX | 1.93596 |
| CFL2 | 2.46382 | TNFRSF10D | 2.08423 | G0S2 | 1.93484 |
| IL6R | 2.44937 | C3 | 2.07775 | UCN | 1.93312 |
| LOC653879 | 2.44676 | HAS3 | 2.07037 | KGFLP1 | 1.93078 |
| SNORD3C | 2.44287 | COX11 | 2.06194 | LOC344887 | 1.92947 |
| LOC441763 | 2.43446 | ATP6V0E2 | 2.05825 | LOC642118 | 1.9271 |
| SLAIN1 | 2.43177 | ICMT | 2.0546 | COTL1 | 1.92546 |
| RCAN1 | 2.42618 | SUSD2 | 2.05412 | FOXE1 | 1.92539 |
| RRAD | 2.40797 | F13A1 | 2.05061 | Hs.575603 | 1.92446 |
| PPAPDC1A | 2.40078 | STAG3L4 | 2.04663 | REPIN1 | 1.92219 |
| C9orf6 | 1.91099 | OXTR | 1.81509 | RASD1 | 1.91895 |
| NUP160 | 1.91023 | IDS | 1.81451 | C19orf33 | 1.91508 |
| LOC100133511 | 1.90821 | UCRC | 1.81374 | PDE3B | 1.75473 |
| FAM46C | 1.8969 | RHOD | 1.81198 | CLCF1 | 1.75445 |
| PHF14 | 1.89165 | TNRC6B | 1.81057 | PPARG | 1.75354 |
| SH2D4A | 1.89006 | RAB23 | 1.81035 | MCTP1 | 1.7522 |

TABLE 2-continued

List of the genes upregulated in VprBP-depleted DU145 cells, related to FIG. 3.

| Probe ID | Fold change | Probe ID | Fold change | Probe ID | Fold change |
|---|---|---|---|---|---|
| RAB21 | 1.88609 | ZFAND2A | 1.80936 | RAB30 | 1.75208 |
| ST6GALNAC6 | 1.88472 | TGFB2 | 1.80851 | EIF6 | 1.7516 |
| Hs.565887 | 1.88382 | MORN2 | 1.80789 | TSEN2 | 1.75139 |
| HSD17B12 | 1.88248 | LOC100130992 | 1.80648 | CD7 | 1.7475 |
| LOC113386 | 1.88008 | LOC100129828 | 1.8052 | TCF3 | 1.74646 |
| TAF5L | 1.87947 | HNRPUL2 | 1.80508 | USP12 | 1.7454 |
| STIM2 | 1.87827 | KIAA2010 | 1.80332 | AGPAT5 | 1.74504 |
| RNU6-15 | 1.87587 | SPOCD1 | 1.80293 | BEGAIN | 1.74238 |
| KIAA1683 | 1.87508 | RNU4-2 | 1.8029 | LOC728640 | 1.74212 |
| TCTA | 1.8746 | BCL7B | 1.79941 | ODF2 | 1.74148 |
| GPR137B | 1.87293 | FGF2 | 1.7985 | MED1 | 1.74124 |
| MPDU1 | 1.86958 | CASD1 | 1.79472 | HMOX1 | 1.73955 |
| RNF7 | 1.86801 | REEP3 | 1.79401 | LOC645676 | 1.73679 |
| CLDN15 | 1.86474 | RCL1 | 1.78888 | LOC339804 | 1.73625 |
| RNU6-1 | 1.86224 | HBEGF | 1.78832 | NKX3-1 | 1.73619 |
| RNU1A3 | 1.86106 | ZCWPW1 | 1.78801 | TGM2 | 1.73592 |
| ZC3H8 | 1.85225 | CGGBP1 | 1.78799 | MIB2 | 1.73494 |
| PPARBP | 1.85133 | BRPF3 | 1.78795 | HIST1H2BK | 1.73493 |
| KYNU | 1.84888 | GLCCI1 | 1.78469 | Hs.556082 | 1.73316 |
| AKIRIN1 | 1.84823 | TOMM34 | 1.78467 | ODC1 | 1.73164 |
| MAPKAPK2 | 1.84637 | BTBD7 | 1.78078 | CCNYL1 | 1.73042 |
| SMG7 | 1.84559 | S100A13 | 1.77958 | GTF2IRD2B | 1.73017 |
| RNY1 | 1.84555 | FBXW2 | 1.77898 | C21orf2 | 1.72741 |
| Hs.534061 | 1.84254 | PINK1 | 1.77891 | Hs.568329 | 1.72736 |
| DLK2 | 1.8403 | RPL34 | 1.77762 | DDX10 | 1.72735 |
| TNFSF10 | 1.83912 | TRIM44 | 1.77663 | LGR4 | 1.72658 |
| F8A1 | 1.83828 | DYRK3 | 1.77298 | OBFC2A | 1.72458 |
| SCML2 | 1.83782 | DYSF | 1.77256 | KCMF1 | 1.72451 |
| ISCA1 | 1.8371 | IGF2BP3 | 1.77216 | GPX1 | 1.72445 |
| LOC401233 | 1.83563 | CHN1 | 1.7721 | BAD | 1.72434 |
| DNAJC25 | 1.8356 | DPP9 | 1.76985 | RNY4 | 1.72133 |
| Hs.91389 | 1.83318 | ARPC1A | 1.76981 | USP22 | 1.72014 |
| GBP1 | 1.83181 | CBLL1 | 1.76954 | ZNHIT6 | 1.71805 |
| KIAA1666 | 1.83127 | PVT1 | 1.7684 | LOC653450 | 1.71697 |
| PPL | 1.82944 | PEF1 | 1.76753 | IL1RL1 | 1.71563 |
| LOC402617 | 1.82572 | TMEM217 | 1.76675 | Hs.540724 | 1.7147 |
| SPNS2 | 1.82448 | C6orf66 | 1.76323 | KLK3 | 1.71446 |
| KLF10 | 1.82281 | H2AFY | 1.76152 | TMEM180 | 1.71051 |
| FAM168B | 1.82222 | C9orf169 | 1.76142 | HRB | 1.70994 |
| GLRX2 | 1.82176 | LAT | 1.76057 | LOC387763 | 1.70986 |
| LOC441481 | 1.82061 | MAX | 1.75785 | C19orf48 | 1.70956 |
| CPM | 1.81512 | CTRL | 1.75487 | AGFG1 | 1.70904 |
| IL4R | 1.70707 | C1GALT1 | 1.70454 | OAZ2 | 1.70851 |
| REV3L | 1.70646 | RBKS | 1.70249 | ZNF219 | 1.70716 |
| WNT7A | 1.70604 | LOC727945 | 1.70176 | | |
| RNU4-1 | 1.70594 | SCARNA20 | 1.70017 | | |

TABLE 3

List of the genes downregulated in VprBP-depleted DU145 cells, related to FIG. 3.

| Probe ID | Fold change | Probe ID | Fold change | Probe ID | Fold change |
|---|---|---|---|---|---|
| SNORD13 | −4.76013 | STMN3 | −2.69955 | VTA1 | −2.36258 |
| CYP24A1 | −4.69112 | HOMER2 | −2.69622 | PFKL | −2.35716 |
| RASL10A | −4.50653 | VPRBP | −2.69554 | CA2 | −2.35239 |
| CCL20 | −4.33102 | FBXO4 | −2.66715 | SEPT5 | −2.3515 |
| IGFBP3 | −4.12725 | ADAM23 | −2.66614 | CBS | −2.32465 |
| LCN2 | −3.99251 | HLA-DOB | −2.64214 | DDIT4 | −2.31864 |
| SRPX | −3.89196 | PTPRE | −2.63881 | RIMS3 | −2.31602 |
| SYTL2 | −3.72792 | DDAH1 | −2.62998 | GNG4 | −2.31208 |
| ERLIN2 | −3.708 | SELM | −2.61246 | B4GALNT1 | −2.31172 |
| SPP1 | −3.64917 | CFD | −2.61173 | NMD3 | −2.30645 |
| OPLAH | −3.56388 | LOC730415 | −2.60748 | KCNQ2 | −2.30063 |
| TMEM145 | −3.55171 | MCOLN2 | −2.60564 | ECHDC3 | −2.29554 |
| HLA-DMA | −3.54901 | NICN1 | −2.59474 | MOSPD3 | −2.29472 |
| PCK2 | −3.39215 | SCNN1A | −2.57872 | AIF1L | −2.29356 |
| ANG | −3.3747 | CYP4F11 | −2.56978 | CRIP1 | −2.28066 |
| RNASE4 | −3.34991 | EFHD1 | −2.56425 | HSPA5 | −2.26752 |
| KIF1B | −3.2912 | DPYSL4 | −2.54773 | LTBP4 | −2.26681 |
| GALNTL1 | −3.2398 | RBP1 | −2.54231 | F12 | −2.26624 |
| ACCN2 | −3.23115 | WFDC3 | −2.52798 | KCNK15 | −2.26529 |
| MAP1LC3A | −3.09754 | STAT4 | −2.51561 | RDH10 | −2.24289 |

TABLE 3-continued

List of the genes downregulated in VprBP-depleted DU145 cells, related to FIG. 3.

| Probe ID | Fold change | Probe ID | Fold change | Probe ID | Fold change |
|---|---|---|---|---|---|
| LAMP3 | −3.06117 | BBS7 | −2.51497 | LEPREL2 | −2.24037 |
| KISS1R | −3.01598 | CBLC | −2.51361 | PAQR8 | −2.23745 |
| DDIT4L | −3.00965 | CDC42EP5 | −2.50702 | TUBB2B | −2.2258 |
| CLYBL | −3.00486 | EPHX2 | −2.50536 | CLDN7 | −2.22503 |
| H1FX | −2.9432 | NUDT18 | −2.49831 | SEZ6L2 | −2.22419 |
| PRPH | −2.94106 | PGM2L1 | −2.48024 | HLA-DRB1 | −2.22167 |
| GLO1 | −2.94083 | ULBP1 | −2.47582 | MXRA7 | −2.21861 |
| EGR1 | −2.93183 | ELOVL4 | −2.46244 | CYP26B1 | −2.21718 |
| PRODH | −2.90908 | ASNS | −2.46226 | OXCT1 | −2.21436 |
| TMEM107 | −2.88271 | CMTM4 | −2.45959 | PLOD1 | −2.20886 |
| TMSB15A | −2.86058 | AHCTF1 | −2.45763 | TMEM45A | −2.20746 |
| FLJ20444 | −2.8544 | MAP4K1 | −2.45566 | SNX10 | −2.2021 |
| UPK1A | −2.8322 | FXYD6 | −2.44858 | S100A4 | −2.19894 |
| STS-1 | −2.82727 | TM7SF2 | −2.43709 | PIGZ | −2.19516 |
| LRRN2 | −2.80333 | COL6A1 | −2.43078 | WISP2 | −2.193 |
| PDIA4 | −2.79743 | MTX2 | −2.41788 | GNG7 | −2.18561 |
| GALC | −2.77678 | UBASH3B | −2.40128 | HSPB8 | −2.15889 |
| FUCA1 | −2.75977 | GOLSYN | −2.39573 | OSGIN2 | −2.15606 |
| TSTD1 | −2.74491 | H1F0 | −2.39163 | SLC2A3 | −2.15503 |
| CXorf61 | −2.73964 | MAPT | −2.38724 | MLLT11 | −2.1339 |
| RAB26 | −2.73737 | DHRS3 | −2.37749 | GNAI3 | −2.13342 |
| FGFBP1 | −2.73291 | MPZL2 | −2.37523 | CUGBP2 | −2.13211 |
| MGC39900 | −2.72135 | GXYLT1 | −2.3664 | JAZF1 | −2.1315 |
| HLA-DPA1 | −2.71792 | SGK | −2.36494 | ABHD1 | −2.12012 |
| CYP26A1 | −2.70874 | PARM1 | −2.36369 | SIRT4 | −2.11814 |
| SLC24A6 | −2.70779 | GRHPR | −2.36322 | N4BP1 | −2.11786 |
| CERCAM | −2.10843 | BDNF | −1.79092 | ROR1 | −2.11773 |
| FAM84B | −2.10647 | MAOA | −1.79078 | RDM1 | −2.1113 |
| ESPL1 | −2.01313 | DECR1 | −1.73255 | ZFC3H1 | −1.85227 |
| RPRML | −2.00454 | FKBP5 | −1.73199 | IDH1 | −1.85147 |
| NSL1 | −2.00364 | LRRC45 | −1.73121 | GJB2 | −1.84965 |
| SH3BGRL2 | −2.00204 | NRG4 | −1.73096 | ECM1 | −1.82754 |
| NDRG1 | −2.00143 | PYCR1 | −1.73012 | CRELD2 | −1.8274 |
| HES7 | −2.00073 | PQLC3 | −1.72937 | PLCG2 | −1.82466 |
| FEZ1 | −1.99933 | NES | −1.71073 | DNAJC4 | −1.79501 |
| FLJ22536 | −1.99034 | CYP4V2 | −1.70899 | CACNA2D2 | −1.79385 |
| MKRN1 | −1.99011 | TFPI | −1.70884 | RBP7 | −1.79384 |
| CHST13 | −1.95803 | WFDC2 | −1.70331 | CEP70 | −1.79346 |
| CENTA1 | −1.95223 | PRSS12 | −1.70275 | ACSM3 | −1.79277 |
| CXCL2 | −1.93765 | MAPK3 | −1.70214 | CTSH | −1.79174 |
| STRADB | −1.9103 | MOCOS | −1.7021 | CNTN1 | −1.86233 |
| NCAPG2 | −1.91024 | PPFIA4 | −1.70174 | SSH3 | −1.86181 |
| FBXO2 | −1.90867 | KDELR3 | −1.70166 | TCIRG1 | −1.86102 |
| RPS6KA5 | −1.90636 | RALBP1 | −1.70153 | CIB2 | −1.86029 |
| PKD2 | −1.90543 | ASNSD1 | −1.7009 | GLT25D2 | −1.85831 |
| SLC35C1 | −1.90514 | CXCL1 | −1.70045 | EFEMP2 | −1.85527 |
| ID2 | −1.90325 | ASNSD1 | −1.7009 | PALM | −1.85364 |
| NRBP2 | −1.90295 | CXCL1 | −1.70045 | MXD3 | −1.85281 |
| ZWILCH | −1.89623 | CHST6 | −1.89448 | HMGCL | −1.88948 |
| FGFR3 | −1.89613 | THBS3 | −1.89045 | XPR1 | −1.88925 |

TABLE 4

Inhibition of human kinases by B32B3, related to FIG. 4.

| Kinase | IC$_{50}$ (μM) |
|---|---|
| VprBP | 0.6 |
| AKT1 | >10 |
| AKT3 | >10 |
| ATM | >10 |
| ATR | >10 |
| AURKA | >10 |
| AURKB | >10 |
| BCK | >10 |
| BUB1 | >10 |
| CDK2 | >10 |
| CDK7 | >10 |
| CDK9 | >10 |
| CDK18 | >10 |
| CHK1 | >10 |
| CHK2 | >10 |
| CSNK1D | >10 |
| CSK1E | >10 |
| DNAPK | >10 |
| DYRK1 | >10 |
| EEF2K | >10 |
| GSK3β | >10 |
| HCK | >10 |
| LCK | >10 |
| PKM2 | >10 |
| PKN2 | >10 |
| PRKCD | >10 |
| PLK1 | >10 |
| PLK2 | >10 |
| RSK2 | 8.6 |

TABLE 4-continued

Inhibition of human kinases by B32B3, related to FIG. 4.

| Kinase | IC$_{50}$ (μM) |
|---|---|
| RSK3 | >10 |
| STK25 | >10 |
| STK33 | >10 |
| SYK | >10 |
| VRK2 | >10 |

What is claimed is:

1. A compound of the formula:

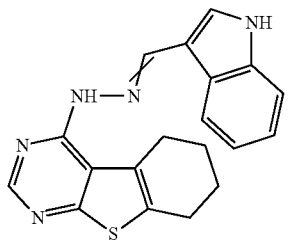 [SMILES: c1ccc2c(CNNc3ncnc4sc5c(c34)CCCC5)c[nH]c2c1]

or a pharmaceutically acceptable salt or a solvate thereof.

2. A composition comprising a carrier and a compound of the formula:

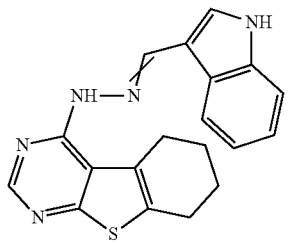 [SMILES: c1ccc2c(CNNc3ncnc4sc5c(c34)CCCC5)c[nH]c2c1]

or a pharmaceutically acceptable salt or a solvate thereof.

3. A method for treating cancer in a patient in need thereof, wherein the cancer is selected from the group consisting of bladder cancer, breast cancer and prostate cancer, comprising administering to the patient an effective amount of the composition of claim 2 or the compound of claim 1.

4. The composition of claim 2, wherein the carrier is a pharmaceutically acceptable carrier or an in situ device.

5. The composition of claim 4, wherein the device is a catheter.

6. A method for:

a. inhibiting the growth of a cancer cell wherein the cancer cell is a breast, a prostate or a bladder cancer cell; or b. inhibiting phosphorylation of H2AT120P in a cell, comprising contacting the cell with an effective amount of the composition of claim 2 or the compound of claim 1.

7. The method of claim 3, wherein the compound is administered in an amount from about 0.1 mg/day to about 10 g/day or about 1 mg/day to about 10 g/day.

* * * * *